United States Patent
Earthman et al.

(10) Patent No.: US 12,369,846 B2
(45) Date of Patent: Jul. 29, 2025

(54) DETERMINATION OF STRUCTURAL CHARACTERISTICS OF AN OBJECT

(71) Applicant: Perimetrics, LLC

(72) Inventors: James C. Earthman, Irvine, CA (US); Cherilyn G. Sheets, Newport Beach, CA (US); John Michael Elam, Woodland Hills, CA (US); Robert Hayman, Los Angeles, CA (US)

(73) Assignee: PERIMETRICS, INC., Redmond, WA (US)

( * ) Notice: Subject to any disclaimer, the term of this patent is extended or adjusted under 35 U.S.C. 154(b) by 635 days.

(21) Appl. No.: 16/959,406

(22) PCT Filed: Dec. 30, 2018

(86) PCT No.: PCT/US2018/068083
§ 371 (c)(1),
(2) Date: Jun. 30, 2020

(87) PCT Pub. No.: WO2019/133946
PCT Pub. Date: Jul. 4, 2019

(65) Prior Publication Data
US 2020/0337630 A1 Oct. 29, 2020

Related U.S. Application Data

(60) Provisional application No. 62/692,618, filed on Jun. 29, 2018, provisional application No. 62/687,730, (Continued)

(51) Int. Cl.
*A61B 5/00* (2006.01)
*A61B 5/0534* (2021.01)

(52) U.S. Cl.
CPC ......... *A61B 5/4547* (2013.01); *A61B 5/0534* (2013.01); *A61B 2562/0204* (2013.01); *A61B 2562/0261* (2013.01)

(58) Field of Classification Search
None
See application file for complete search history.

(56) References Cited

U.S. PATENT DOCUMENTS

| | | | | |
|---|---|---|---|---|
| 4,499,906 A | * | 2/1985 | Wohlgemuth | G01N 3/317 600/589 |
| 5,518,008 A | * | 5/1996 | Cucchiaro | A61B 9/00 600/590 |

(Continued)

FOREIGN PATENT DOCUMENTS

| | | | |
|---|---|---|---|
| JP | 2006317348 A | * 11/2006 | |
| WO | WO-02082998 A1 | * 10/2002 | A61B 5/036 |

OTHER PUBLICATIONS

Machine English translation of JP 2006317348 A, 2025 Clarivate Analytics, 21 pages, printed on Mar. 24, 2025 (Year: 2025).*

*Primary Examiner* — Matthew Kremer
(74) *Attorney, Agent, or Firm* — Quan & Associates; Christopher Quan

(57) ABSTRACT

The present invention relates generally to a system and method for measuring the structural characteristics of an object. The object is subjected to an energy application processes and provides an objective, quantitative measurement of structural characteristics of an object. The system may include a device, for example, a percussion instrument, capable of being reproducibly placed against the object undergoing such measurement for reproducible positioning. The system includes features for adjusting the energy applied to an energy application tool to compensate for orientation of the device relative to the horizontal. The system also includes a disposable feature or assembly for minimizing cross-contamination between tests. The structural characteristics as defined herein may include vibration damping capacities, acoustic damping capacities, structural integrity or structural stability.

11 Claims, 17 Drawing Sheets

Related U.S. Application Data filed on Jun. 20, 2018, provisional application No. 62/612,440, filed on Dec. 30, 2017.

(56) References Cited

U.S. PATENT DOCUMENTS

| | | | | |
|---|---|---|---|---|
| 5,553,618 A * | 9/1996 | Suzuki | ............. | A61N 7/02 |
| | | | | 601/3 |
| 2003/0100040 A1* | 5/2003 | Bonnecaze | ......... | A61B 5/0031 |
| | | | | 435/14 |
| 2010/0210920 A1* | 8/2010 | Ziv | ............. | G16H 40/20 |
| | | | | 600/301 |
| 2013/0174639 A1* | 7/2013 | Earthman | ............. | A61B 9/00 |
| | | | | 367/189 |

* cited by examiner

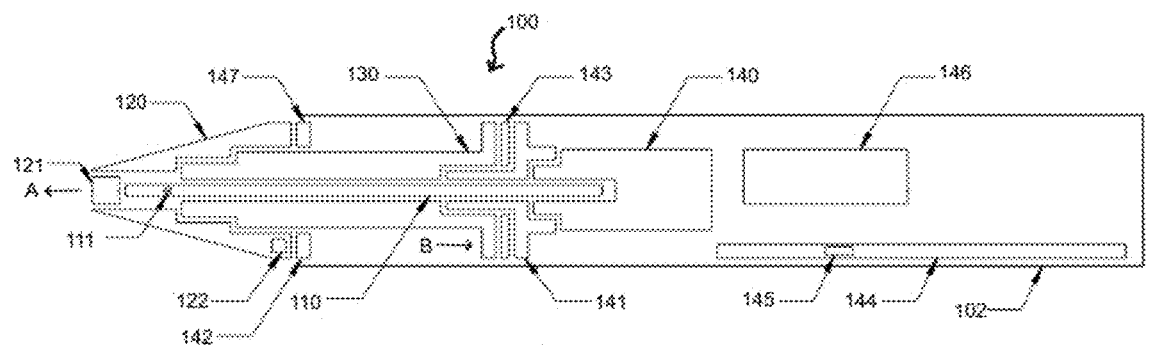

DETERMINATION OF STRUCTURAL CHARACTERISTICS OF AN OBJECT

CROSS-REFERENCE TO RELATED APPLICATIONS

This application is a 371-national phase application of Patent Cooperation Treaty International Application Ser. No. PCT/US2018/068083, filed Dec. 30, 2018, entitled "DETERMINATION OF STRUCTURAL CHARACTERISTICS OF AN OBJECT", which claims the benefit and priority of the following United States Provisional Patent Applications: Ser. No. 62/692,618, filed Jun. 29, 2018, entitled "SYSTEM AND METHOD FOR DETERMINING STRUCTURAL CHARACTERISTICS OF AN OBJECT"; Ser. No. 62/687,730, filed Jun. 20, 2018, entitled "SYSTEM AND METHOD FOR DETERMINING STRUCTURAL CHARACTERISTICS OF AN OBJECT"; and Ser. No. 62/612,440, filed Dec. 30, 2017, entitled "SYSTEM AND METHOD FOR DETERMINING STRUCTURAL CHARACTERISTICS OF AN OBJECT"; the contents of all of the foregoing applications are hereby incorporated by reference in their entireties.

FIELD OF THE INVENTION

This invention relates generally to evaluation of the structural properties of an object; and more specifically relates to evaluation of the structural characteristics that reflects the integrity of an object using a controlled energy application thereon.

BACKGROUND OF THE INVENTION

When an object is subjected to an impact force, a stress wave is transmitted through the object. This stress wave causes deformations in the internal structure of the object. As the object deforms it acts, in part, as a shock absorber, dissipating a portion of the mechanical energy associated with the impact. The ability of the object to dissipate mechanical energy, commonly referred to as the "damping capacity" of the object, depends on several factors, including the type and structural integrity of the materials making up the object.

There are instruments that are capable of measuring the damping capacity of an object. An example of such an instrument is described in U.S. Pat. No. 6,120,466 ("the '466 patent"). The instrument disclosed in the '466 patent provides an objective, quantitative measurement of the damping capacity of an object, referred to as the loss coefficient 17. The energy of an elastic wave attenuates relatively quickly in materials with a relatively high loss coefficient, whereas the energy of an elastic wave attenuates relatively slowly in materials with a relatively low loss coefficient.

The damping capacity of an object is an important parameter in a wide variety of applications. For example, in the field of dentistry, when a healthy tooth is subjected to an impact force, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth.

SUMMARY OF THE INVENTION

The present invention relates to a system and method for measuring structural characteristics of an object in a non-invasive manner and/or using a non-destructive method of measurement having a device capable of operating by holding the device at varying angles from the horizontal and modulating the energy application process to mimic a substantially horizontal position during measurement. The device for determining structural characteristics of an object, includes a housing having an open front end and a longitudinal axis; an energy application tool mounted inside the housing, having a resting and an active configuration; a drive mechanism supported inside the housing for activating the energy application tool between the resting and active configurations to apply a set amount of energy at a horizontal orientation; and an inclinometer adapted to measure inclination of the energy application tool relative to the horizontal. The drive mechanism varies the amount of energy applied to activate the energy application tool between the resting and active configurations based on the inclination to at least approximate the set amount of energy at inclinations other than horizontal. The drive mechanism may include an electromagnetic coil and may vary the amount of energy applied (e.g. varying voltage, current or both), may vary the coil drive times (varying the length of time the coil is energized or activated), may vary the coil delay times (varying the time between driving activities), may vary the number of coil energizations (i.e. varying the number of drive pulses applied), polarity of the coil and/or a combination thereof. These factors, including varying power, drive times, polarity and delay times may be managed through varying the firmware settings for power, drive time, number of drives, polarity and drive delay of the energizing of the coil for the desired results. Without wishing to be bound to any particular theory, it is surmised multiple variations may be employed to achieve the desired result and the firmware may be designed to select a particular solution or to select an optimal solution for certain instances.

The object may be subjected to an energy application process and the system is adapted for providing an objective, quantitative measurement of structural characteristics of the object after the energy application process. The system and method of the present invention may, such as increase flexibility of operation, for example, to adapt for reaching hard to reach objects, both anatomical and non-anatomical, to detect any abnormalities that may be present in an object to generate more reproducible measurements, and also to better be able to detect any abnormalities that may be present in an object. The device may include a housing with a hollow interior and an open end through which an energy application tool, including any tool capable of applying any types of energy to the object, for example, a tool capable of applying mechanical energy to the object, such as a tapping rod positioned inside the housing passes through to reach the object undergoing measurement, an electromagnetic energy of any frequency, for example, light, a sound wave such as acoustic energy.

For example, the system may include a device for performing a percussion action on an object. The device, having a housing with a hollow interior and an open end through which energy may be applied by an energy application tool, including any tool capable of applying any types of energy to the object including mechanical, sound or electromagnetic energy may be positioned. In one embodiment, a tool capable of applying mechanical energy to the object, such as a tapping rod may be positioned inside the housing passes through to reach the object undergoing measurement. In another embodiment, an electromagnetic energy source of any frequency, such as light energy, for example, may be positioned inside the housing. In a further example, a sound energy source such as an ultrasonic transducer or any acoustic energy source, may be positioned inside the housing.

The housing of the device may include a longitudinal axis and in general, the longitudinal axis of the device may be positioned from a substantially horizontal direction to making an angle with the horizontal direction. The angle may be, for example, of any angle, more for example, vary from zero degrees to about plus/minus forty-five degrees, even more for example, vary from zero degrees to about plus/minus thirty degrees. In one embodiment, the longitudinal axis of the energy application tool positioned inside the housing remains at all times in substantially parallel relationship to the housing during operation. In another embodiment, the housing of the device may include a longitudinal axis with a longitudinal axis of an energy application tool to be positioned from a substantially horizontal direction substantially parallel to the longitudinal axis of the device housing with a tip portion of the tool being substantially perpendicular to the contact surface of the object, to the longitudinal axis of the energy application tool to be making an acute angle with the longitudinal axis of the housing, while the tip of the tool remains substantially perpendicular to the contact surface of the object. In this latter embodiment, if the tool is a mechanical tool, such as a tapping rod, it may or may not include a removable tool tip that is substantially perpendicular to the longitudinal axis of the tool and housing.

In any of the above or below described embodiments, the device may include a handpiece and the longitudinal axis of the device may be positioned at any angle with the horizontal direction. The angle may be, for example, of any angle, more for example, vary from zero degrees to about plus/minus forty-five degrees., even more for example, vary from zero degrees to about plus/minus thirty degrees.

As mentioned above, the energy application tool may be adapted to move from a resting position to an active position by a drive mechanism and during a measurement, may impact the object in the active position. In general, the energy application tool may repeatedly impact an object during each measurement. The energy application tool itself may, if a mechanical tool is used, the tool may move and a physical contact with the object may ensue at impact during measurement, or the energy itself may impact the object during measurement, if any other energy tool such as electromagnetic or sound, is used. When these other energy tools are used, there may not be any physical movement of the tool between active and passive configuration of the tool but may be defined by that of energy being on and off.

The device of the present invention may be, for example, a percussion instrument, which may or may not include at least a portion, such as a sleeve portion extending from the housing for a distance, capable of being reproducibly placed in contact with the object undergoing such measurement. The energy application tool, such as a tapping rod may be programmed to impact an object a certain number of times per minute at substantially the same speed and the deceleration information of the tool or the response of the object from the impact is recorded or compiled for analysis by the system. In one embodiment, the device and hardware may communicate via a wire connection. In another embodiment, the device and hardware may communicate via a wireless connection.

For the device of the present invention with at least a portion capable of being reproducibly placed in contact with the object, the device may be capable of more reproducible measurements, including for an object present in, for example, space restricted, and/or difficult to reach locations.

In one embodiment, and the energy application tool, for example, a tapping rod, has a length with a retracted or resting form or configuration and an extended or active form or configuration, the retracted form being retracted from or substantially coextensive with the open end of the housing if the energy application tool is a tapping rod. The movement of the energy application tool, for example, a tapping rod, may be effected by a drive mechanism mounted inside the housing for driving the tapping rod axially within the housing between the aforementioned retracted position and extended position during operation. In the extended position, the free end of the tapping rod is capable of extending or protruding from the open end of the housing. With the present invention that the device may be held at any angle from the horizontal, testing objects at a location that is harder to reach, for example, in the molar area of a patient's teeth, may also be undertaken In another embodiment, the resting configuration may be a form substantially parallel to the longitudinal axis of the housing, and the active configuration may be a form when the energy application tool, for example, a tapping rod, or impact rod mounted inside the housing forms an acute angle with the longitudinal axis of the housing, such as, for example, by rocking back and forth about a pivot point on the longitudinal axis. Thus, the energy application tool oscillates from the substantially parallel position to the longitudinal axis of the housing to a position making an acute angle with the longitudinal axis of the housing at a pivot point. The energy application tool may be held either horizontally or in other positions during measurement, and may have a tip portion that is substantially perpendicular to the major portion of the tool and maintains a constant length either at rest or at impact. The movement of the energy application tool, for example, a tapping rod, may be effected by a drive mechanism mounted inside the housing for driving the tapping rod from a substantially parallel position to the longitudinal axis of the housing to a position making an acute angle with the axis at a pivot point and back again, while the tip oscillates up and down in turn. Using this embodiment, measurements may be undertaken at locations which are relatively inaccessible such as, for example, in the molar area of a patient's teeth.

The energy application process of the device may be activated or triggered in a number of ways. In one embodiment, it may be activated via a mechanical mechanism, such as by a switch mechanism. In one aspect, a finger switch may be located at a convenient location on the device, such as the handpiece for easy activation by the operator. In another aspect, the switch mechanism may be triggered by applied pressure to the object through the sleeve, as noted above. In another embodiment, the energy application process of the device may be triggered via voice control or foot control.

Generally, the external switching device such as a flip switch, a rocking switch or a push button switch, may tend to restrict the manner an operator holds the instrument and thus may restrict the positioning of the instrument on the object, if it is handheld, for example, during measurement so as to enable easy access by the operator to the switching device for turning it on and/or off. To gain flexibility in positioning the instrument, voice control or remote control may generally be used, though such voice controls or remote controls can add complexity to the system. In the present invention, the same advantages of flexibility may be gained without such remote controls or added complexities.

In one exemplary embodiment, any of the systems described above may include an instrument having a housing with a hollow interior with an open end and an energy application tool, for example, a tapping rod, or impact rod mounted inside the housing for movement inside the housing. Located at the open end of the housing may be a sleeve portion present as an extension to the housing.

The sleeve portion may be open at its free end, with an object resting, pressing or contacting portion for resting on, pressing or contacting at least a portion of an object during measurement. The contact by the sleeve portion aids to stabilize the device on the object. During measurement, the force exerted by the sleeve portion on an object is controlled by an operator, and a proper force on the object may be important and may need to be monitored, since, for example, either insufficient or excessive force exerted by an operator may complicate the measurements and may even produce less accurate results in some instances. A sensor disposed inside the housing, not physically or mechanically coupled to the energy application tool may be present to ensure that a proper contact force by the contacting portion of the sleeve portion may be applied by the operator for better reproducibility, even by different operators. The force exerted on the sleeve portion may generally be separate and monitored separately from any forces on the energy application tool from performing a measurement.

In one embodiment, the sleeve portion is as immediately described above.

In another embodiment, the sleeve may include a tab protruding from a portion of its end so that when the open end of the sleeve is in contact with at least a portion of a surface of the object undergoing the measurement, the tab may be resting on a portion of the top of the object. The tab and the sleeve together assist in the repeatable positioning of the handpiece with respect to the object, thus results are more reproducible than without the tab. In addition, the tab may be adapted for repetitively placed substantially at the same location on the top of the object every time. The tab may be substantially parallel to the longitudinal axis of the sleeve so that the object contacting sleeve portion and the object contacting surface of the tab are substantially orthogonal to each other and resting on different surfaces of the object. The tab may also aid to minimize the motion of the object after application of energy in any direction other than a direction of energy application. On rare occasions, where the tab may interfere with a stable position on, for example a dental implant transfer abutment, a sleeve portion without a tab may be used for more stable placement lower on the abutment.

In a further embodiment, the sleeve may include a tab and a component, for example, a ridge, protrusion or other feature substantially orthogonal to the surface of the tab on the side adapted for facing the surface of an object. For example, for teeth, the ridge or protrusion may nest between adjacent teeth or other orthogonal surface and may thus aid in preventing any substantial lateral or vertical movement of the tab across the surface of the object and/or further aid in repeatability. The tab may be of sufficient length or width, depending on the length or width of the top portion of the object so that the ridge or protrusion may be properly located during operation. Again, the tab and the feature also aid in the reproducible results than without the tab.

The stabilization of the instrument effected by a tab or a tab and/or component may minimize any jerky action by the operator that may confound the testing results, for example, any defects inherent in the bone structure or physical or industrial structure may be masked by jerky action of the tester. This type of defect detection is important because the location and extent of the defect may impact dramatically upon the stability of the implant or physical or industrial structures. Generally, when lesions are detected, for example, in an implant, such as a crestal or apical defect, the stability of the implant may be affected if both crestal and apical defect are present. In the past, there is no other way of gathering this type of information other than costly radiation intensive processes. With the present device, this type of information may be gathered, and may be done in an unobtrusive, non-invasive manner.

The drive mechanism may be an electromagnetic mechanism and may include an electromagnetic coil and a permanent magnet secured to the back end of the energy application tool, for example, the tapping rod by an interface, for example, a coil mount. The coil, for example, an electromagnetic coil may lie axially behind the permanent magnet, for example. The electromagnetic coil may also act directly on a metallic or conductive component, such as a ferromagnetic component. Other forms of linear motors may also be employed.

Generally, the impact force made by the energy application tool, for example, a mechanical energy application tool, on the object undergoing measurement may vary depending on, for example, the mass of the tool, the distance traveled by the tool and the angle of incline of the device or tool with respect to the horizontal. For example, for a given mass of the tool, the impact force may be higher at minus 45 degrees, more for example, the impact force may be higher at about minus 30 degrees, than the impact force in a horizontal position, as gravity may contribute to the force at impact. Also, the impact force may be higher at a horizontal position than at plus about 45 degrees, more for example, the impact force at about plus 30 degrees, as gravity in the plus angle works against, rather than contributes to the impact force. Generally, a force of between 1-15 newtons may be used. Since the low end of impact force may not be optimal, the device may generally be placed in contact with the object undergoing measurement in a substantially horizontal position for better results, for example, by calibrating the system for the optimal amount of force exertion on the object. This may be rather restrictive in the ability to position the device. For example, some objects undergoing measurement may be in difficult to reach places and angling the device may be needed. Therefore, in some instances, a higher force may be used, for example, 10-50 newtons for may be used on a device to built-in some flexibility in positioning the device on an object. Even at this higher impact force range, the lower end, i.e. when the device is placed in an incline at a plus angle to the horizontal, may be lower than the impact force needed for generating an optimal measurement, while at the higher end, the force may be much higher than desired in some instances. However, this built-in capability of a higher force just in case there is a need to position the device at an angle to the horizontal may be undesirable when used in some situations, for example a dental setting, a delicate specimen situation, or to minimize disturbance to the object of any specimen. For example, impact force range of between about 20-45 newtons may need to be used, for example, in a dental setting, to obtain better results with some flexibility for positioning, and such force may be rather uncomfortable for the patient. The inventors of the present invention have invented a system that exerts a substantially the same impact force on the object in various angles from the horizontal, as if the device is operating horizontally. Thus, whether the device is operating at about plus/minus 45 degrees, more for example, about plus/minus 30 degrees from the horizontal, the device may still generate about the same amount of impact force, for example, about 20-30 newtons.

Similarly, for an energy application tool that is not a mechanical energy application tool, the force applied on the object may include electromagnetic energy or sound energy, such as ultrasound, and the amount of energy impacting the object may depend on the strength of the energy source, the distance traveled by the energy and the angle of incline of the device if the device is the energy application tool, or the energy tool with respect to the surface of the object to be impacted. Without wishing to be bound by any particular theory, it may be surmised that for a given strength, the impact force of the energy source may be higher if the impact surface of the object is perpendicular to the direction of force propagation than if the impact surface makes any other angle with the direction of force propagation and the impact force may be smallest if the surface of impact is parallel to the direction of force propagation. Since the low end of impact force may not be optimal, the device may generally be placed in contact with the object undergoing measurement in a substantially perpendicular position to the object surface for better results, for example, by calibrating the system for the optimal amount of force exertion on the object. This may be rather restrictive in the ability to position the device. For example, some objects undergoing measurement may be in difficult to reach places and angling the device may be needed. Therefore, in some instances, a higher force may be used, for example, an equivalent of 10-50 newtons may be used on a device to built-in some flexibility in positioning the device on an object. Even at this higher impact force range, the lower end range of the force, i.e. when the device is placed in an incline at a plus angle to the perpendicular direction, may be lower than the impact force needed for generating an optimal measurement, while at the higher end, the force may be much higher than desired in some instances. However, this built-in capability of a higher force just in case there is a need to position the device at an angle to the perpendicular direction may be undesirable when used in some situations, for example a dental setting, a delicate specimen situation, or to minimize potential damage to the object or any specimen. For example, an equivalent impact force range of may be higher than between about 20-45 newtons may need to be used, for example, in a dental setting, to obtain better results with some flexibility for positioning, and such force may be rather uncomfortable for the patient. The inventors of the present invention have invented a system that exerts a substantially the same impact force on the object in various angles from the perpendicular direction of the object surface, as if the device is operating so that the direction of propagation is perpendicular to the surface of the object. Thus, whether the device is operating at about plus/minus 45 degrees, more for example, about plus/minus 30 degrees from the perpendicular direction with respect to the object surface, the device may still generate about the same amount of an equivalent impact force, for example, about 20-30 newtons.

In addition, the ability to position the tool at various angles from the horizontal may be advantageous for energy source not of a mechanical type, for example sound energy such as ultrasonic, or electromagnetic, responses that are not well defined or noisy from one angle may be more defined or pronounced from another angle such that any defects close to the surface that may be affecting the measurements at one angle may not be affecting the measurement from another angle may even produce better and more complete results of the properties of the object. Also, defects at the surface that may complicate the measurement, for example, by deflecting the response in a direction not sense by the sensor may become detectable and within the range of the sensor if another direction of impact is made.

An inclinometer may be present, for example, on the device, which may trigger an audible warning when the device is held against the object and is outside of the angular range of operation, for example, for a tapping rod, it may be set to trigger the warning when it is plus/minus approximately 45 degrees, more for example, plus/minus about 30 degrees from the horizontal, at which point, the angle may substantially affect the result of the measurement of the object, if desired. In one embodiment, for a mechanical energy application tool, if the device is oriented such that the axis of operation is greater than about 45 degrees, more for example, greater than about 30 degrees from the horizontal position, and the device is activated when a contact force is sensed on the object contacting portion of the sleeve portion on the object, it may result in a warning sound being emitted by a speaker located on the device, such as the printed circuit board (PCB) within the device. In another embodiment, the warning sign may be given by a light signal, which may be a flashing light, or a light of a certain color. In such circumstances, the percussion action, if the device is a percussion instrument, will not begin until the device is returned to an acceptable angle. In some instances, if the percussion action has started when the above-mentioned departure from the range is detected, the device may not actually stop operation, but may simply be sounding an alarm, so that corrections may be made. Similar set up may be included for other types of energy application tools and the angles may be with respect to the perpendicular direction of the contact surface. As mentioned above, the system and method of the present invention is non-destructive and non-invasive, and may include a device capable of operating by holding the device at varying angles from the horizontal and modulating the energy application process to mimic a substantially horizontal position during measurement. The system may or may not include disposable parts and/or features for aiding in repositionability. The present system and method for measuring structural characteristics may minimize impact, even minute impact on the object undergoing measurement, without compromising the sensitivity of the measurement or operation of the system. When the energy application tool is a tapping rod, the amount of impact energy may also vary dependent on, for example, the length of the rod, the diameter pf the rod, the weight of the rod or the velocity of the rod prior to impact, so on. In one embodiment, the system includes an energy application tool that is light weight and/or capable of moving at a slower velocity such that it minimizes the force of impact on the object during measurement while exhibiting, maintaining or providing equivalent or better sensitivity of measurement. In one aspect, the energy application tool, for example, the tapping rod, may be made of lighter material to minimize the weight of the handpiece and thus may minimize impact on the object undergoing measurement. In another embodiment, the energy application tool, for example, the tapping rod, may be made shorter and/or of smaller diameter such that the size of the handpiece may also be minimized and thus may minimize impact on the object undergoing measurement. In a further embodiment, the system may include a drive mechanism that may lessen the acceleration of the energy application tool and thus may minimize impact on the object undergoing measurement. For example, the drive mechanism may include a smaller drive coil to lessen the acceleration of the energy application tool, whether or not it is light weight, and/or smaller in length or diameter, and minimizes the impact force on the object during operation while maintaining sensitivity of measurement. These embodiments may be combined with one or more of the embodiments described before or below, including the lighter weight handpiece housing. The speed of conducting measurement may also be desirable without increasing the initial velocity of impact so as to minimize impact on the object during measurement. The system may or may not have disposable parts and/or features for aiding in repositionability mentioned above or below.

In any of the systems mentioned above or below, including all the exemplary embodiments, either with or without lighter weight energy application tool, a shorter or smaller diameter energy application tool, or a drive mechanism that may include a smaller drive coil to lessen the acceleration of the energy application tool, if the measurement is to be made while a portion of the sleeve is in contact with the object, the force an operator exerts on the object may also be important and may need to be monitored, since, for example, either insufficient or excessive force exerted by an operator may complicate the measurements, and may even produce less accurate results, in addition to the activation feature, as noted above. The system may or may not have disposable parts and/or features for aiding in repositionability and/or lessening impact with features mentioned below.

Upon activation of, for example, a mechanical energy application tool, for example, the pressing of a finger switch on the device, a magnetic coil within the device propels the energy application tool, such as a tapping rod to extend at a speed towards an object undergoing measurement and strike or impact the object or specimen, for example, multiple times per measuring cycle with an impact force. The impact force on the object may create stress waves that traveled through the energy application tool, such as the tapping rod and the deceleration of the tool such as the tapping rod upon impact with the object may be measured by a measuring or sensing device or mechanism located in the device and transmitted to the rest of the system for analysis. The system may measure, for a time interval, a percussion response such as energy reflected from the object as a result of the energy application, for example, by tapping or applying energy, which may include creating a percussion response profile, for example, a time-energy profile, frequency-energy profile, based on the energy reflected from the object during the time interval, and/or evaluating the percussion response profile, for example, time energy profile to determine the damping capacity of the object or other characteristics. The measuring device or sensing mechanism may detect characteristics of the effects from the impact of the energy application tool with the object. In general, the measuring device or sensing mechanism may be physically coupled to, functionally coupled to or otherwise in contact with the energy application tool such that it may detect characteristics of the impact. The coupling may be wired or wireless.

In some embodiments, the measuring device or the sensing mechanism utilized for analysis of the object may include sensors for sensing and/or measuring the response either form the object or the energy application tool during measurement. In one aspect, the drive mechanism may include a sensing and/or measuring device, for example, a piezoelectric force sensor, or a piezoelectric sensing element, located within the housing for coupling with the energy application tool, such as the tapping rod and may generally produce an electrical signal or change in response to mechanical energy, such as a change in pressure on the piezoelectric sensing element. A piezoelectric wire may also, for example, be loaded into the energy application tool. The measuring device may be adapted, for example, for measuring the deceleration of the tapping rod upon impact with an object during operation, or any vibration caused by the tapping rod on the specimen. The piezoelectric force sensor may detect changes in the properties of the object and may quantify objectively its internal characteristics. Data transmitted by the piezoelectric force sensor may be processed by a system program, to be discussed further below. In another aspect, the measuring device or sensing mechanism may also include other forms of sensing elements, such as, for example, a linear variable differential transformer adapted for sensing and/or measuring the displacement of the energy application tool such as the tapping rod, before, during and after the application of energy. The linear variable differential transformer may be a non-contact linear displacement sensor. The sensor may utilize inductive technology and thus capable of sensing any metal target. Also, the noncontact displacement measurement may allow a computer to determine velocity and acceleration just prior to impact so that the effects of gravity may be eliminated from the results. In other aspects, the sensing and/or measuring device may sense the position of the energy application tool due to changes in voltage in the transformer due to positioning of the energy application tool which may be metal or otherwise affect the induction in the transformer, accelerometers, resistive pressure sensors, strain gauges, and/or any other appropriate type of sensor or combination of sensors. For example, an accelerometer within the device coupled with the energy application tool may measure signals corresponding to the resulting stress waves. Data transmitted by the accelerometer is processed by a calibrated computer program which detects changes in the properties of the specimen and quantifies objectively internal characteristics. In general, the sensing mechanism for detecting the characteristics of the effects of the energy application tool may be separate from sensing of the contact force between the handpiece (such as through the sleeve portion) with the object.

After impact with the object, the energy application tool, for example the tapping rod, decelerates, as noted above. The deceleration of the energy application tool, for example a tapping rod, may be measured by a measuring device or sensing mechanism, for example, an accelerometer inside the device. For example, the accelerometer within the device coupled with the energy application tool may be adapted for measuring the deceleration of the energy application tool upon impact with an object during operation, the percussion response from the object, measuring any vibration caused by the impact or measuring signals corresponding to the resulting stress waves. The measuring device or sensing mechanism may detect changes in the properties of the object and may quantify objectively its internal characteristics. Data transmitted by the measuring device or sensing mechanism may be processed by a system program, as noted before or below.

The above described measuring mechanism may also be applicable to other than mechanical energy application tools described above, with similar sensor set up, for example, when such energy application tools perform a percussion action.

The energy application tool, such as the tapping rod, may be programmed to strike an object a certain number of times per minute at substantially the same speed and the deceleration information may be recorded or compiled for analysis by the system. The sleeve portion, in addition to aiding in positioning the device, may also aid in attenuating any vibrations caused by the impact so as to not disturb the sensitive measurements, if it is of a material having some damping properties.

For electromagnetic energy, the energy application may be in the form of pulses or energy bursts which may be programmed to impact an object a certain number of times per minute with substantially the same amount of energy each time and the effect on the object may be recorded or compiled for analysis by the system. In some instances, the repeated impact may provide an average measurement that may be better representative of the actual underlying property. The sleeve portion, in addition to aiding in positioning the device, may also aid in attenuating any vibrations caused by the impact so as to not disturb the sensitive measurements, if it is of a material having some damping properties.

In some embodiments, the inclinometer may include an accelerometer, such as a 3-axis device which measures gravity on all three axes, the X, Y and Z axes. In one embodiment of the invention, the device, such as a handpiece, may include software for measuring the value of the Y-axis (i.e. vertical) gravitational force (G-force). For example, if the G-force for the Y-axis is greater than about the plus/minus, say, 15 degrees threshold, the handpiece may make an audible noise, such as beeps, or a light signal such as a flashing light, or a light of a certain color. If the G-force for the Y-axis is greater than the 30-degree threshold, the handpiece may beep faster, or if a light signal such as a flashing light, it may be a faster flashing light. The accelerometer may be sampled every, say, 100 ms. Five consecutive valid readings may be needed (500 ms) to trigger a threshold and thus the beep or the flash, etc. The thresholds for both the 15 and 30-degree thresholds may be determined empirically.

For example, for a device without the features of the present invention, during operation, if the equivalent impact force is about 26 newtons at plus 15 degrees from the horizontal, the equivalent impact force may be about 32 newtons at a horizontal position, and at minus 15 degrees from the horizontal, the impact force may be about 35 newtons. With the present invention, all impact forces at all the above-mentioned angles may be at about 25 newtons or whatever optimal impact force programmed to exert. This may be accomplished by, for example, varying the application of energy from the drive mechanism to the energy application tool to accommodate the angle of impact. Examples of variations to the application of energy from the drive mechanism, such as an electromagnetic coil, may include varying the power applied to the coil (e.g. varying voltage, current or both), coil drive times (varying the length of time the coil is energized or activated), coil delay times (varying the time between driving activities), number of coil energizations (i.e. varying the number of drive pulses applied), polarity of the coil and/or a combination thereof. These factors, including varying power, drive times, polarity and delay times may be managed through varying the firmware settings for power, drive time, number of drives, polarity and drive delay of the energizing of the coil for the desired results. Without wishing to be bound to any particular theory, it is surmised multiple variations may be employed to achieve the desired result and the firmware may be designed to select a particular solution or to select an optimal solution for certain instances.

In some embodiments, the firmware may be adapted to vary only certain settings of the drive mechanism, such as, for example, drive times, number of drives, polarity and drive delays, while keeping other settings constant, such as, for example, power. This may be desirable as some settings may be more difficult to adjust, such as power settings which may be relatively unadjustable due to a particular power source, such as a battery.

As noted above, the system may be turned on and off with or without an external switch, or remote control. In one embodiment, the energy application process of the handpiece may be triggered via a mechanical mechanism, such as by a switch mechanism. In one aspect, a finger switch may be located at a convenient location on the handpiece for easy activation by the operator. In another aspect, the switch mechanism may be triggered by applied pressure to the object through the sleeve. In another embodiment, the energy application process of the handpiece may be triggered via voice control or foot control.

Generally, any external switching device such as a flip switch, a rocking switch or a push button switch, may tend to restrict the manner an operator holds the instrument and thus may restrict the positioning of the instrument on the object, if it is handheld, for example, during measurement so as to enable easy access by the operator to the switching device for turning it on and/or off.

In one embodiment, to gain more flexibility in positioning the instrument, voice control or remote control may generally be used, though such voice controls or remote controls can add complexity to the system. In the present invention, the same advantages of flexibility may be gained without such remote controls or added complexities.

In another embodiment, to gain more flexibility in positioning the instrument, activation of the device may be controlled by a proper contact force between the object and a sleeve portion located at the open end of the housing, as noted above and below. This proper contact force may also add other desirable features to the system, as discussed below. The sleeve portion may be open at its free end, with an object resting, pressing or contacting portion for resting on, pressing or contacting at least a portion of an object during measurement. The contact by the sleeve portion aids to stabilize the device on the object. During measurement, the force exerted by the sleeve portion on an object is controlled by an operator, unlike the impact force of the energy application tool, which may be controlled by the various factors of the system described above, and a proper contact force on the object may be important and may need to be monitored, since, for example, either insufficient or excessive force exerted by an operator may complicate the measurements, and may even produce less accurate results. A sensor disposed inside the housing, not physically or mechanically coupled to the energy application tool may be present to ensure that a proper contact force by the contacting portion of the sleeve portion may be applied by the operator for better reproducibility, even by different operators.

The sleeve portion may be mounted onto a force transfer sleeve-like component, or force transfer member, that forms a permanent part of the front of the housing or protrudes from it, and shields the energy application tool, for example, the tapping rod from damage when no sleeve portion is present, for example, the sleeve portion may form part of a disposable assembly, as discussed below. The force transfer sleeve-like component sits around the energy application tool, or rod, for example, it may surround the energy application tool, and is held at the front by the housing and mounts onto the front of the electromagnetic coil at the rear. The force transfer sleeve-like component may be adapted to slide a small amount, and in doing so, may act on a force sensor, for example, a force sensitive resistor, piezoelectric sensor, strain gauge(s), etc., located between the back surface of the force transfer sleeve-like component and a relative fixed position, such as the coil mount or mounting bracket for the drive mechanism. The energy application tool, for example the tapping rod may be triggered when the object contacting portion of the sleeve portion is pushed against an object undergoing measurement, for example, a tooth and a force may be detected. When a correct force within a certain range is detected, the instrument is turned on to start the measurement. Linear position measurements by sensors may also be utilized to detect the contact force.

The sensor, for example the force sensor, may be disposed anywhere inside the housing and be in physical proximity and/or contact and/or coupled with at least a portion of the device other than the energy application tool, for example, it may be in physical proximity and/or contact and/or coupled with the housing and/or sleeve portion, if the open end of the sleeve portion includes an object contacting portion, as noted above. In one embodiment of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. In another embodiment of the invention, the sensor may include a sensing pad which may be positioned between a rigid surface and a sliding part so that when the pad is pressed or squeezed as the sliding part moves towards the rigid surface, the force is measured. According to one embodiment, the rigid surface may be, for example, a coil interface that holds the electromagnetic coil in the drive mechanism within the device housing. The sliding part may be a force transfer sleeve-like component disposed inside the housing and coupled to the object contacting portion of the sleeve portion and adapted to slide inside the housing when a force is exerted by the object contacting portion of the sleeve portion on an object. In some embodiments, it may be disposed inside the sleeve portion. The sliding distance may be very small, for example, in the order of about (in millimeters or mm) 0.3 mm to about 1 mm, more for example about 0.5 mm. The sensing pad may include a layer structure, which may be generally referred to as a "Shunt Mode FSR (force sensing resistor) that may change resistance depending on the force applied to the pad, to provide a force measurement. According to another embodiment, the force transfer sleeve-like component may be biased forward by a spring, so that when force is applied by the object contacting portion of the sleeve portion on the object, the force transfer sleeve-like portion may transfer the force against the spring. According to one aspect, the force sensing may be done by a linear position sensor, which would know, for example, that if the force transfer sleeve-like portion is at position X, a force of Y has to be applied to it (against the reaction force of the spring) to move it to that position. According to another aspect, the force sensing may be performed by an optical sensor, for optically sensing the position of the moving part, when it is pushed against a spring. In yet another embodiment of the invention, the relative position of the object contacting portion of the sleeve portion on the object may be determined by having one or more strain gauges which may be attached at one end to a moving part, for example, the force sensor sleeve-like component, and the other end to a static element, for example, the housing. In a further embodiment of the invention, the device may include piezoelectric elements for directly measuring the force. In yet a further embodiment of the invention, a hall effect sensor may be used to detect a change in the magnetic field when a magnet (attached to the moving element) is moving relative to the position of the sensor. In yet another embodiment of the invention, a capacitive linear encoder system, like that found in digital calipers may be used to measure the force.

The force transfer sleeve portion may or may not be in one single piece. When present in one single piece, it may aid in rigidizing the drive mechanism, for example, the drive train. The rigidized drive train may minimize effect of external force, for example, when the device may bump against the inside of the oral cavity during measurement, which may disturb the path of the energy application tool.

As noted before, the force sensor may be positioned anywhere inside the housing, as long as it is not in physical proximity and/or contact and/or coupled to the energy application tool. In one embodiment, it may be located closer to the front of the housing towards the sleeve portion. In another embodiment, it may be located towards the rear of the housing. In a further embodiment, the force sensor may be positioned towards the middle of the housing. When the force sensor is positioned towards the rear of the housing, the positioning may better facilitate the rigidization of the driver mechanism discussed above than when the force sensor is present in other locations. In general, no matter where the force sensor is located, if the energy application tool is a tapping rod, the rod may pass through the sensor and the force transfer sleeve, i.e., the force sensor and/or the force transfer sleeve may surround the energy application tool.

Though the sensor is not physically or mechanically coupled to the energy application tool, it may be in electronic communication with the energy application tool and may act as an on/off switch for the device or instrument, as noted above. For example, when a proper force is exerted on the object by the object contacting portion of the sleeve, it may trigger the activation mechanism of the device or instrument to activate the movement of the energy application tool to start a measurement. Thus, no external switches or push buttons are needed to activate the on and off of the system, as noted above. The indication of the proper force may be indicated by visible or audible signals.

In one embodiment, the instrument may be instantaneously turned on once a proper contact force is exerted by the object contacting portion of the sleeve on the object, as indicated by visible or audible signals. In another embodiment, there may be a delay prior to turning on the instrument once a proper contact force is exerted by the object contacting portion of the sleeve on the object, as indicated by visible or audible signals. In a further embodiment, once a certain push force between the object contacting portion of the sleeve portion and the object is detected and maintained for a period of time, for example, about 1 second, more for example. about 0.5 seconds, the instrument may be turned on to start measurement, In this embodiment, a green light lights up the tip, and percussion will begin approximately 1 second, more for example, 0.5 seconds after a force in the correct range is maintained.

The proper force exerted by the operator on the object, for example, through the sleeve portion, acts as a switch of the system. When the system is not switched on, it may be desirable to know whether it has malfunction, not sufficient force or too much force is exerted. In one embodiment, the force measurement may be connected to a visual output, such as lights. Lights may be mounted at any convenient location on the device or instrument, for example, one or multiple LEDs may be mounted at the front of the device or instrument. In one aspect, a multiple light system may be included. For example, two LEDs may be used. When the force is in the correct range, the green light may be lit. If too much force is detected, the LEDs may change to red, and the instrument will not work unless the push force is reduced. In some embodiments, if the user is pushing too hard on the object, the light may change first to amber, then to red. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another aspect, no light may indicate too little force, a green light may indicate the right amount of force, while a red light may indicate too much force. In yet another aspect, a one light system may be included. For example, no light may give a signal of too little force and a red light may give a signal of too much force. In a further aspect, a flashing red light may indicate too much force and no light may indicate too little force.

In another embodiment, the force measurement may be connected to an audible output. In one aspect, the audible output may include a beeping sound to indicate too little force and a multiple beep to indicate too much force. In another aspect, the audible output may include a beeping sound to indicate too little force and a beeping sound with a flashing red light to indicate too much force. In a further aspect, the force measurement may be connected to a voice alert system for alerting too much force or too little force. In yet a further aspect, the force measurement may be connected to a voice alert system to alert too little force and a voice alert and a flashing red light for alerting too much force.

When the force sensor acts as an on/off switch, it may also act to monitor that a proper force is exerted by the object contacting portion of the sleeve portion during measurement and/or a proper alignment of the object contacting portion of the sleeve portion against the object during measurement is obtained. An inclinometer may be present, for example, as part of an electronic control system, which may trigger an audible warning when the device is outside of the angular range of operation, for example, for a mechanical energy application tool such as a tapping rod, it may trigger the warning when it is outside the plus/minus approximately 45 degrees range, more for example, may be programmed to warn when outside the plus/minus approximately 30 degrees range from horizontal. Thus, if the device is oriented such that the axis of operation is greater than about plus/minus 45 degrees, more for example, greater than about plus/minus 30 degrees from horizontal when a push force is sensed on the object contacting portion of the sleeve portion, it may result in a warning sound being emitted by a speaker located on the device, such as the printed circuit board (PCB) within the device. In such circumstances, the percussion action will not begin until the device is returned to an acceptable angle. In some instances, if the percussion action has started when the above-mentioned departure from the range is detected, the device may not actually stop operation, but may simply be sounding an alarm, so that corrections may be made.

The energy application tool has a length with a resting configuration and an active configuration. The movement may be axial movement along the longitudinal axis of the housing, or for oscillatory movement about the longitudinal axis of the housing, as discussed above.

In one embodiment, the sleeve portion may attach and/or surround at least a length of the free end of the housing and protrudes from the housing for a distance substantially coextensive with the end of the energy application tool, for example, the tapping rod in its extended form if the tapping rod moves axially. Thus, the length of the sleeve portion in this embodiment may be somewhat dependent on the length of protrusion of the extended tapping rod desired. The free end of the sleeve may be placed against an object undergoing measurement. The contact by the sleeve portion on the object helps to stabilize the device on the object, as noted above. In another embodiment, the sleeve portion may be attached to the end of the housing and being substantially perpendicular to it when the energy application tool, for example, the tapping rod moves from being substantially parallel to making an acute angle with the longitudinal axis of the housing at a pivot when in operation. The sleeve portion may be substantially cylindrical in shape. In a further embodiment, the sleeve may be an extension of the housing and being of substantially a half cylindrical shape to allow the energy application tool, for example, the tapping rod to freely move when the tapping rod moves from being substantially parallel to making an acute angle with the longitudinal axis of the housing in operation. Using this system, measurements may be undertaken at locations which are relatively inaccessible such as, for example, in the molar area of a patient's teeth.

Similarly, for other than mechanical energy application tool, it is surmised that the above may also be applicable, and instead of a mechanical energy application tool such as a tapping rod, an energy source, such as an electromagnetic energy or sound energy source may reside inside the housing. Instead of extending and retracting, the source may simply be turned on and off. A sleeve portion may also be present.

In another exemplary embodiment, any of the systems described above or below may also include disposable features for aiding in eliminating or minimizing contamination of the object undergoing the measurement through transfer from the system or cross-contamination from previous objects undergoing the measurements, without interfering with the measurement or the capability of the system. The disposable feature may include any of those described below or as disclosed in U.S. Pat. No. 9,869,606, or WO2011/160102A9, entitled "System and Method For Determining Structural Characteristics Of An Object", the contents of which is hereby incorporated by reference in its entirety.

The present invention also relates to a system and method for measuring structural characteristics in a non-invasive manner and/or using a non-destructive method of measurement, including a device capable of operating by holding the device at varying angles from the horizontal and modulating the energy application process to mimic a substantially horizontal position during measurement, and using an energy application tool that includes disposable features for aiding in eliminating or minimizing contamination of the object undergoing the measurement through transfer from the system or cross-contamination from previous objects undergoing the measurements, without substantially interfering with the measurement or the capability of the system. The instrument includes a housing having a hollow interior with an open end and an energy application tool, for example, a tapping rod, or impact rod mounted inside the housing for movement inside the housing. The housing has a longitudinal axis and the energy application tool has a length with a resting configuration and an active configuration. and the longitudinal axis of the device may be positioned at any angle with the horizontal direction. The angle may be, for example, of any angle, more for example, vary from zero degrees to about plus/minus forty-five degrees., even more for example, vary from zero degrees to about plus/minus thirty degrees. The different embodiments of the system and method described above without the disposable features are also applicable here. The system provides a non-destructive method of measurement with some contact with the object undergoing such measurement without the need for wiping or autoclaving of the energy application tool, such as a mechanical tool, an electromagnetic or sound energy source, and at the same time without disposing of the energy application tool and/or the housing and whatever may be housed inside the housing of the instrument. The drive mechanisms described above for modulating the energy application process to mimic a substantially horizontal position during measurement are also applicable to this system and method.

In one exemplary embodiment, the housing has a longitudinal axis and the energy application tool has a length, if a mechanical energy application tool is used, with a resting configuration and an active configuration, or on and off configuration for other types of energy application tools. The housing includes a sleeve portion extending therefrom. The sleeve portion is open at its free end, and has an object resting or contacting portion for resting on, pressing or contacting an object just prior and during measurement.

The mechanical energy application tool is driven by a drive mechanism. The drive mechanism may be an electromagnetic mechanism, and may include an electromagnetic coil and a permanent magnet secured to the back end of the energy application tool, for example, the tapping rod. The electromagnetic coil may lie axially behind the permanent magnet, for example. For other energy application sources, an input power drives the energy application tool.

The energy application tool has a length with a resting configuration and an active configuration. The movement may be axial movement along the longitudinal axis of the housing, or for oscillatory movement about the longitudinal axis of the housing, as discussed above.

The disposable feature may include a sleeve portion extending from and/or enveloping the open end of the housing. In one example, for a mechanical energy application tool, the sleeve portion includes a hollow interior and an open free end with an object resting or contacting portion for resting on, pressing or contacting an object during measurement at its open end. A feature such as a contact feature having a length and disposed towards the open end of the sleeve portion, fits snuggly inside the sleeve portion, for example, by friction. The contact feature may be, for example, a short tubular section, or a ring, and is adapted for freely moving or sliding inside the sleeve portion, substantially along the longitudinal axis of the sleeve portion, and may include a closed end for substantially closing the off the free end of the sleeve portion. The contact feature may be positioned in between the tip of the energy application tool and the surface of the object undergoing measurement and by being freely moving or sliding, may adjust itself to various surface configurations of an object undergoing measurement. The freely moving or sliding contact feature may vary in size and/or otherwise be adapted to move a desired predetermined distance along the longitudinal axis of the sleeve portion. In some examples, such as for a ring-shaped contact feature, movement stops, such as small ridges, stops or other obstacles, may be present inside the sleeve portion to prevent sliding or movement inside the sleeve portion outside of a desired range. For example, at least a portion of the closed end may be in the proximity of the surface of the object, and may or may not be in contact with the surface of the object just prior to impact by the energy application tool on the contact feature. During impact by the energy application tool on the closed end of the contact feature, at least a portion of the outside surface of the closed end or object contacting surface of the closed end of the contact feature is in close contact with the surface of the object. Thus, if at least at portion of the object contacting surface of the closed end is contoured to mirror the surface of the object it comes into contact with, the better contact with the object is made and energy transfer from the impact by the energy application tool may not be substantially impaired. In one aspect, the closed end of the contact feature may include at least a portion that may have a substantially flat portion facing the object to substantially mirror a flat surface of an object. In another aspect, the closed end of the contact feature may include at least a portion that may be contoured to mirror the surface of an object it comes into contact with if the object surface is contoured. For an example, if the surface of the object undergoing measurement includes a depression, the contact feature may include a closed end having a concave outside surface to substantially mirror the depression so as to adjust itself to maintain contact between the closed end and the object during impact. For another example, if the surface of the object includes a bump, the contact feature may include a closed end having a convex surface to substantially mirror the bump so as to maintain contact with the object during measurement. In a further aspect, the closed end may possess some elasticity or be deformable, so that close contact with the object may be achieved during impact.

In general, the contact between the object and at least a portion of the closed end of the contact feature, though the contact feature is freely moving, may nevertheless help to stabilize the device on the object and/or may improve the reproducibility of the measurements.

In other embodiments, the contact feature may not be movable. For example, the contact feature may be fixed to the front opening in the sleeve portion and acts as an intermediate member between the object and the energy application tool during measurement so that there is no direct contact between the tip of the energy application tool and the object.

For non-movable energy application tools, the sliding portion may or may not be present and the contact feature may be stationary or fixed. A non-movable but conformable contact feature may have the same advantages of a movable contact feature, as noted below.

In one embodiment of the invention, during a measurement, the closed end of the contact feature may be conformable or movable and may adjust itself to the surface configuration of the object and the object contacting portion of the open end of the sleeve properly contacts the object. The sensor described above, if present, senses and/or monitors that a proper contact force is exerted by the sleeve portion on the object. The energy application tool, for example, the tapping rod, taps the object indirectly through the closed end of the contact feature repeatedly during a measurement.

In another embodiment of the invention, during a measurement, the closed end of the contact feature may be conformable or movable and adjusts itself to the surface configuration the object and the object contacting portion of the open end of the sleeve properly contacts the object, however, a portion of the closed end may extend beyond the sleeve to contact an irregular surface of the object simultaneously. The sensor described above, if present, senses and/or monitors that a proper contact force is exerted by the sleeve portion on the object. The energy application tool, for example, the tapping rod, taps the object indirectly through the closed end of the contact feature repeatedly.

The movable contact feature may be of any shape as long as it fits snuggly and yet freely moving or sliding inside the sleeve portion with a closed end substantially closing off the free end of the sleeve. As noted above, in embodiments where movable or slidable may not be necessary, the contact feature may be conformable. It may be constructed of any material that may be molded or cast and may include polymers or filled polymeric material. For light weight, it may also be thin but of sufficiently stiffness to facilitate the sliding action. In some embodiments, it may have a conformable closed end or front portion.

The contact feature may also include a thin membrane at its closed end. The membrane may be attached or integrally bonded to the rest of the contact feature. The membrane may also be a thicker membrane in a non-movable contact feature. Whether the membranes are thick or thin is not relevant, as long as they are chosen to have a minimal effect on the operation of the energy application tool. In one aspect, the membrane may possess some elasticity or deformability for better contact between the membrane and the object when struck by the energy application tool, as noted above, but may still be capable of transferring the impact force exerted by the energy application tool to the object. In another aspect, the membrane may be of any material that enables better transfer of impact force between it and the object.

In one embodiment, the closed end may include a thin polymeric membrane, which may or may not be of the same material as the rest of the contact feature, or it may be a material having substantially the same properties as the rest of the contact feature. The polymer may include any polymeric material that is capable of being molded, cast or stretched into a thin membrane so that it does not substantially adversely affect the measurement. In another embodiment, the closed end may include an insert molded metal foil membrane. The metal may be any metallic material that may be drawn, cast or molded into a thin membrane so that it does not substantially adversely affect the measurement. In other embodiments, the closed end may be integral to the contact feature. For example, the contact feature may be formed from a material which may be shaped into a tubular or ring structure with a closed end of a desired thickness, such as by stamping a metal (e.g. stainless steel, aluminum, copper, or other appropriate metal).

In another exemplary embodiment, the housing has a longitudinal axis and the energy application tool has a length with a resting configuration and an active configuration. and the longitudinal axis of the device may be positioned at any angle with the horizontal direction. The angle may be, for example, of any angle, more for example, vary from zero degrees to about plus/minus forty-five degrees., even more for example, vary from zero degrees to about plus/minus thirty degrees. The housing may or may not include a sleeve portion extending therefrom and has an open end at its free end.

The energy application tool has a length with a resting configuration and an active configuration. The movement may be axial movement along the longitudinal axis of the housing, or for oscillatory movement about the longitudinal axis of the housing, as discussed above.

The disposable feature may include a covering for enveloping a part of the system that may come into proximity and/or contact with the object undergoing the measurement without interfering with the sensitivity, reproducibility, if desired, or general operation of the instrument to any substantial degree.

The disposable feature may be applicable to all other types of energy application tools, as noted before.

The covering may include a portion extending from and/or enveloping the open end of the housing, or the sleeve portion, if a sleeve portion extends from the housing. A contact feature having a length, and disposed towards the open end of the housing or sleeve portion may fit snuggly inside the housing or sleeve portion, by friction, and may extend beyond the open end of the housing or sleeve portion, if one is present. The contact feature includes a closed end for closing the free end of the housing or sleeve portion, if one is present. The closed end of the contact feature comes in between the tip of the energy application tool and the object, and a portion of the surface of the closed end of the contact feature comes into contact with at least a portion of the surface of the object undergoing measurement. In this exemplary embodiment, the end of the housing or sleeve portion may not come into contact with the object during measurement. The contact feature is adapted for be freely moving or sliding inside the housing or sleeve portion, if one is present, or may be slightly restricted to a predetermined distance of movement, and does not completely retract inside the housing or sleeve portion. The contact feature may include a closed end for substantially closing the free end of the housing or sleeve portion, if one is present. The stabilization of the device against an object undergoing measurement may be effected by the contact of at least a portion of the outside surface of the closed end of the contact feature on at least a portion of the surface of the object.

For non-movable energy application tools, the sliding portion may or may not be present and the contact feature may be stationary or fixed, though there are advantages of having a movable or at least a comfortable contact portion, as noted below.

Here also, the contact feature is positioned in between the tip or end of the energy application tool and the surface of the object undergoing measurement and by being conformable or freely moving or sliding, may adjust itself to various surface configurations of an object undergoing measurement. For example, at least a portion of the closed end may be in contact with the surface of the object, prior to impact by the energy application tool on the contact feature. During impact by the energy application tool on the closed end of the contact feature, at least a portion of the outside or object contacting surface of the closed end remains in close contact with the surface of the object. Thus, if at least at portion of the object contacting surface of the closed end may be contoured to mirror the surface of the object it comes into contact with, the better contact with the object is made and energy transfer from the impact by the energy application tool may be not be impaired. In one aspect, the closed end of the contact feature may include at least a portion that may have a substantially flat portion facing the object to substantially mirror a flat surface of an object. In another aspect, the closed end of the contact feature may include at least a portion that may be contoured to mirror the surface of an object it comes into contact with if the object surface is contoured. For an example, if the surface of the object undergoing measurement includes a depression, the contact feature may include a closed end having a concave surface to substantially mirror the depression so as to adjust itself to maintain contact between the closed end and the object during impact. For another example, if the surface of the object includes a bump, the contact feature may include a closed end having a convex surface to substantially mirror the bump so as to maintain contact with the object during measurement. In a further aspect, the closed end may possess some elasticity or may be deformable, so that close contact with the object may be achieved during impact.

For example, during a measurement, the closed end of the contact feature may adjust itself to the surface configuration of the object and stays in contact with the surface of the object. The energy application tool, for example, the tapping rod, taps the object indirectly through the closed end of the contact feature repeatedly.

The contact feature may be of any shape as long as it fits snuggly and yet free moving or sliding, for a predetermined length, if desired, inside the housing or sleeve portion, if one is present, or just being conformable, with a closed end closing the free end of the housing or the sleeve portion, as discussed above. The contact feature may be of any appropriate length, such as, for example, a short tubular section, or a ring, and is adapted for freely moving or sliding inside the sleeve portion, substantially along the longitudinal axis of the sleeve portion, and may include a closed end for substantially closing the off the free end of the sleeve portion. The contact feature may be positioned in between the tip of the energy application tool and the surface of the object undergoing measurement and by being freely moving or sliding, may adjust itself to accommodate various surface configurations of an object undergoing measurement. The distance of movement for the contact feature may vary, and in some instances may be of a predetermined distance. In some examples, such as for a ring-shaped contact feature, movement stops, such as small ridges, stops or other obstacles, may be present inside the sleeve portion to constrain the movement of the contact feature within the sleeve portion.

Whether the contact feature is movable or not and the membranes are thick or thin is not relevant, as long as they are chosen to have a minimal effect on the operation of the energy application tool. In one aspect, the membrane may possess some elasticity or deformability for better contact between the membrane and the object when struck by the energy application tool, as noted above, but may still be capable of transferring the impact force exerted by the energy application tool to the object. In another aspect, the membrane may be of any material that enables better transfer of impact force between it and the object. It may be constructed of any material that may be molded or cast and may include polymers or filled polymeric material. As noted above, in embodiments where movable or slidable may not be necessary, the contact feature may be conformable. In some embodiments, it may have a conformable closed end or front portion.

For light weight, it may also be thin but of sufficiently stiffness to facilitate the sliding action. In some embodiments, it may have a conformable closed end or front portion.

The contact feature may include a thin membrane at its closed end such that it will not substantially affect the measurement. The membrane may be attached or integrally bonded to the rest of the contact feature. The membrane may be chosen to have a minimal effect on the operation of the energy application tool. In one aspect, the membrane may possess some elasticity or deformability for better contact between the membrane and the object when struck by the energy application tool, but still capable of transferring the impact force exerted by the energy application tool to the object. In another aspect, the membrane may be of any material that enables better transfer of impact force between it and the object.

In one embodiment, the closed end may include a thin polymeric membrane, which may or may not be of the same material as the rest of the contact feature, or it may be a material having substantially the same properties as the rest of the contact feature. The polymer may include any polymeric material that is capable of being molded, cast or stretched into a thin membrane so that it does not substantially adversely affect the measurement. In another embodiment, the closed end may include an insert molded metal foil membrane. The metal may be any metallic material that may be drawn, cast or molded into a thin membrane so that it does not substantially adversely affect the measurement. The membrane may also be formed to conform to the shape of the energy application tool, or vice versa, for optimal transfer of force/energy. In some embodiments, the membrane may be constructed from stainless steel foil or sheet, and may, for example, be stamped and/or molded. In other embodiments, the closed end may be integral to the contact feature. For example, the contact feature may be formed from a material which may be shaped into a tubular or ring structure with a closed end of a desired thickness, such as by stamping a metal (e.g. stainless steel, aluminum, copper, or other appropriate metal).

For these exemplary embodiments, the force sensor described above, including all aspects of its features, may or may not be present, for sensing and/or monitoring that a proper force is exerted by the object contacting portion of the sleeve portion or the closed end of the contact feature on the object, and/or for activating the system to start measurement when a proper force is exerted.

For a device of any of the exemplary embodiments described herein, having a force sensor for sensing or monitoring a force exerted by either the object contacting surface of the sleeve portion or the contact feature, the force sensor may be in physical proximity and/or contact with at least a portion of the device other than the energy application tool, for example, the sleeve portion or at least a portion of the sleeve portion, if the open end of the sleeve portion includes an object contacting portion, or at least a portion of the housing, if no sleeve portion is present, as exampled before in relationship to other exemplary embodiments.

The sensor, for example a force sensor, may be in physical proximity and/or contact and/or coupled with at least a portion of the device other than the energy application tool, for example, it may be in physical proximity and/or contact and/or coupled with the housing and/or sleeve portion, if the open end of the sleeve portion includes an object contacting portion, as noted above. In some embodiments, the energy application tool may pass through the force sensor. In other words, the force sensor may surround the energy application tool. The various embodiments of the sensor as described above are also applicable here.

Though the sensor is not physically or mechanically coupled to the energy application tool, it may be in electronic communication with the energy application tool and may act as an on/off switch for the device or instrument, as noted above. For example, when a proper force is exerted on the object by the object contacting portion of the sleeve, it may trigger the activation mechanism of the device or instrument to activate the movement of the energy application tool to start a measurement. Thus, no external switches or push buttons are needed to activate the on and off of the system, as noted above. The indication of the proper force may be indicated by visible or audible signals.

In one embodiment, the instrument may be instantaneously turned on once a proper contact force is exerted by the object contacting portion of the sleeve on the object, as indicated by visible or audible signals. In another embodiment, there may be a delay prior to turning on the instrument once a proper contact force is exerted by the object contacting portion of the sleeve on the object, as indicated by visible or audible signals. In a further embodiment, once a certain push force between the object contacting portion of the sleeve portion and the object is detected and maintained for a period of time, for example, about 0.5 seconds, the instrument may be turned on to start measurement. In this embodiment, a green light lights up the tip, and percussion will begin approximately 0.5 sec after a force in the correct range is maintained.

The proper force exerted by the operator on the object, for example, through the sleeve portion, acts as a switch of the system. When the system is not switched on, it may be desirable to know whether it has malfunction, not sufficient force or too much force is exerted. In one embodiment, the force measurement may be connected to a visual output, such as lights. Lights may be mounted at any convenient location on the device or instrument, for example, one or multiple LEDs may be mounted at the front of the device or instrument. In one aspect, a multiple light system may be included. For example, two LEDs may be used. When the force is in the correct range, the green light may be lit. If too much force is detected, the LEDs may change to red, and the instrument will not work unless the push force is reduced. In some embodiments, if the user is pushing too hard on the object, the light may change first to amber, then to red. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another aspect, no light may indicate too little force, a green light may indicate the right amount of force, while a red light may indicate too much force. In yet another aspect, a one light system may be included. For example, no light may give a signal of too little force and a red light may give a signal of too much force. In a further aspect, a flashing red light may indicate too much force and no light may indicate too little force.

In another embodiment, the force measurement may be connected to an audible output. In one aspect, the audible output may include a beeping sound to indicate too little force and a multiple beep to indicate too much force. In another aspect, the audible output may include a beeping sound to indicate too little force and a beeping sound with a flashing red light to indicate too much force. In a further aspect, the force measurement may be connected to a voice alert system for alerting too much force or too little force. In yet a further aspect, the force measurement may be connected to a voice alert system to alert too little force and a voice alert and a flashing red light for alerting too much force.

When the force sensor acts as an on/off switch, it may also act to monitor that a proper force is exerted by the object contacting portion of the sleeve portion during measurement and/or a proper alignment of the object contacting portion of the sleeve portion against the object during measurement is obtained. An inclinometer may be present, for example, as part of an electronic control system, which may trigger an audible warning when the device is outside of the angular range of operation, for example, for a tapping rod, it may trigger the warning when it is plus/minus 45 degrees, more for example, greater than about plus/minus 30 degrees from horizontal. If the device is oriented such that the axis of operation is greater than about plus/minus 45 degrees, more for example, greater than about plus/minus 30 degrees from horizontal when a push force is sensed on the object contacting portion of the sleeve portion, it may result in a warning sound being emitted by a speaker located on the device, such as the PCB within the device. In such circumstances, the percussion action will not begin until the device is returned to an acceptable angle. In some instances, if the percussion action has started when the above-mentioned departure from the range is detected, the device may not actually stop operation, but may simply be sounding an alarm, so that corrections may be made.

The present invention further includes a disposable assembly having a sleeve portion adapted for attaching or coupling to a front portion of the device housing of the above described system and method of a non-invasive manner and/or a non-destructive method of measurement having a device capable of operating by holding the device at varying angles from the horizontal and modulating the energy application process to mimic a substantially horizontal position during measurement. The sleeve portion may include a front end and a back end and may include a coupling or mounting component towards its backend for coupling or attaching to the housing. In one embodiment, the mounting or coupling component may be friction fit, mating bayonet formations, tongue and groove type formations, snap fit, clips, internesting pin and pinhole formations, latches and other interconnecting structures onto a portion of the housing or parts inside the housing. In another embodiment, the mounting or coupling component of the sleeve and the housing may be a custom-made threaded system for better fit or coupling compatibility.

The disposable feature may be part of a system for determining structural characteristics of an object, as described in all the exemplary embodiments above or below. A disposable feature adapted for attaching to a portion of the device and may include a sleeve portion that may protrude from the open front end of the device housing for a distance. The sleeve portion having a hollow interior with a front end and a rear end and an object contacting portion at the front end adapted for resting or pressing against at least a portion of the object with at least a portion of the object contacting portion of the device; and a contact feature disposed inside the sleeve portion adapted for freely moving or sliding inside the sleeve portion along the longitudinal axis, the contact feature having a body with a length and a substantially closed front end for substantially closing off the open front of the sleeve portion to minimize direct contact between the energy application tool and the object during measurement.

In another embodiment, a disposable feature adapted for enveloping a portion of the device may include a sleeve portion having a longitudinal axis and protruding from said open front end of the housing for a distance, and may have a hollow interior with a front end and a rear end and an object contacting portion at the front end adapted for resting, contacting or pressing against at least a portion of an object with at least a portion of the object contacting portion. A contact feature may be disposed inside the sleeve portion adapted for freely moving or sliding inside the sleeve portion along the longitudinal axis of the sleeve portion for a moving energy application tool, and the contact feature having a body with a length and a substantially closed front end for substantially closing off the open front of the sleeve portion to minimize direct contact between the energy application tool and the object during measurement.

As mentioned above, a contact feature freely sliding inside the sleeve portion may be disposed towards the front end of the sleeve portion of the disposable assembly. In one embodiment, the contact feature may be of any shape, for example, it may be of a short tubular section, and be of any dimension provided it is shorter than the length of the sleeve portion. It may include an open end and a closed end towards the front of the sleeve portion so that it substantially closed the front end of the sleeve portion. For it may be light weight, sufficiently thin but of sufficiently stiffness to facilitate the sliding action. In another embodiment, the contact feature may include a membrane attached to a ring. The ring may freely slide inside the sleeve portion and the membrane may substantially closed-off the opening of the housing or the sleeve portion, if one is present. The distance of movement for the freely moving or sliding contact feature may vary and in some instances may be of a predetermined distance. In some examples, such as for a ring-shaped contact feature, movement stops, such as small ridges, stops or other obstacles, may be present inside the sleeve portion to constrain the movement of the contact feature within the sleeve portion.

According to one embodiment, the sleeve portion may include an object contacting portion towards its front end for contacting a surface of an object undergoing measurement. In this embodiment, the sliding capability of the contact feature may not include any restraints as to distance and may freely sliding inside the sleeve portion. In this embodiment, the sleeve portion includes an object contacting portion towards its front end for contacting a surface of an object undergoing measurement.

According to another embodiment, the sleeve portion may not include an object contacting portion for contacting a surface of an object during measurement. In this embodiment, the sliding distance for the contact feature may be predetermined so that the front end of the contact feature may protrude further than the sleeve portion. The contact feature may be the component that provides the contact during measurement.

According to a further embodiment, the sleeve includes an object contacting portion towards its front end for contacting a surface of an object undergoing measurement and a tab extending substantially parallel to the longitudinal axis of the sleeve portion so that when the object contacting surface of the sleeve portion is in contact with at least a portion of a surface of the object undergoing the measurement, the tab may be resting on a portion or surface of the object that is different and is substantially perpendicular to the surface of the object in contact with the sleeve According to yet another embodiment, the sleeve portion includes a tab extending substantially parallel to the longitudinal axis of the sleeve portion so that when the object contacting surface of the contact feature is in contact with at least a portion of a surface of the object undergoing the measurement, the tab may be resting on a portion or surface of the object that is different and is substantially perpendicular to the surface of the object in contact with the contact feature.

According to still another embodiment, the sleeve portion may include a tab and a component, for example, a ridge, protrusion or other component substantially orthogonal to the surface of the tab on the side adapted for facing the surface of an object. For example, for teeth, the component may nest between adjacent teeth or other orthogonal surface and may thus aid in preventing any substantial lateral movement of the tab across the surface of the object and/or further aid in repeatability. The tab may be of sufficient length or width, depending on the length or width of the top portion of the object so that the ridge or protrusion may be properly located during operation. In rare instances where the tab may interfere with a stable reading, a flat disposable assembly may be used to reposition the sleeve portion lower on the object to be tested, as in the case of certain implant transfer abutments used for impressions of implant fixtures.

In some embodiments, the sleeve portion may include a tab extending substantially parallel to the longitudinal axis of the sleeve portion and include at least one formation (e.g. a groove, channel, notch, indentation, etc.) so that when the object contacting surface of the contact feature is in contact with at least a portion of a surface of the object undergoing the measurement, the tab may be resting on a portion or surface of the object and at least partially conform to a protrusion, bump or other raised portion of the surface of the object using the at least one formation.

In one embodiment, in addition to the disposable assembly having a mounting component or coupling component that may be friction fit, mating bayonet formations, tongue and groove type formations, snap fit, clips, internesting pin and pinhole formations, latches and other interconnecting structures onto at least a portion of the housing or parts inside the housing, additional features may be included in the device so that the activation mechanism of the device may not be triggered if the attached disposable assembly had been used before.

In another embodiment, in addition to the disposable assembly having a mounting component or coupling component that may be friction fit, mating bayonet formations, tongue and groove type formations, snap fit, clips, internesting pin and pinhole formations, latches and other interconnecting structures onto at least a portion of the housing or parts inside the housing, the mounting component may include a component that allows a predetermined number of connections made by the disposable assembly to the housing or parts inside the housing.

The present invention relates to yet another system and method for measuring structural characteristics in a non-destructive and non-invasive way, and may include a device capable of operating by holding the device at varying angles from the horizontal and modulating the energy application process to mimic a substantially horizontal position during measurement. The system may include a drive mechanism that may vary the travel distance of the energy application tool, while maintaining an initial velocity of impact of the object by the energy application tool. For example, when the energy application tool includes a tapping tool, the distance may vary between a range of about 2 mm to about 4 mm. The decrease of the travel distance of the energy application tool, for example, from about 4 mm to about 2 mm, while maintaining the same initial velocity at impact, or contact, may enable faster measurement without compromising the operation of the system. The system may or may not include the various exemplary embodiments described above or below. For example, the system may or may not have disposable parts and/or features for aiding in repositionability and/or lessening impact with features mentioned before or below.

For this immediately mentioned above invention and all the other embodiments of the device described above herein, the device, for example, a percussion instrument, with or without any disposable feature, may also include a tab extending from the open end of the housing or sleeve portion so that the object contacting surface of the sleeve portion or contact feature described above is in contact with at least a portion of a surface of the object undergoing the measurement, the tab may be resting on a portion or surface of the object that is different and is substantially perpendicular to the surface of the object in contact with the sleeve or contact feature, as mentioned above. The tab and the sleeve or contact feature together assists in the repeatable positioning of the device with respect to the object. In addition, the tab may be adapted for repetitively placed substantially at the same location on the surface of the object every time.

For all the embodiment described herein, the component may be of any shape and size. In one aspect, for example, if the object is a tooth, the component may be short and of a sufficiently small thickness so that it may fit between adjacent teeth. In another aspect, for example, if the object is a tooth, the component may be short and shaped to fit between the top portion of adjacent teeth. In yet another aspect, for example, if the object is a tooth, and the component is to rest against the back surface, it may be of a dimension to cover a major portion of the back surface.

The tab and/or tab and component not only serve to aid in repeatable positioning of the instrument on an object, such as a tooth or mechanical or industrial structure, composites and similar, but the tab and/or tab and component also serve to help keep the object, such as a tooth or mechanical or industrial structure, composites and similar, as mentioned above, from moving in directions other than the direction parallel to the energy application or tapping direction. This helps to minimize any unnecessary disturbances of the object and/or the foundation it is anchored to and/or complications which may arise from these other disturbances during testing, thus further contributing to the sensitivity and/or accuracy of detection. The tab or the tab and/or component is applicable whether the sleeve portion has an object contacting portion or the contact feature provides the contact to the object.

The end of the sleeve not having the tab protruding from it may be flat or substantially flat and the part of the tab in contact with the top of the object may be also flat or substantially flat. The tab may extend in a substantially parallel direction from the end of the sleeve. In one aspect, the tab may be integral with the sleeve for a distance before protruding from the end of the sleeve, keeping substantially the cross-sectional outline of the sleeve after protruding from the sleeve. In another aspect, the tab may protrude uniformly from the top or bottom portion of the sleeve, but with a substantially different cross-sectional outline from that of the sleeve after protruding from the sleeve. In rare situations, the tab may not protrude at all to allow testing at a lower position on the object.

In one embodiment of the present invention, the tab may have a contact surface substantially mirroring the contour of the surface of an object to which it comes into contact during use for aiding in reproducibly positioning of the device directly on an object.

In one aspect, the protruding portion of the tab may have a rectangular cross-section. In another aspect, the protruding portion of the tab may have a slight arched top portion. In yet another aspect, the protruding portion of the tab may conform to the contour of the surface which comes into contact with the object.

In any of the embodiments, the corners of the tab are smooth or rounded or substantially smooth or rounded to avoid any catching on the object they may be resting on.

In general, the present device may be useful in making any measurements whereby vibration is generated through the application of energy, for example, the striking of, such as a tapping rod, on an object. The advantages are that the device may be held in contact with the object during the tapping action, in contrast to traditional devices that are not in contact.

The sleeve portion and the tab, and the feature and/or the sleeve, the tab and the contact feature, may be made of any material having vibration damping, acoustic damping, or vibration attenuating properties and the sleeve may be of such length so that any vibration traveling through the sleeve to the housing of the handpiece may be substantially attenuated. In one embodiment, the sleeve and the end of the housing adjacent to the sleeve may be made of the same material. In another embodiment, the sleeve and the end of the housing it is attached to may be made of materials having similar vibration attenuating properties. In yet another embodiment, the sleeve and the end of the housing it is attached to may be made of different materials. In a further embodiment, the sleeve and the end of the housing it is attached to may be made of materials having different vibration attenuating properties. In yet a further embodiment, the sleeve may be made of any material with a vibration attenuating coating on its surface or surfaces. In still yet another embodiment, the sleeve, tab and/or feature may be made of different materials having similar thermal expansion properties.

In addition, the sleeve portion, the contact feature and tab and/or the sleeve, the tab and the component, may be made of recyclable, compostable or biodegradable materials which are especially useful in those embodiments that are meant to be disposed of after one use.

The energy application tool is driven by a drive mechanism during measurement, as noted above. The drive mechanism may be an electromagnetic mechanism and may include an electromagnetic coil. The drive mechanism may include a permanent magnet secured to the back end of the energy application tool, for example, the tapping rod, and the electromagnetic coil may lie axially behind this permanent magnet. In one embodiment, together with the back part of the housing, if the device is a handpiece, and any electrical supply lines, the magnetic coil forms a structural unit which may be integrally operational and which may be, for example, connected to the remaining device by a suitable releasable connection, for example, a screw-type connection or a plug-type connection. This releasable connection may facilitate cleaning, repairing and others. In another embodiment, the back part of the housing, if the device is a handpiece, and any electrical supply lines, the electromagnetic coil form a structural unit which may be integrally operational and which may be connected to the remaining device permanently. The energy application tool, such as the tapping rod, is located in the front part of the housing and the mounting mechanism for the tapping rod may include frictionless bearings. These bearings may include one or more axial openings so that the neighboring chambers formed by the housing and the tapping rod are in communication with one another for the exchange of air.

In one embodiment, the tapping rod may have a substantially constant cross-sectional construction over its entire length, with a permanent magnetic ensemble mounted at the end away from the free end, as noted above. The electromagnetic coil of the driving mechanism may be situated behind the same end of the energy application tool for example, the tapping rod as the permanent magnetic ensemble, resulting in a relatively small outside diameter for the housing. In this embodiment, the outside diameter of the housing may be substantially defined by the diameter of the electromagnetic coil, the cross-section of the energy application tool, such as the tapping rod, the mounting mechanism of the tapping rod in the housing, and the thickness of the walls of the housing. However, the length of the tool may be designed such that the electromagnetic coil (which represents the largest mass of the assembly) may be positioned to balance the device, for example, the handpiece in the hand, counterbalancing the batteries, if present, at the rear of the device.

The device itself may be tethered to an external power supply or be powered by an electrical source included inside the housing, such as, for example, a battery, a capacitor, a transducer, a solar cell, an external source and/or any other appropriate source.

In one embodiment, communication between the drive mechanism or portions of the drive mechanism, for example, the electronic control board part and the energy application tool, such as the tapping rod, may be via a lead or line of electrically conductive, insulated wire which may be wound spirally in a concentric fashion around the tapping rod and has spring-elastic properties. This may also allow a minimum space requirement with respect to the line management. The strand of wires wound concentrically around the rod connects the piezoelectric sensor to the control electronics. One purpose of concentrically winding the wire is to minimize the stress on the wire from repeated forward and back movement of the rod. In some embodiments, a helical spring, which may be formed by the spirally wound wire, may help to avoid or prevent looping or twisting of the wire connection.

In another embodiment, the communication between the drive mechanism and the energy application tool may be transmitted wirelessly via any suitable wireless connections. In one example, the energy application tool such as the tapping rod may be propelled forward by energizing the electromagnetic coil and creating a magnetic field that repels the magnet in the end of the tapping rod. The rod is retracted by reversing the polarity of the voltage applied to the electromagnetic coil. The magnet may also serve to hold the rod in its retracted position when the electromagnetic coil is not energized, through its magnetic attraction to the steel core of the coil.

A helical spring, if present, may be composed of stranded wires having two twisted individual wires or of a coaxial line. In its loaded condition, the spring may be compressed to such a degree that the force of its prestress corresponds to the frictional force and opposes this frictional force during the forward motion of the energy application tool, for example, the tapping rod from the retracted position to the extended position, or from a substantially parallel position to the longitudinal axis of the housing to a position making an acute angle with the axis at a pivot. The prestressed path of the spring may therefore be far greater than the stroke of the energy application tool, for example, the tapping rod so that spring power remains substantially constant over the entire stroke of the tapping rod. Any undesirable frictional force of the bearings of the mounting mechanism for the tapping rod during the forward motion may also be substantially compensated by this spring.

In one embodiment, the housing may be tapered towards the end surrounded by the sleeve portion so that the device may have a substantially uniform dimension when the sleeve is attached. In another embodiment, the housing may have a substantially uniform dimension and the sleeve may expand the dimension of the end it surrounds to a certain extent. In a further embodiment, the sleeve itself may have an inverse taper towards its free end to increase the flat area of contact with the object.

In general, the present device may be useful in making any measurements whereby vibration is generated through the application of energy, for example, the striking of, such as a tapping rod, on an object. For example, a time versus percussion response profile may be generated. The evaluation system may include a data analyzer configured to evaluate the shape of the time versus percussion response profile. The time versus percussion response profile may include time-energy, time-stress, time-force or acceleration profile, as noted above. For example, evaluation may include counting the number of energy maxima reflected from the object after energy application.

In general, the structural characteristics as defined herein may include vibration damping capacities; acoustic damping capacities; defects including inherent defects in, for example, the bone or the material that made up the object; cracks, micro-cracks, fractures, microfractures; loss of cement seal; cement failure; bond failure; microleakage; lesions; decay; structural integrity in general or structural stability in general. For an anatomical object, such as a tooth structure, a natural tooth, a natural tooth that has a fracture due to wear or trauma, a natural tooth that has become at least partially abscessed, or a natural tooth that has undergone a bone augmentation procedure, a prosthetic dental implant structure, a dental structure, an orthopedic structure or an orthopedic implant, such characteristics may indicate the health of the object, or the health of the underlying foundation to which the object may be anchored or attached. The health of the object and/or the underlying foundation may also be correlated to densities or bone densities or a level of osseointegration; any defects, inherent or otherwise; or cracks, fractures, microfractures, microcracks; loss of cement seal; cement failure; bond failure; microleakage; lesion; or decay. For objects in general, for example, polymeric composite structures including honeycombs or layered honeycombs or metallic composite structure; an airplane structure, an automobile, a ship, a bridge, a building, industrial structures including, but not limited to power generation facilities, arch structures, or other similar physical structures; such measurements may also be correlated to any structural integrity, or structural stability, such as defects or cracks, even hairline fractures or microcracks and so on.

Additionally, changes in the structure of the tooth or any foundation a mechanical structure is attached or anchored to that reduce its ability to dissipate the mechanical energy associated with an impact force, and thus reduce overall structural stability of the, for example, tooth, can be detected by evaluation of the energy return data as compared to an ideal non-damaged sample. In addition, as noted above, the present invention also contributes to the accuracy of the location of detection of defects, cracks, micro-cracks, fractures, microfracture, leakage, lesions, loss of cement seal; microleakage; decay; structural integrity in cement failure; bond failure; general or structural stability in general.

As noted above, the device may be tethered to an external power supply or be powered by an electrical source included inside the device housing. If powered by an electrical source inside the device housing, the power source may or may not be rechargeable. If rechargeable, a base charging station may be used. The base station may be a separate independent station or it may be part of the system of the present invention. For an independent charging station, any existing station may be applicable. The charging mechanism may be wired or wireless. For these charging base, only electrical current to charge the device is provided in most instances. For a base station that may be part of the system, more than electrical current to charge the device may be provided.

The present invention still further relates to a base station that may be part of the system of the present invention and may be plugged into the computer, for example, a PC via a USB cable. This connection may provide both data transfer between the PC and the base station, and electrical current to charge the device during the charging process when the device is docked. In this way, the base station may also serve to act as a wireless transceiver for the PC in the communication with the wireless transceiver in the device.

It may be desirable for each device to be accompanied by its own charging base station. This may avoid the possibility of the wrong device communicating with the wrong base station, in a multiple device environment. This may be important in any testing setting, for example, a dental office.

During preparation of the system just prior to performing a measurement on an object, the device is docked in the charging base to pair that device with that base station as part of the usage protocol, for example, prior to starting a patient testing session in a dental office. The age protocol may be controlled by the software.

For the embodiments where the device may be equipped with a disposable feature or assembly described above, the disposable portion is generally removed from the device prior to placing the device in the charging base. In other embodiments, the disposable portion may be physically accommodated in the interface between the device and the base.

The present invention yet further relates to a non-reusable and disposable assembly or feature in a healthcare setting. As noted above, the disposable feature or assembly is for aiding in eliminating or minimizing contamination of the object undergoing the measurement through transfer from the system or cross-contamination from previous objects undergoing the measurements, without having to carry out a decontaminating process prior to moving to a different test object. To ensure that such features or assemblies once used are not reused, the disposable features or assemblies may be programmed to be one use. In one embodiment, a computer chip may be used. The chip may be present on a PCB located on the disposable feature or assembly, for example, in the back of the disposable assembly, may serves to ensure that once used, it cannot be or is not reused, so that any unwanted material may not be transferred. from one patient to another. When a disposable feature or assembly is coupled to the device, the chip in the assembly or feature is interrogated by the device with a challenge and response system to ensure authenticity. Once authenticated, it is permanently marked as 'used'. If a used assembly or feature is placed on the device again, whether it is the same device or a different one, the challenge and response will fail, and the device will not be able to function as intended. In another embodiment, a timeout function may also be used to prevent the reuse of the disposable assembly or feature after a certain period of coupled time. In a further embodiment, the chip as well as the timeout function may be used for further insurance. In yet a further embodiment, the attachment mechanism of the disposable feature or assembly may include a part that once removed from the device is either snapped off or is warp to render it no longer attachable to a device.

To further facilitate the ease of use of the system, better lighting of the object undergoing measurement may be provided, such as with light pipes or other illumination which may be used to enable better lighting of the object and enhance the visualization by the user. In some embodiments, the light pipes may also be utilized to aid in coupling between components, such as between the handpiece and the disposable feature.

The disposable feature, though so named, may be one-use or may also be reusable, if desired. Thus, the feature may be autoclavable or sterilizable using heat or chemicals. In either disposable or reusable embodiment, various removable connections maybe provided. For example, the disposable feature may be connected through any appropriate form of connection, such as, for example, any threaded attachment, friction fit, mating bayonet formations, tongue and groove type formations, snap fit, clips, internesting pin and pinhole formations, latches and other interconnecting structures.

The system may be applicable for testing various objects, both anatomical and mechanical, as noted before. For an anatomical object, such as a tooth, natural or restored, prosthetic dental implant structure, a dental structure, or an orthopedic implant, measurement or testing is generally performed while the object is stationary, unless the tooth or tooth structure is loose and some slight movement may be present. For a mechanical object, which may include, but not limited to polymeric composite structures including honeycombs or layered honeycombs or metallic composite structure; an airplane structure, an automobile, a ship, a bridge, a tunnel, a train, a building, industrial structures including, but not limited to power generation facilities, arch structures, or other similar physical structures, testing may also be carried out on stationary or a mobile object while moving. Thus, mechanical objects may also be undergoing testing when they are either stationary or moving, which may give particular insight into the object under actual working conditions. For moving objects, such as a train, the testing may be performed over many different spots. This may be performed using one energy application tool, over a plurality of spots on the object, to obtain an average condition of the object in general or be performed on the same spot using many separate tools or devices to obtain an average result on the same spot. For performing measurement on the same spot using many energy application tools, the devices or tools may be positioned, for example, in succession along the path of the moving object over a distance, for example, an array of tapping rod impacting the object, and by controlling the spacing between the tools or devices one may be able to match the speed of the moving object, for example a train, to the spacing of the application of energy on the same spot of the object for obtaining an average value for the spot. In this example, measurements may be performed under actual operating conditions. In one embodiment, the array of devices may be a line array, either vertical or horizontal arrays, or a curve array. In another aspect, the array may be arranged in a two-dimensional array, planar or curvilinear.

In embodiments where the object is large, measurement at different locations of the object, for example, impacting at a plurality of portions of the object may allow better evaluation of the structural properties that are better representations of the object.

The present invention additionally offers the added ability of operating at varying angles from the horizontal or vertical, and modulating the energy application process to mimic a substantially horizontal or vertical position during measurement. This may further aid to generate a more complete picture of the true state of the object undergoing measurement. For example, as noted above, while convention methods of testing an object may be more easily obstructed by a large surface defect as this may mask other defects below the surface or other spots on or near the surface, the ability of the present invention to operate at any angles may alleviate such difficulties, for example, the danger of obstruction due to a large defect overwhelming a smaller defect when operating at one angle, may be minimize when operating at other angles.

In addition, as noted above the disposable feature may also be present in any contact or non-contact energy application tool, as the tools may still be present inside a patient's oral cavity in dental application, or in situations where contamination or cross-contamination is present, in order to minimize contamination.

In general, the energy application tool may be of any form or shape and any type for application of different types of energy. For example, for testing in a dental environment, the form or shape of the tool may be of smaller dimension than that for an airplane part. The type of applied energy may also vary, for example, it may be mechanical energy, electromagnetic energy, ultrasound or acoustic energy, as noted above. In any type of energy source, minimizing the amount of energy to product a good result is desired as higher energy may potentially damage the object and is thus not as desirable.

The present invention may further include, in some embodiments, varying shape of the contacting portion or tip of the energy application tool configured to better suit the surface of the object to be measured, whether there is physical contact or not during impact. For example, the tapping or impacting surface of the tool may have different shapes, for example, it may be flat, curve or shaped like the surface to be measured.

In one embodiment, the present invention may include a kit of a plurality of energy application tools having varying sizes and shapes for contacting portion or surface of the energy application tool suitable for measuring a larger area of an object with varying topography.

In another embodiment, the present invention may provide a kit having an energy application tool and a plurality of interchangeable impact portions for the energy application tool, having varying contacting portion sizes and shapes to better suit the specimen for each type of objects.

In a further embodiment, the present invention may include a device having an array or arrangement of energy application tools. In one aspect, the array of tools may be arranged in a line, vertical or horizontal. In another aspect, the array may also be curved. In yet another aspect, the array may be 2-dimensional array, planar or curved.

The device and/or a portion of the device may also have an antimicrobial coating coated thereon capable of eliminating, preventing, retarding or minimizing the growth of microbes, thus minimizing the use of high temperature autoclaving process or harsh chemicals and may increase the kind and number of materials useful as substrates for making such tools or instruments.

The present invention further includes a system for measuring structural characteristics of an object having a device with a housing having a hollow interior, a longitudinal axis, and an open front; an energy application tool mounted inside said housing for applying energy to said object, said energy application tool having a resting and an active position, and applying energy through said open front of the housing to impact said object undergoing measurement; a drive mechanism supported inside said housing and coupled to the energy application tool, said drive mechanism adapted for repeatedly applying energy to impact the object with substantially the same amount of force whether the longitudinal axis of the device is in a substantially horizontal position or making an angle of up to less than about +/−45 degrees with the horizontal position, the drive mechanism has a sensing or measuring system; and a computer coupled to the device for controlling the energy application tool and for analyzing any data collected by the device. The system may measure, for a time interval, a percussion response to a percussion response versus time profile. In one embodiment, the percussion response includes the displacement of the energy application tool. In another embodiment, the percussion response includes the energy reflected from the object as a result of applying energy.

The embodiments of system used to generate profiles may include all the above described embodiments. Analysis of profiles generated reveals that the profile for a normal tooth is different from that of a damaged tooth and different profiles of damaged teeth also represent different kinds of defects, different locations of defects, number of defect sites, and combinations thereof.

The present invention further relates to a system and method for measuring structural characteristics of an object in a non-invasive manner and/or a non-destructive manner. The test results may be from different objects that may be related or unrelated. Surprisingly, the test results may be used not only to predict results of objects related only to objected being tested, but when analyzed and compiled, the cumulative results of the measurements may generate a model, that may be used, for quickly predicting, with one simple test, the kind of issues present in an unrelated object that is not discernible visually or from radiographs. The model may be used for aiding in determining proper corrective measures to monitor and/or restore the object to substantially issue free stage.

The present invention together with the above and other advantages may best be understood from the following detailed description of the aspects, embodiments and examples of the invention and as illustrated in the drawings. The following description, while indicating various aspects, embodiments and examples of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

FIG. 1 illustrates a block diagram of a device in embodiments of the present invention;

FIGS. 1a and 1b illustrate perspective views of a handpiece with sleeve portions in embodiments of the invention;

FIG. 1c illustrates the end of a handpiece without a sleeve portion;

FIG. 1f illustrates a block diagram of a device with a substantially perpendicular sleeve portion and a pivoting energy application tool;

DETAILED DESCRIPTION OF THE INVENTION

Figure 1G:
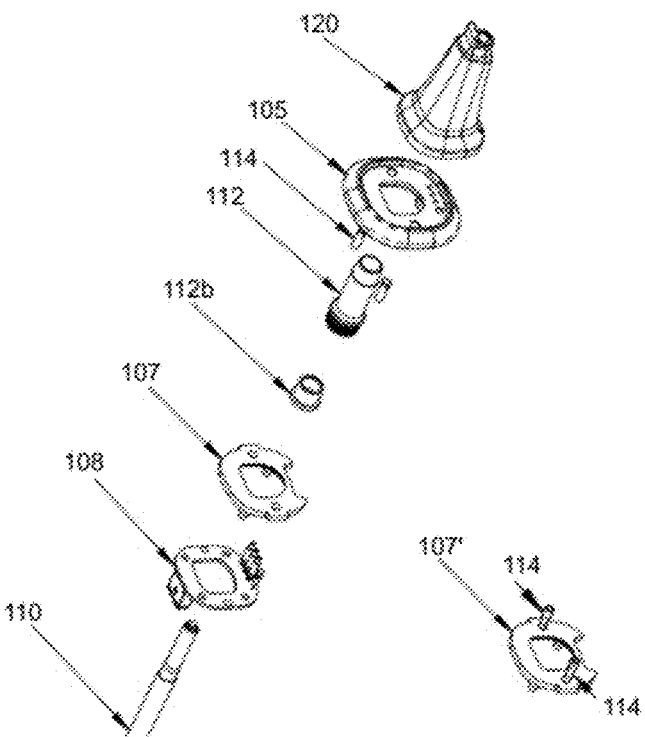
FIG. 1g illustrates an alternative configuration for lighting features.

The detailed description set forth below is intended as a description of the presently exemplified systems, devices and methods provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplary methods, devices and materials are now described.

All publications mentioned herein are incorporated herein by reference for the purpose of describing and disclosing, for example, the designs and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention relates to a system and method for measuring structural characteristics of an object in a non-invasive manner and/or using a non-destructive method of measurement. The object may be subjected to an energy application process and the system is adapted for providing an objective, quantitative measurement of structural characteristics of the object after the energy application process. The system and method of the present invention are capable of operating at varying angles from the horizontal and modulating the energy application process to mimic a substantially horizontal position during measurement, such as to increase flexibility of operation, for example, to adapt for reaching hard to reach objects, to generate more reproducible measurements, and also to better be able to detect any abnormalities that may be present in an object. The system and method may include a device, for example, a percussion instrument, having at least a portion capable of being reproducibly placed in contact with the object undergoing such measurement for more reproducible measurements, including for an object present in, for example, space restricted, and/or difficult to reach locations. As mentioned above, the system and method of the present invention is a non-destructive method. This is applicable to a system that may or may not have disposable parts and/or features for aiding in repositionability. As noted above, the device may be part of a system that includes computerized hardware and instrumentation software that may be programmed to activate, input and track the action and response of the device for determining the structural characteristics of the object. The hardware may include a computer for controlling the device and for analyzing any data collected, for example, the deceleration of the energy applying tool, for example, the tapping rod, upon impact with an object. In general, the device and hardware may communicate via wired connection(s), wireless connection(s) and/or a combination. Upon activation, the energy application tool, for example, the tapping rod extends at a speed toward an object and the deceleration of the tapping rod upon impact with the object may be measured by a measuring device, for example, a piezoelectric force sensor, installed in the device, and transmitted to the rest of the system for analysis. In one aspect, the tapping rod may be programmed to repeatedly strike an object, for example, a certain number of times per second or minute at substantially the same speed and the deceleration information is recorded or compiled for analysis by the system. In some embodiments, the object may be struck 4 times per second.

In general, the object may be subjected to an energy application processes provided via a device, for example, a handpiece, which forms a part of a computerized system capable of collecting and analyzing any data animating from the object. As noted above, many different structural characteristics may be determined using the system and methods of the present invention, including vibration damping capacities, acoustic damping capacities, structural integrity or structural stability of both mechanical and anatomical objects and any foundations they may be anchored thereon, as noted above. For an anatomical object, such as a tooth, natural or restored, prosthetic dental implant structure, a dental structure, or an orthopedic implant, examples of the structural characteristics as defined herein may include vibration damping capacities, acoustic damping capacities, or structural stabilities and may indicate the health of the object. The health of the object, may also be correlated to bone densities or a level of osseointegration; structural integrity such as defects or cracks, noted above. For objects in general, such measurements may also be correlated to their structural integrity such as defects or cracks, also a noted above. For a physical structure, such as a plane, an automobile, a ship, a bridge, a building or other similar physical structures or damping material suitable to aid in the construction of such structures, examples of the structural characteristics as defined herein may include vibration damping capacities, acoustic damping capacities, or structural stabilities and may indicate the health of the structural integrity of the object.

The present invention provides an effective and repeatable measurement of the structural characteristics of an object, mentioned above and/or below.

The instrument of the present invention may be used to such purposes and may be useful to predict the suitability of a material prior to construction in addition in for example, an anatomical object, to detection of loss of cement seal; cement failure; bond failure; microleakage; decay and so on after the construction, as mentioned above. In addition, the present invention is useful in distinguishing between defects inherent in the material making up the structure or object, and cracks or fractures as discussed above due to trauma or wear or repeated loadings. Defects inherent in the bone or material construction of an implant, or a physical structure, for example, may include lesions in the bone, similar defects in the implant construction or polymer, polymer composites or alloys, any type of ceramics, or metallic composites or alloys. For example, in measuring the damping characteristics of teeth, whether natural or restored, dental implant structures, orthopedic implant structures, and a variety of other applications where the measurement of damping characteristics is utilized, including, but are not limited to, testing airplane structures, composite structures, engineering materials, or the secureness of medical implants, and is particularly advantageous in locations that were difficult to access or where liquid couplants could not be used. Structural integrity, such as the looseness of a screw, cracks in teeth as well as bone and bone voids, debonded restorations, and damage in integrated circuit materials may also be measured. However, the above list is not intended to be exhaustive.

In one aspect of the invention, the system may include an instrument which houses an energy application tool for generating an applied force on an object, such as through physical impact, percussion or repeated tapping impact, and a sensing mechanism for detecting characteristics of the resulting applied force, such as, for example, the deceleration of the energy application tool upon impact, energy back-propagated from the impact, physical deformation of the energy application tool, and/or any other appropriate characteristic or combination thereof.

Figure 1D:
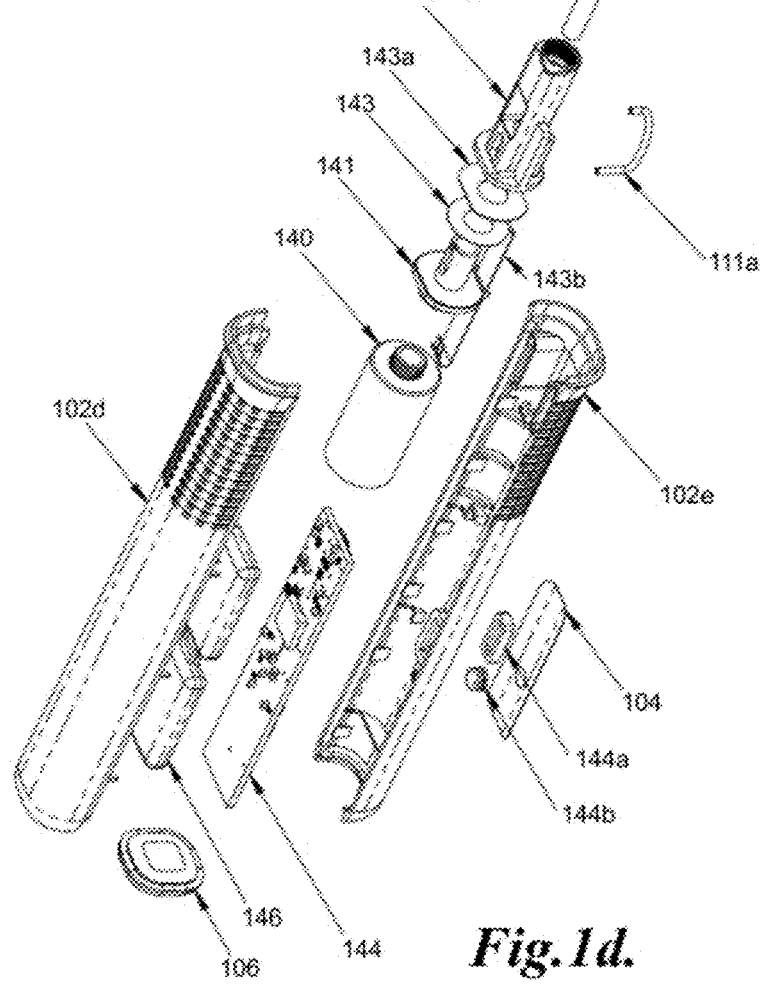
FIG. 1d illustrates an exploded view of a handpiece with a sleeve portion.
Figure 11A:
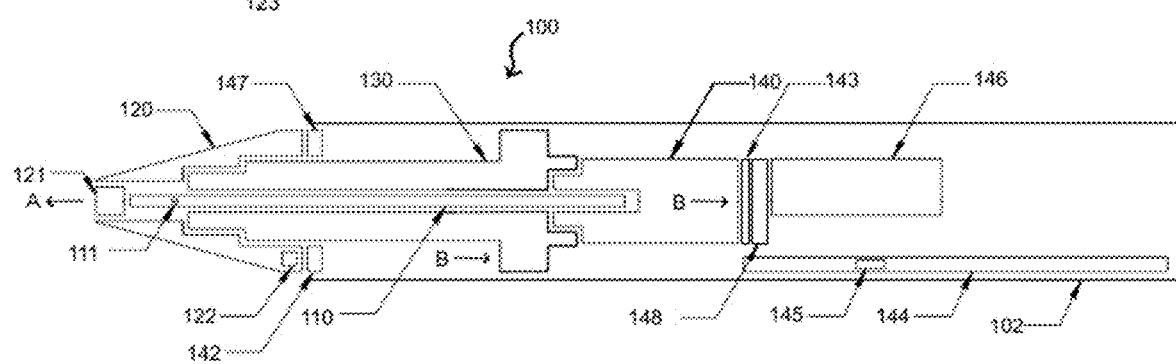
FIG. 11a illustrates a block diagram of a handpiece with a sleeve portion and rigidly connected force transfer components.
Figure 11D:
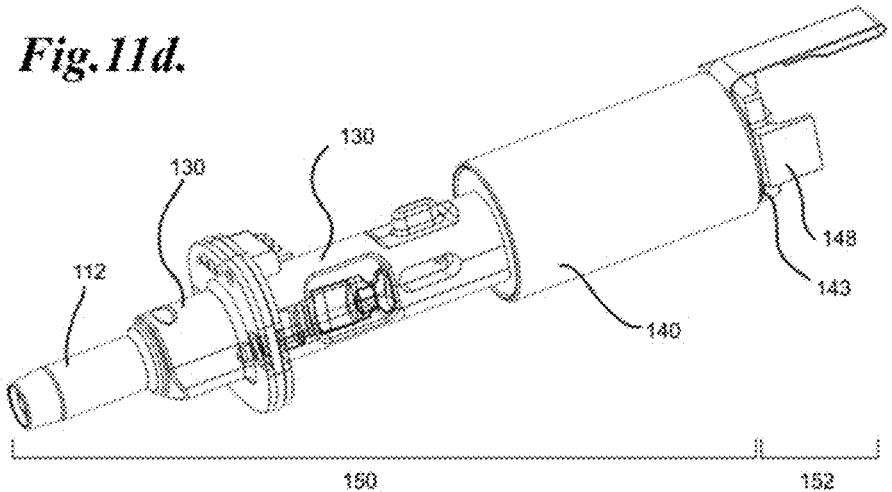
FIG. 11d shows the components that are rigidly connected together in the handpiece of FIGS. 11-11c.
Figure 11:
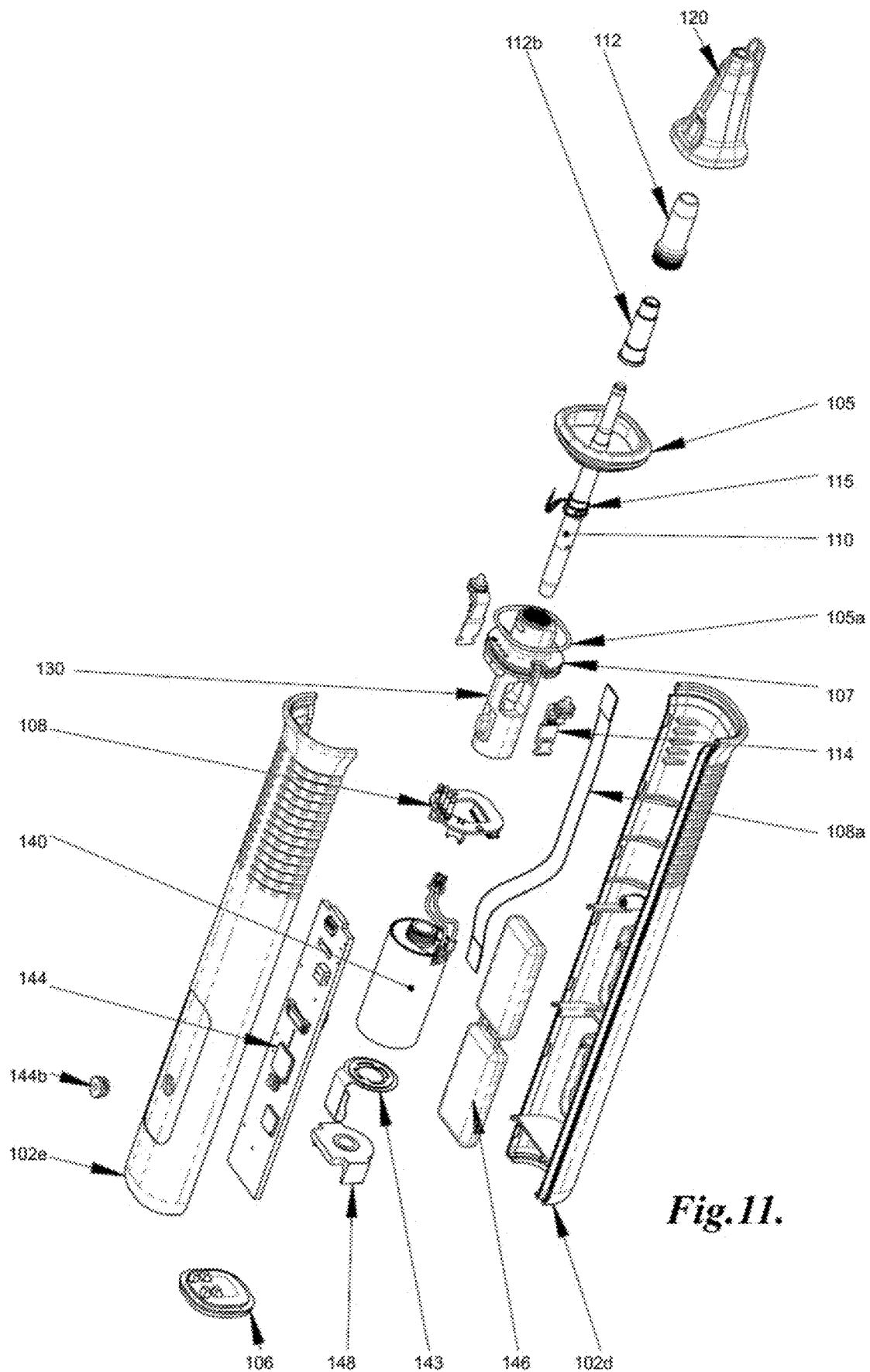
FIG. 11 illustrates an exploded view of a handpiece with a sleeve portion and rigidly connected force transfer components.

In exemplary embodiments, the instrument may include a handpiece 100 having a housing 102 which houses the energy application tool and sensing mechanism, as illustrated in the block diagrams of FIGS. 1 and 11a, and the exploded views of FIGS. 1d and 11. In general, a handpiece may refer to a handheld device, but may also include, without limitation, any other appropriate form for the desired application, such as mounted devices or tool/mechanically/robotically articulated devices. The handpiece 100 may also be referred to, for example, as a device or instrument interchangeably herein. In some embodiments, the energy application tool 110, as illustrated, may be mounted within the housing 102 for axial movement in the direction A toward an object, and such axial movement may be accomplished via a drive mechanism 140. Drive mechanism 140 may generally be a linear motor or actuator, such as an electromagnetic mechanism which may affect the axial position of the energy application tool 110, such as by producing a magnetic field which interacts with at least a portion of the energy application tool 110 to control its position, velocity and/or acceleration through magnetic interaction. For example, an electromagnetic coil disposed at least partially about the energy application 110 may be energized to propel the energy application tool 110 forward toward the object to be measured, as illustrated with the electromagnetic coil 140, which may be retained by a wrapping 140b, as illustrated in the exploded view of FIG. 1e. The electromagnetic coil may also, for example, be alternatively energized to propel the energy application tool 110 backward to prepare for a subsequent impact. Other elements, such as rebound magnetic elements, may also be included, such as to aid in repositioning of the energy application tool 110 after propelling via the electromagnetic coil. A sensing mechanism, such as the sensing mechanism 111, may then be utilized to measure the forces or energy of the energy application tool 110, and generally separate from outside forces such as contact forces of the handpiece 100 against an object, which may generally be detected, for example, by a separate sensor, such as a force sensor 143, as discussed in more detail below. The drive mechanism 140 and/or other portions of the instrument may generally be powered by a power source, as shown with power source 146, which may be a battery, capacitor, solar cell, transducer, connection to an external power source and/or any appropriate combination. An external connection to a power source, either to power the handpiece 100 or to charge the internal power source, such as the power source 146, may be provided, such as a power interface 147 in FIG. 1, which may include, for example, a power contact 113a as in FIGS. 1c and 1d for direct conductive charging, or the power interface 147 may utilize wireless charging, such as inductive charging.

In some other embodiments, the energy application tool 110 may be utilized to move substantially in a direction A which may be perpendicular or substantially perpendicular to the longitudinal axis of the housing 102, as illustrated in the block diagram of a handpiece 100 in FIG. 1f. As illustrated, the energy application tool 110 may, for example, be substantially L-shaped to accommodate the interaction with the drive mechanism 140 and protrude in direction A, substantially perpendicular to the axis of the housing 102. As illustrated in an example, the drive mechanism 140 may act on the energy application tool 110 to cause it to rock on a pivot 110*a*, causing it to move in direction A at its tip. The drive mechanism 140 may utilize, for example, an alternating magnetic element which may act on the energy application tool 110 to cause it to move alternatingly in two directions, such as up and down. In another example, the bend portion of the L-shaped energy application tool 110, such as shown with bend 110*b*, may include a flexing and/or deformable construction such that a linear force applied by the drive mechanism 140 may push the energy application tool 110 in the direction A at the tip by conveying the forward motion around bend 110*b*. For example, the bend 110*b* may include a braided, segmented, spring-like and/or otherwise bendable section that may also convey motion and/or force around a bend. In general, the shape of the L-shaped energy application tool 110 may generally include other angles besides 90 degrees, such as between approximately +/−45 degrees from the rearward portion 110*d*. In some embodiments, the energy application tool 110 may also include multiple portions which may be separable, such as portions 110*c* and 110*d*, such that, for example, the portion 110*c* may be removed and disposed between uses or patients, such as to aid in preventing cross-contamination. In general, the separable portions may include an interface to couple them for use in a measurement such that they substantially act as a unitary energy application tool 110, as described below.

Figure 1E:
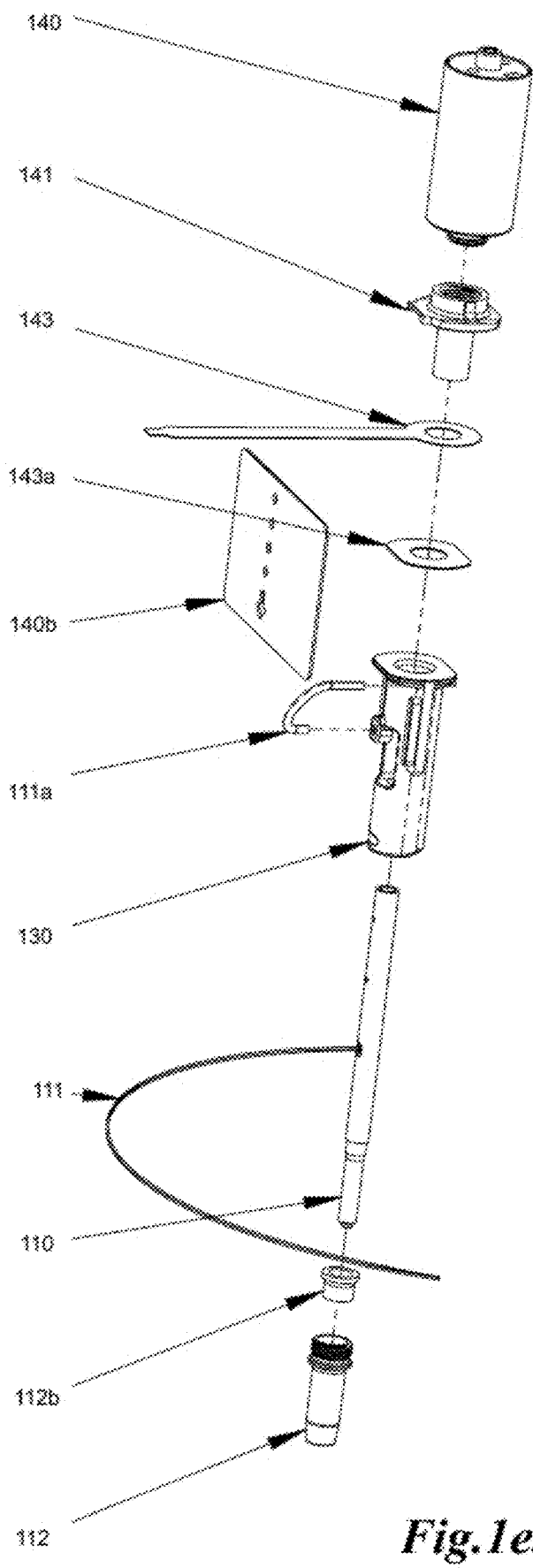
FIG. 1e illustrates an exploded view of a portion of a handpiece showing portions of the drive mechanism, a force sensor and a piezoelectric sensing wire without a sleeve portion shown.
Figure 1H:
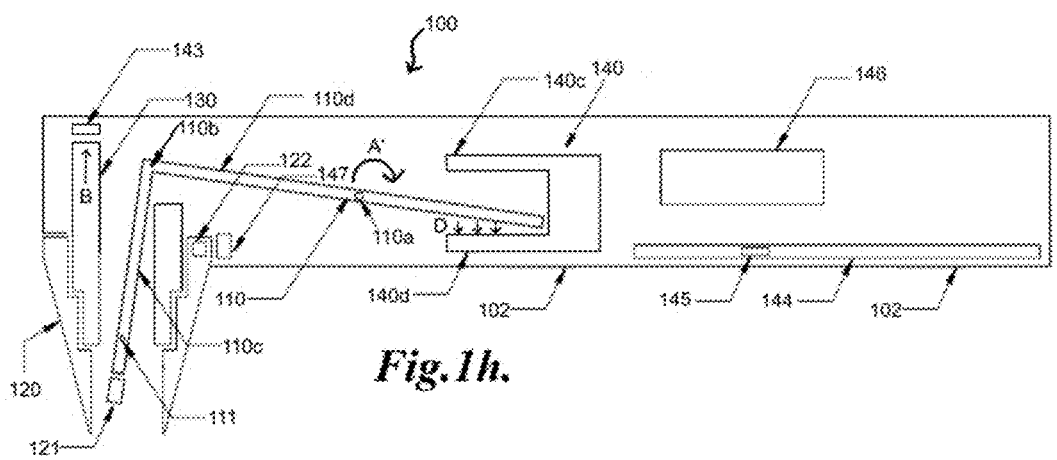
FIGS. 1h and 1i illustrate the motion of a pivoting energy application tool.
Figure 1I:
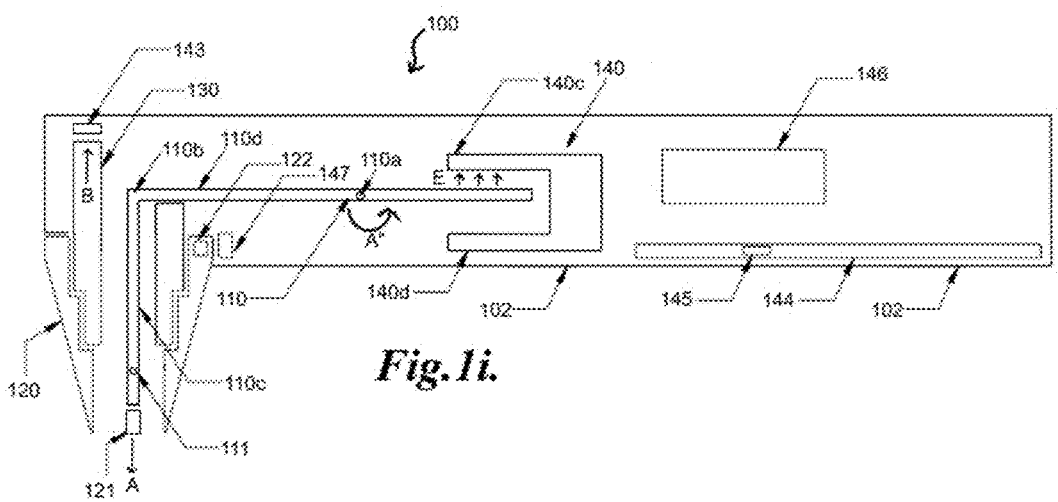

In some embodiments, the L-shaped energy application tool 110 may rock on a pivot 110*a*, such as, for example, with an external force applied from a drive mechanism 140, as shown in FIGS. 1*h* and 1*i*. For example, the drive mechanism 140 may apply alternating forces to the energy application tool 110 to cause it to rock about the pivot 110*a*, such as with a force applied D from portion 140*d* applied to the rearward portion 110*d* to cause rocking in direction A' away from a target object, as shown in FIG. 1*h*, or with a force applied E from portion 140*c* applied to the rearward portion 110*d* to cause rocking in a direction A" toward the target object such that the energy application tool 110 is driven in direction A, as shown in FIG. 1*i*. The forces D and E may be applied by any appropriate method, such as, for example, by applying a magnetic force on the energy application tool 110, which may contain a magnetic or metallic element which may respond to the application of force from the drive mechanism 140. In general, the shape and arc of the rocking motions A' and A" may be designed such that the energy application tool 110 impacts the target object in a direction substantially perpendicular to the target object surface, as shown with the rocking A" into a substantially vertical orientation of the bent portion 110*c* around bend 110*b* in FIG. 1*i*. To reset the device 100 for a subsequent measurement, the portion 140*d* may apply a return force D, as shown in FIG. 1*h*, to cause rocking A' to return the energy application tool 110 to a withdrawn or resting state. In general, the interior of the device 100 may be adapted to allow for the rocking motions A' and A" without interfering with the energy application tool 110.

Figure 1L:
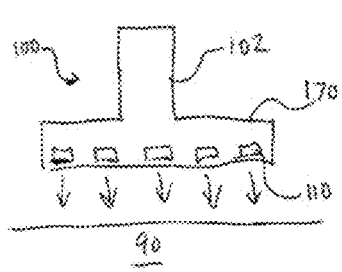
FIGS. 1l, 1m and 1n illustrate examples of arrays of energy application tools.
Figure 1M:
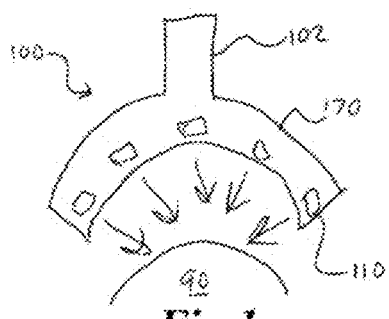
Figure 1N:
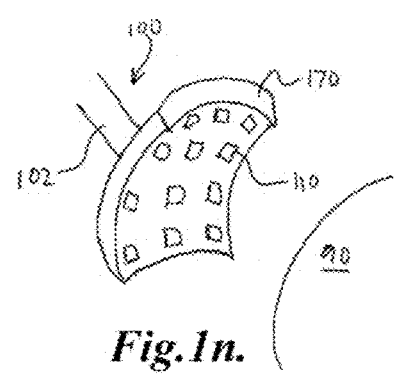
Figure 1J:
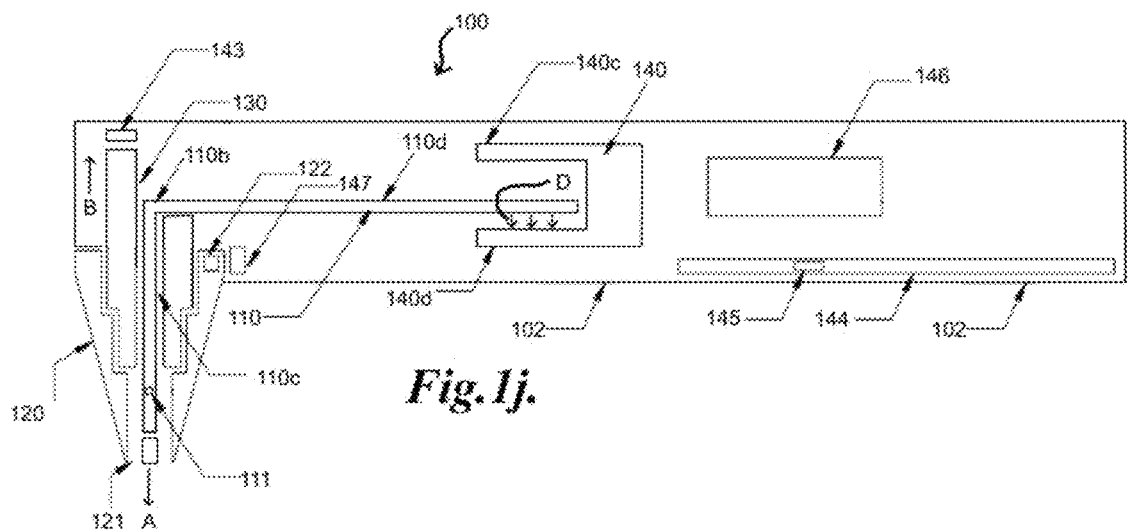
FIGS. 1j and 1k illustrate the motion of a vertically translating energy application tool.
Figure 1K:
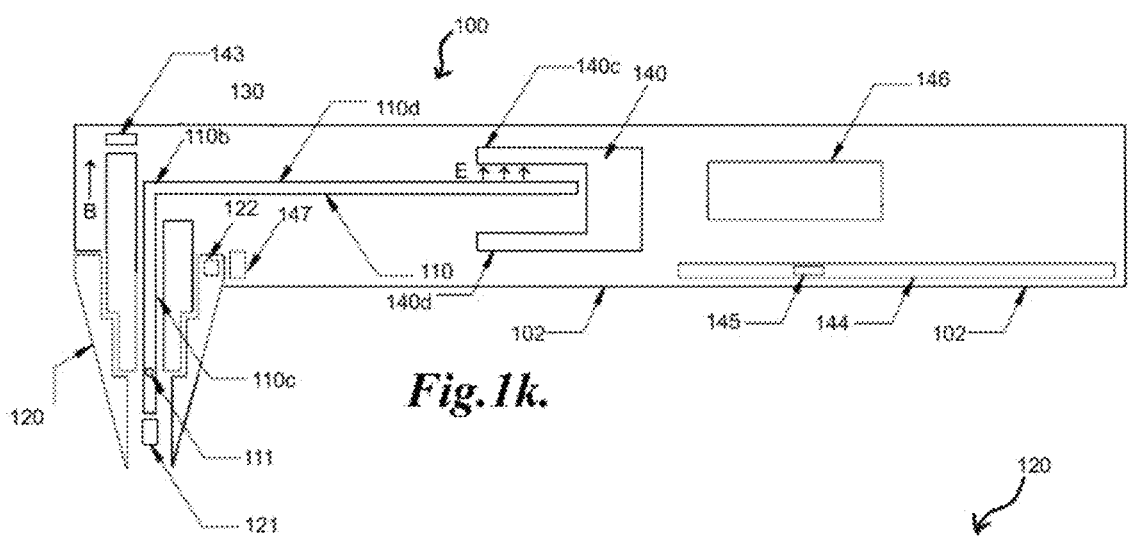

In some embodiments, the L-shaped energy application tool 110 may be translated with an external force applied from a drive mechanism 140, as shown in FIGS. 1*k* and 1*l*. For example, the drive mechanism 140 may apply alternating forces to the energy application tool 110 to cause it to translate between a withdrawn or resting state, such as with a force applied E from portion 140*c* applied to the rearward portion 110*d* to pull the energy application tool 110 away from a target object, as shown in FIG. 1*l*, or with a force applied D from portion 140*d* applied to the rearward portion 110*d* to cause to translate toward the target object such that the energy application tool 110 is driven in direction A, as shown in FIG. 1*k*. The forces D and E may be applied by any appropriate method, such as, for example, by applying a magnetic force on the energy application tool 110, which may contain a magnetic or metallic element which may respond to the application of force from the drive mechanism 140. In general, the energy application tool 110 may be guided or constrained such that it moves substantially only in the desired direction, such as with guide pins, rails, channels or any other appropriate feature. To reset the device 100 for a subsequent measurement, the portion 140*c* may apply a return force E, as shown in FIG. 1*l*, to return the energy application tool 110 to a withdrawn or resting state.

In some exemplary embodiments, the energy application tool 110 may generally include a tapping rod or impact rod, as illustrated in FIGS. 1, 1*d*, 1*e* and 11 with the linear rod-shaped energy application tool 110. In general, portions of the energy application tool 110 may be designed for delivery of the desired amount of energy, such as via impact, to the object and/or for carrying return energy for measurement. The energy application tool 110 may further be designed to interact with the drive mechanism 140, such as by including metallic, magnetic (e.g. ferromagnetic), conductive and/or other desirable portions or components, such as those that may be manipulated by magnetic fields and forces. The energy application tool 110 may also be designed, for example to decrease its overall mass or density, such as for easier propulsion by the drive mechanism 140 and/or for controlling the force of impact on the object.

To aid in the movement of the energy application tool 110, such as a tapping or impact rod, a support or bearing may be utilized that the energy application tool 110 may slide freely in, but is constrained from moving off axis, as shown with slide retainer 112*b* in FIGS. 1*d*, 1*e* and 11.

Generally, the impact force made by the energy application tool 110 on the object undergoing measurement may vary depending on the mass of the energy application tool 110, the distance traveled in contacting the object from an initial position and the angle of incline of the device 100 or the energy application tool 110 with respect to the horizontal.

Figure 8C:
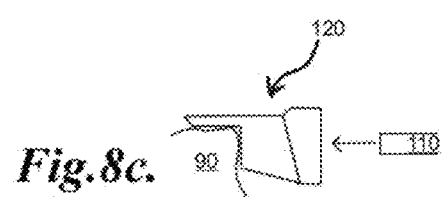
FIGS. 8c, 8d and 8e illustrate adapters for the device for orientations at a horizontal, a positive inclination and a negative inclination in measuring an object, respectively.
Figure 8D:
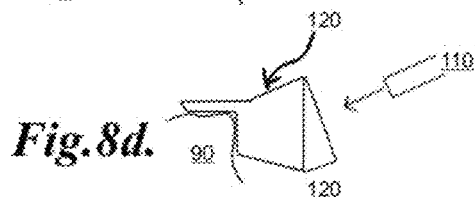
Figure 8E:
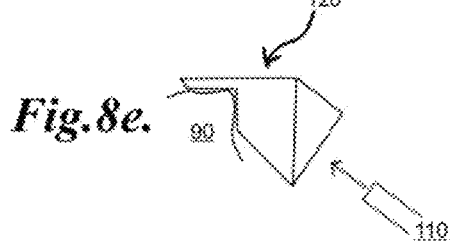
Figure 8:
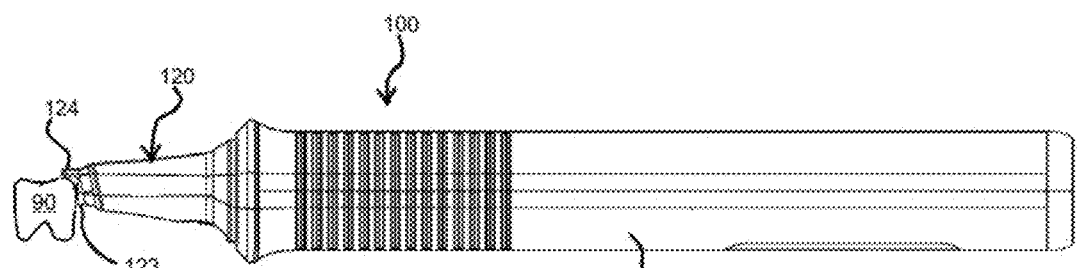
FIGS. 8, 8a and 8b illustrate the device of the present invention with a sleeve portion having a tab oriented at the horizontal, a positive inclination and a negative inclination in measuring an object, respectively.
Figure 8A:
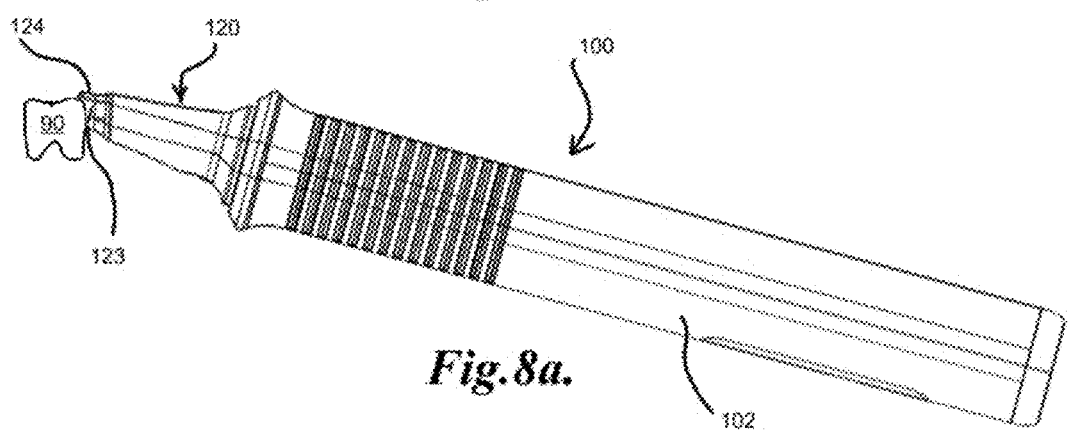
Figure 8B:
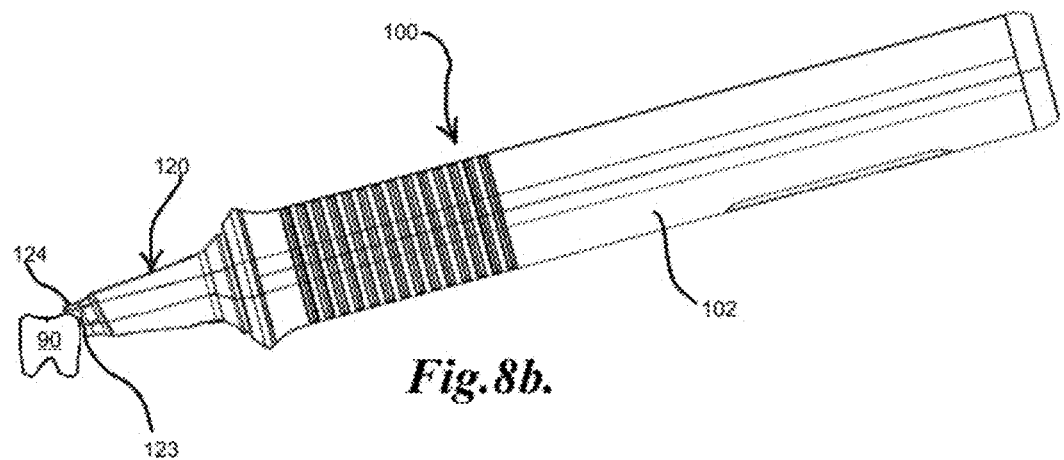
Figure 8F:
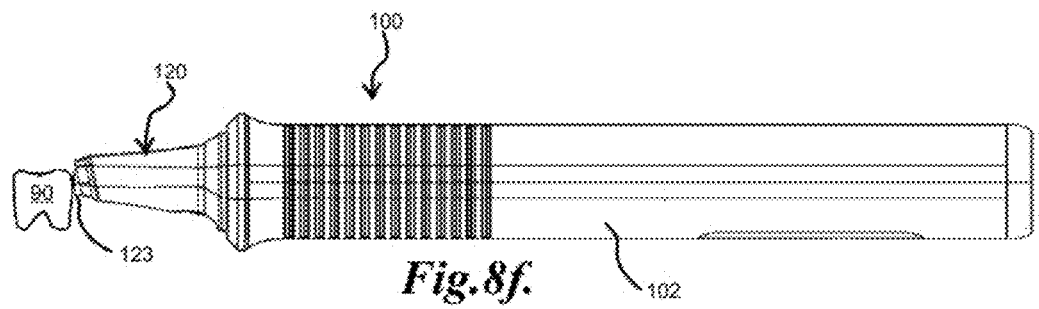
FIGS. 8f, 8g and 8h illustrate the device of the present invention without a tab on the sleeve portion oriented at the horizontal, a positive inclination and a negative inclination in measuring an object, respectively.
Figure 8G:
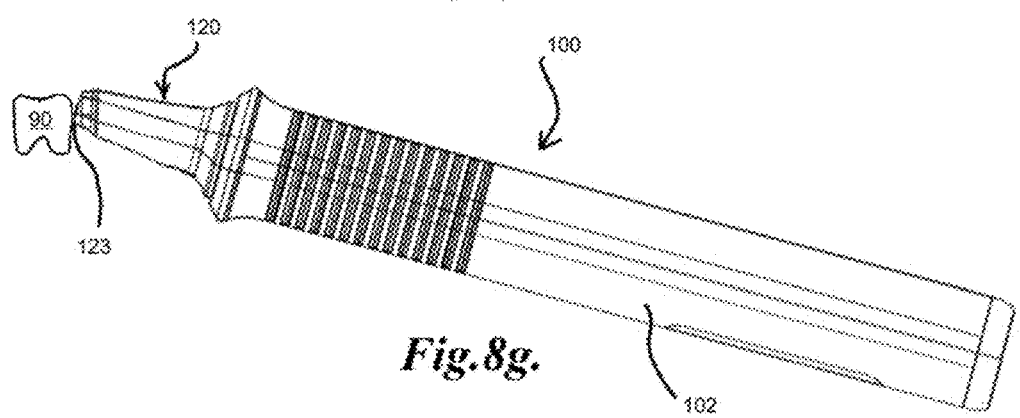
Figure 8H:
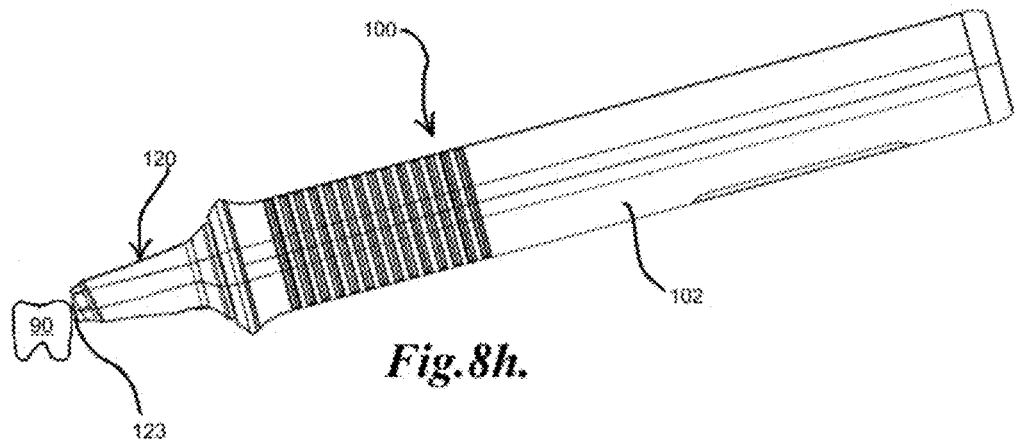

In some examples, for a given mass of the energy application tool 110 and other factors being equal, the impact force may be higher at a negative inclination from the horizontal, as illustrated with the device 100 in FIGS. 8*b* and 8*h* (with a tab 124 and without a tab 124 on the sleeve portion 120, respectively), than the impact force in a horizontal position, as shown with device 100 in FIGS. 8 and 8*f* (with a tab 124 and without a tab 124 on the sleeve portion 120, respectively), as gravity may contribute to the force at impact. The increase of the force contribution from gravity may generally increase with the degree of negative inclination until the device 100 reaches a vertical orientation with the energy application tool 110 pointing downward. In other examples, the impact force may be lower with a positive inclination of the device 100, as shown in FIGS. 8*a* and 8*g* (with a tab 124 and without a tab 124 on the sleeve portion 120, respectively), as gravity in the plus angle works against, rather than contributes to the impact force.

Generally an equivalent force of between 1-15 newtons may be used in application of energy to an object with the energy application tool 110. Since the low end of impact force may not be optimal, the device 100 may generally be placed in contact with the object undergoing measurement in a substantially horizontal position for better results, for example, by calibrating the system for the optimal amount of force exertion on the object. This may be rather restrictive in the ability to position the device 100. For example, some objects undergoing measurement may be in difficult to reach places, such as portions of the human mouth, and angling the device 100 may be needed. Therefore, in some instances, a higher equivalent force may be used, for example, 10-50 newtons for may be used on a device 100 to built-in some flexibility in positioning the device 100 on an object. Even at this higher impact force range, the lower end, i.e. when the device 100 is placed in an incline at a plus angle to the horizontal, as shown in FIGS. 8*a* and 8*g*, may be lower than the impact force needed for generating an optimal measurement, while at the higher end, the force may be much higher than desired in some instances, such as in the position illustrated in FIGS. 8*b* and 8*h*. However, this built-in capability of a higher force just in case there is a need to position the device 100 at an angle to the horizontal may be undesirable when used in some situations, for example a dental setting. For example, an equivalent impact force range of between about 20-45 newtons may need to be used, for example, in a dental setting, such as with human teeth or other objects, as illustrated in FIGS. 8, 8*a*, 8*b*, 8*f*, 8*g* and 8*h* with tooth 90, to obtain better results with some flexibility for positioning, and such force may be rather uncomfortable for the patient.

In exemplary embodiments of the present invention, the system may be utilized to exert a substantially the same impact force on the object in various angles from the horizontal, as if the device 100 is operating horizontally. Thus whether the device 100 is operating between about plus/minus 45 degrees, more for example, about plus/minus 30 degrees, the device 100 may generate about the same amount of equivalent impact force, for example, about 20-30 newtons.

In some embodiments, the device 100 may employ a set of different adapters or features to set a particular angle between the energy application tool 110 and the object 90, such as, for example, to enable highly reproducible and/or consistent angles for measurements, such as to create averaged data sets. FIGS. 8*c*, 8*d* and 8*e* illustrate different embodiments of a sleeve portion 120 with angled features to change the angle of energy delivery from the energy application tool 110, such as approximately perpendicular to the object 90 in FIG. 8*c*, a positive angle (e.g. 45 degrees or less) to the object 90 as in FIG. 8*d*, or a negative angle (e.g. −45 degrees or more) to the object 90 as in FIG. 8*e*. The set of adapters or features, such as the sleeve portions 120, may be switched out when measuring an object 90, for example, to perform measurements at different angles to create a more complete data set or a data set with greater variation in measurement locations.

An inclinometer may be present, for example, on or within the device 100, such as in connection with the energy application tool 110, which may trigger an audible warning when the device 100 is held against the object and is outside of the angular range of operation, for example, for a tapping rod, it may trigger the warning when it is plus/minus approximately 45 degrees or more, more for example, plus/minus about 30 degrees or more from the horizontal, at which point, the angle may substantially affect the result of the measurement of the object.

Figure 4:
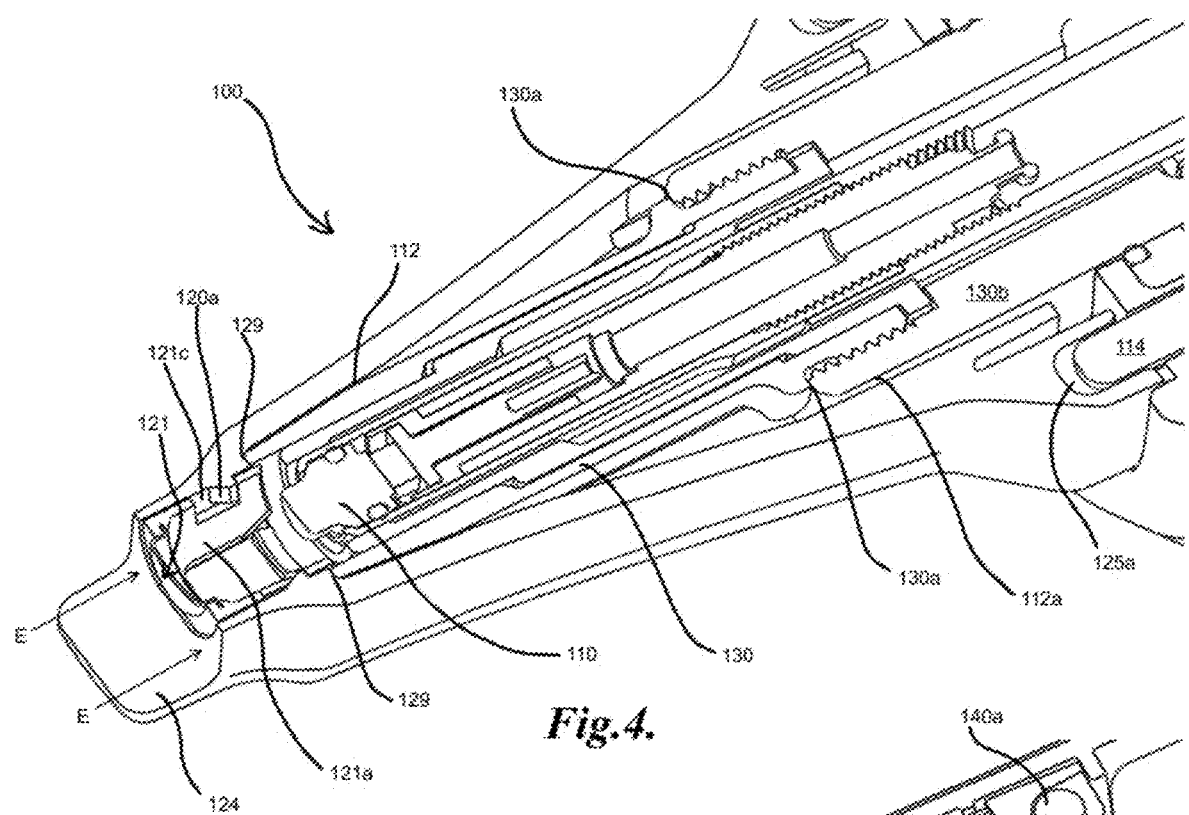
FIGS. 4, 4a and 4b illustrate transfer of contact force from an object to a force sensor.

In one embodiment, if the device 100 is oriented such that the axis of operation is greater than about 45 degrees, more for example, greater than about 30 degrees from the horizontal position, and the device 100 is activated when a contact force is sensed on the object contacting portion of the sleeve portion on the object, it may result in a warning sound being emitted by a speaker located on the device 100, such as the printed circuit board (PCB) 108 within the device 100, as shown in FIGS. 1*d* and 11. In another embodiment, the warning sign may be given by a light signal, which may be a flashing light, or a light of a certain color, which may be emitted from a light source, such as the light source(s) 114*a* or through the sleeve portion 120 with light carried to it through light pipes 114, as illustrated in FIG. 4. In such circumstances, the percussion action, if the device 100 is a percussion instrument, will not begin until the device 100 is returned to an acceptable angle. In some instances, if the percussion action has started when the above-mentioned departure from the range is detected, the device 100 may not actually stop operation, but may simply be sounding an alarm, so that corrections may be made.

In some embodiments, the inclinometer may include an accelerometer, such as a 3-axis device which measures gravity on all three axes, the X, Y and Z axes, a two-axis device or a one-axis device. In one embodiment of the invention, the device 100, such as a handpiece, may include software for measuring the value of the Y-axis (i.e. vertical) gravitational force (G-force) from input provided by the inclinometer. For example, if the G-force for the Y-axis is greater than about the plus/minus, say, 15 degrees threshold, the handpiece may make an audible noise, such as beeps, or a light signal such as a flashing light, or a light of a certain color. If the G-force for the Y-axis is greater than the 30-degree threshold, the handpiece may beep faster, or if a light signal such as a flashing light, it may be a faster flashing light. The accelerometer may be sampled every, say, 100 ms. Five consecutive valid readings may be needed (500 ms) to trigger a threshold and thus the beep or the flash, etc. The thresholds for both the 15 and 30-degree thresholds may be determined empirically.

For example, for a device 100 without the features of the present invention, during operation, if the impact force is about 26 newtons at plus 15 degrees from the horizontal, the impact force will be about 32 newtons at a horizontal position, and at minus 15 degrees from the horizontal, the impact force will be about 35 newtons. With the present invention, all impact forces at all the above mentioned angles may be at about 25 newtons or whatever optimal impact force programmed to exert. This may be accomplished by, for example, varying the application of energy from the drive mechanism 140 to the energy application tool 110 to accommodate the angle of impact. Examples of variations to the application of energy from the drive mechanism 140, such as an electromagnetic coil as illustrated in FIG. 4, may include varying the power applied to the coil (e.g. voltage, current or both), coil drive times (the length of time the coil is energized or activated), coil delay times (the time between driving activities), number of coil energizations (i.e. number of drive pulses applied), polarity of the coil and/or a combination thereof. This varying power, drive times, polarity and delay times may be managed through varying the firmware settings for power, drive time, number of drives, polarity and drive delay of the energizing of the coil for the desired results. In general, varying the power supplied to the coil may alter the strength of the magnetic field it generates, with a higher field generally imparting more energy to the energy application tool 110 and a lower field generally imparting less. The varying of the coil drive time may generally affect the energy application tool 110 with longer duration imparting more total energy and a shorter duration imparting less. The varying of the coil delay times may generally alter the rate of acceleration of the energy application tool 110. The varying of the number of coil energizations (drives) may affect by increasing the total amount of energy applied with higher drives and decreasing the total amount of energy applied with lower drives. The polarity changing will generally apply motion to the energy application tool 110 in opposite directions and thus an opposite polarity drive may decelerate the energy application tool 110. Without being bound to any particular theory, multiple variations may be employed to achieve the desired result and the firmware may be designed to select a particular solution or to select an optimal solution for certain instances.

In some embodiments, the firmware may be adapted to vary only certain settings of the drive mechanism, such as, for example, drive times, number of drives, polarity and drive delays, while keeping other settings constant, such as, for example, power. This may be desirable as some settings may be more difficult to adjust, such as power settings which may be relatively unadjustable due to a particular power source, such as a battery, which may generally only output power at a given level and requires more extensive componentry or circuitry to make adjustable.

In other embodiments, the energy application tool 110 may include other forms of energy application, such as, for example, electromagnetic energy application, sound or acoustic energy application, and/or any other appropriate form of energy application that may generate a measurable return signal. For example, acoustic or sound energy may be applied, such as through a sound transducer (e.g. ultrasound transducer, speaker or other acoustic element). In some embodiments, the energy application tool 110 may also serve as both the energy application and the sensing of the return signal, such as with ultrasonic transducers.

In some embodiments, a handpiece or device 100 may employ a plurality of energy application tool 110, such as in an array. FIGS. 1*l*, 1*m* and 1*n* illustrate examples of arrays 170 of energy application tools 110, such as in a straight array in FIG. 1*l*, a curved or arced array in FIG. 1*m* and a conforming surface array in FIG. 1*n*. Arrays of energy application tools 110 may be utilized to interrogate a larger area or volume for measurement or may be used to interrogate an area from multiple locations or angles. In some embodiments, arrays may also be utilized in temporally controlled manners to perform phased array measurements. For example, arrays of energy application tools 110 may be triggered at differing times to create phased effects, such as through constructive interference patterns with ultrasonic waves to direct energy at a particular location without moving the energy application tools 110. In embodiments where the object is large, measurement at different locations of the object, for example, impacting at a plurality of portions of the object may allow better evaluation of the structural properties that are better representations of the object.

In exemplary embodiments, the handpiece 100 may further house a sensing mechanism 111 for detecting characteristics of the effects from the impact of the energy application tool 110 with the object. In general, the sensing mechanism 111 may be physically coupled to, functionally coupled to or otherwise in contact with the energy application tool 110 such that it may detect characteristics of the impact. In some embodiments, the sensing mechanism 111 may include a piezoelectric sensing element which may generally produce an electrical signal or change in response to mechanical energy, such as a change in pressure on the piezoelectric sensing element, may be utilized for analysis of the object. A piezoelectric wire may, for example, be loaded into the energy application tool 110, as shown with the sensing mechanism 111 being inserted in FIG. 1*e*. The sensing mechanism 111 may also include other forms of sensing elements, such as, for example, a linear variable differential transformer which may sense the position of the energy application tool 110 due to changes in voltage in the transformer due to positioning of the energy application tool 110 which may be metal or otherwise affect the induction in the transformer, accelerometers, resistive pressure sensors, strain gauges, and/or any other appropriate type of sensor or combination of sensors. In general, the position of the sensing mechanism 111 or portions thereof may be determined for optimal sensing of the desired characteristic. For example, a piezoelectric sensing element may generally be placed as close to the point of impact as practicable, such as near the tip that impacts the object, such that a greater amount of physical deformation of the energy application tool 110 may be detected. The sensing mechanism 111 may be adapted for measuring the deceleration of the energy application tool 110 upon impact with an object during operation, or any vibration caused by the impact. The sensing mechanism 111 may detect changes in the properties of the object and may quantify objectively its internal characteristics. Data transmitted by the sensing mechanism 111 may be processed by a system program, to be discussed further below. The sensing mechanism 111 may be disposed in or proximate to any appropriate portion of the energy application tool 110, such as proximate to the end contacting the object, as shown in FIGS. 1, 1*f*, 1*h*-1*k*. The sensing mechanism 111 may also be located further back, such as near or just after the bend 110*b* of the energy application tool 110 where the bent portion 110*c* transitions to the rearward portion 110*d* in L-shaped energy application tools 110, such as in FIGS. 1*f*, 1*h*-1*k*. The sensing mechanism 111 may also generally be a separate sensor from the force sensor 143 of FIGS. 1, 1*d*, 1*e*, 1*f*, 1*h*, 1*i*, 1*j*, 1*k*, 4*a*, 4*b*, 11, 11*a*, 11*b* and 11*c*, which may be utilized to detect the contact force of the handpiece 100 against an object, rather than detect forces on the energy application tool 110. A force sensor 143 may include any appropriate sensor for measuring the force being exerted from the contact of the handpiece 100 against an object by the user, such as, for example, a piezoelectric sensor, a force sensing resistor (e.g. a Shunt-mode FSR), a strain gauge or multiple strain gauges (e.g. mounted onto a cantilever(s) that flex in response to the applied force), linear position sensors (e.g. optical position sensors, magnetic field or other than can detect a position change of a component pressing against a spring or other element where the linear position change corresponds to the applied force), and/or any other appropriate type of force sensors In some embodiments, communication between the drive mechanism 140 or portions of the drive mechanism, for example, the energy application tool 110, the sensing mechanism 111 or the electronics assembly 144 may be via a lead or line of electrically conductive, insulated wire which may be wound spirally in a concentric fashion around the tapping rod and has spring-elastic properties. This may also allow a minimum space requirement with respect to the line management. For example, a strand of wires wound concentrically around the energy application tool 110 may be utilized to carry signals to and/or from the sensing mechanism 111. One purpose of concentrically winding the wire is to minimize the stress on the wire from repeated forward and back movement of the energy application tool 110. In some embodiments, a helical spring, which may be formed by the spirally wound wire, may help to avoid or prevent looping or twisting of the wire connection.

In another embodiment, the communication between the drive mechanism 140 and the energy application tool 110 may be transmitted wirelessly via any suitable wireless connections. In one example, the energy application tool 110, such as the tapping rod may be propelled forward by energizing the electromagnetic coil and creating a magnetic field that repels the magnet in the end of the energy application tool, for example, the tapping rod. The rod is retracted by reversing the polarity of the voltage applied to the electromagnetic coil. The magnet may also serve to hold the rod in its retracted position when the electromagnetic coil is not energized, through its magnetic attraction to the steel core of the coil.

A helical spring, if present, may be composed of stranded wires having two twisted individual wires or of a coaxial line. In its loaded condition, the spring may be compressed to such a degree that the force of its prestress corresponds to the frictional force and opposes this frictional force during the forward motion of the energy application tool, for example, the tapping rod from the retracted position to the extended position, or from a substantially parallel position to the longitudinal axis of the housing to a position making an acute angle with the axis at a pivot. The prestressed path of the spring may therefore be far greater than the stroke of the energy application tool, for example, the tapping rod so that spring power remains substantially constant over the entire stroke of the tapping rod. Any undesirable frictional force of the bearings of the mounting mechanism for the tapping rod during the forward motion may also be substantially compensated by this spring.

The handpiece 100 may include features, such as in the electronics assembly 144, which may generally control the drive mechanism 140 and may also store, process and/or transmit data from the sensing mechanism 111. The electronics assembly 144 may include, for example, wired or wireless transmission features to relay data to a computer or other device for analysis or viewing. In some embodiments, the electronics assembly 144 may interface with an outside device, such as via electronics contacts 113 in FIG. 1c, to transmit data.

As illustrated in FIGS. 1d and 1e, the sensing mechanism 111 may connect to the electronics assembly in a wired manner, such as through a wired connection carried in a conduit 111a, which may be flexible, for example, to accommodate the movement of the energy application tool 110. The conduit 111a may also provide protection to the wired connection from moving components in the handpiece 100, such as the energy application tool 110.

As noted above, the handpiece 100 may be tethered to an external power supply or be powered by an electrical source included inside the housing 102, such as the power source 146. If powered by an electrical source inside the housing 102, the power source 146 may or may not be rechargeable. If rechargeable, a base charging station may be used.

Figure 5:
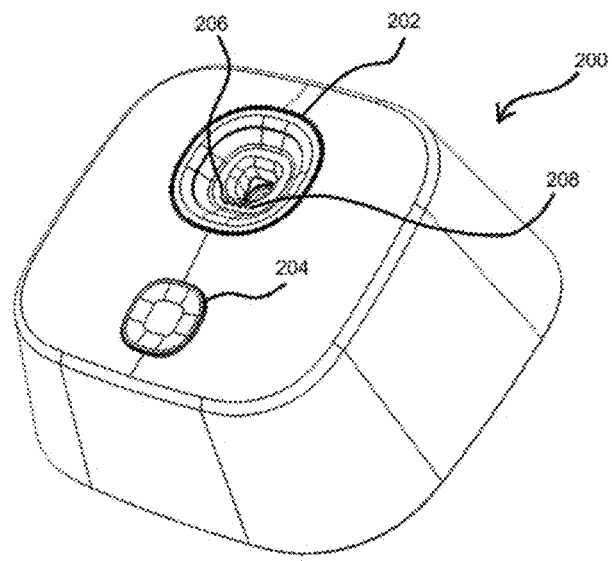
FIGS. 5 and 5a illustrate a base unit for a handpiece.
Figure 5A:
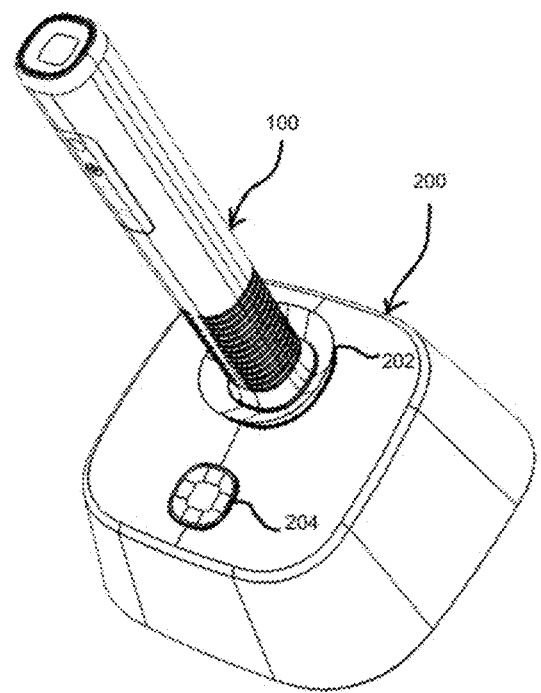

FIGS. 5 and 5a illustrate a base station 200 which contains a handpiece receptacle 202 for receiving the handpiece 100. The base station 200 may be a separate independent station or it may be part of the system of the present invention. For an independent charging station, any existing station may be applicable. The charging mechanism may be wired or wireless. For these charging base, only electrical current to charge the device may be provided. For a base station that may be part of the system, more than electrical current to charge the device may be provided.

The present invention still further relates to a base station that may be part of the system of the present invention and may be plugged into the computer, for example, a PC via a USB cable. This connection may provide both data transfer between the PC and the base station, and electrical current to charge the device during the charging process when the device is docked. In this way, the base station may also serve to act as a wireless transceiver for the PC in the communication with the wireless transceiver in the device.

FIG. 5 illustrates an example of a base station 200 with base electronics contacts 206 which may contact and transfer data through corresponding contacts on the handpiece 100, such as the electronics contacts 113. The base station 200 may further supply charging to the handpiece, such as through base power contact 208, which may charge by contact with a corresponding feature on the handpiece 100, such as power contact 113a.

It may be desirable for each device to be accompanied by its own charging base station. This may avoid the possibility of the wrong device communicating with the wrong base station, in a multiple device environment. This may be important in any testing setting, for example, a dental office. For example, each handpiece 100 may have an accompanying base station 200.

During preparation of the system just prior to performing a measurement on an object, the handpiece 100 may be docked in the base station 200 to pair that device with that base station 200 as part of the usage protocol, for example, prior to starting a patient testing session in a dental office. The usage protocol may be controlled by the software. The pairing may also be accomplished by placing a base station 200 and a handpiece 100 into a pairing mode, such as via controls 204 and/or a programming button 144a as shown in FIGS. 1d, 5 and 5a.

For the embodiments where the device may be equipped with a disposable feature or assembly described above, such as a sleeve 120, the disposable portion is generally removed from the device prior to placing the device in the base station 200. In other embodiment, the disposable portion may be physically accommodated in the interface between the device and the base station 200.

In some exemplary embodiments, the handpiece 100 may include a housing with a hollow interior with an open end, as illustrated in FIGS. 1a, 1b and 1c with housing 102, applicator end 102a with aperture 102c and distal end 102b. In general, the energy application tool 110 or at least a portion thereof may emerge from an opening in the housing 102, as shown in FIG. 1c with aperture 102c. The housing 102 may also include handling features, such as gripping features 103 as illustrated. The housing 102 may also include other features such as to access portions of the interior, such as battery access cover 104.

The housing 102 may include multiple portions or parts, such as illustrated in FIGS. 1d and 11 with upper and lower housing clamshells 102d, 102e, forward end cap 105, and base end cap 106. In general, the components of the handpiece 100 may be arranged within the housing 102, such as substantially axially arranged with the energy application tool 110 forming the approximate center of the formation with other components concentrically arranged.

The forward end cap 105 may include apertures for portions of the device to emerge, such as the aperture 102c to allow the energy application tool 110 and/or its associated components to emerge.

In another aspect of the invention, the system may include features for aiding the stable, consistent and/or reproducible positioning of the energy application tool 110 relative to an object to be measured, which may also be conducted in a manner that reduces cross-contamination or other sanitization issues.

In some exemplary embodiments, a sleeve portion as discussed above and/or below may be included that may be present or positioned near the portion of the energy application tool 110 that contacts and/or impacts the object and utilized in conjunction with the handpiece 100 and associated components discussed above. FIGS. 1, 1a, 1b, 1d and 11 illustrate a sleeve 120 disposed near the applicator end 102a of the housing 102. In some embodiments, the sleeve portion, such as the sleeve 120 may be integral to the handpiece 100 or mounted to the handpiece 100 in a permanent or semi-permanent manner, such as for multiple uses. The sleeve portion may also be a removable and/or disposable piece which may be replaced, such as between different patients and/or procedures to aid in reducing cross-contamination or other sanitization issues, such as the need to sanitize/sterilize the portions of the system that contact a patient.

Figure 2:
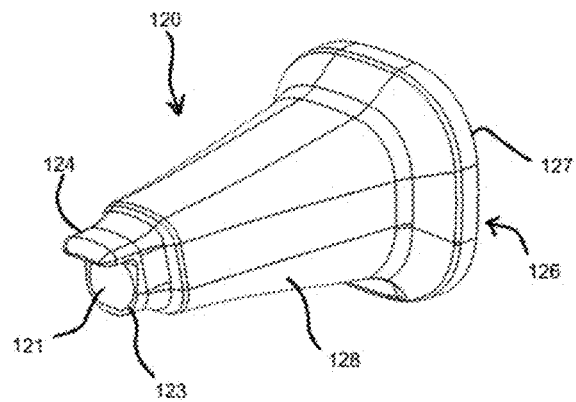
FIG. 2 illustrates a sleeve portion with a tab.
Figure 2A:
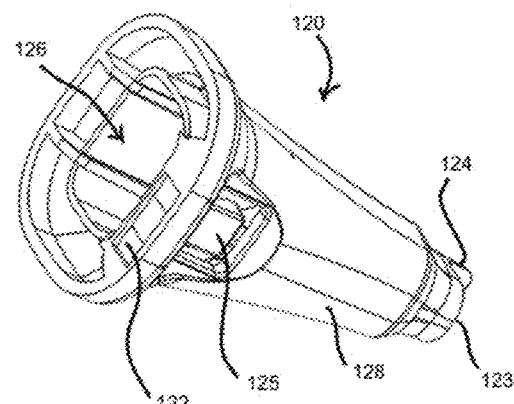
FIG. 2a illustrates a sleeve portion with a security feature and an attachment feature.

FIGS. 2, 2a, 2b and 2c illustrate embodiments of the sleeve 120 which are separable pieces from the rest of the handpiece 100. The sleeve 120 may generally couple to the handpiece 100 or portion thereof through any appropriate form of connection, such as, for example, any threaded attachment, friction fit, mating bayonet formations, tongue and groove type formations, snap fit, clips, internesting pin and pinhole formations, latches and other interconnecting structures. Any of the connections mentioned above may be secure and releasable. For example, an interconnecting assembly may be disposed at the end of the handle housing, for example of a hand held device, where connection occurs, which may be configured to releasably connect the handle and the sleeve portion. FIGS. 1b and 2a illustrate a clip 125 on the sleeve 120 which may clip onto a portion of the handpiece 100, such as the sleeve mount 112a in FIGS. 1c, 1d and 11. In one embodiment of the invention, the sleeve portion, such as the sleeve 120, may be a non-reusable and disposable assembly or feature in a healthcare setting, such as a dentistry office or similar. As noted above, the disposable feature or assembly is for aiding in eliminating or minimizing contamination of the object undergoing the measurement through transfer from the system or cross-contamination from previous objects undergoing the measurements, without having to carry out a decontaminating process prior to moving to a different test object. To ensure that such features or assemblies once used are not reused, the disposable features or assemblies may be programmed to be one use. In some embodiments, a computer chip may be used. The chip may be present on a PCB located on the disposable feature or assembly, for example, in the back of the disposable assembly, may serves to ensure that once used, it cannot be or is not reused, so that any unwanted material may not be transferred from one patient to another. FIGS. 1 and 2a illustrate a device coupled to the sleeve 120 which may be utilized to interface with the electronics of the handpiece 100, such as via electronic interface 142, which may utilize contact pins such as electronic contacts 113 in FIG. 1c, or other forms of electronic interface, such as Radio Frequency ID (RFID), Near Field Communication (NFC), Bluetooth, and/or any other appropriate form of interface.

The electronic interface 142 may include a PCB, such as illustrated with sleeve mount PCB 108 and its retainer 107 in FIGS. 1d and 1l. The electronic contacts 113, if utilized, may emerge from the housing 102 through apertures in the forward end cap 105. Signals and/or power may be conveyed from the electronics assembly 144, such as through a wired connected, as shown in FIG. 11 with connector wire 108a.

When a disposable feature or assembly is coupled to the device, the chip in the assembly or feature is interrogated by the device with a challenge and response system to ensure authenticity. Once authenticated, it is permanently marked as 'used'. If a used assembly or feature is placed on the device again, whether it is the same device or a different one, the challenge and response will fail, and the device will not be able to function as intended. In another embodiment, a timeout function may also be used to prevent the reuse of the disposable assembly or feature after a certain period of coupled time. In a further embodiment, the chip as well as the timeout function may be used for further insurance. In yet a further embodiment, the attachment mechanism of the disposable feature or assembly may include a part that once removed from the device is either snapped off or is warp to render it no longer attachable to a device. For example, the clip 125 in FIG. 2a may be adapted to snap off when the sleeve 120 is removed.

According to another embodiment, the sleeve portion, such as the sleeve 120, may be a limited reusable and disposable assembly or feature in a healthcare setting, such as a dentistry office or similar. For example, the disposable feature or assembly may also be autoclavable, even for a limited number of time.

In general, the sleeve 120 may protrude from the applicator end 102a of the housing 102 for a distance substantially coextensive with the end of the energy application tool 110 during measurement and may extend at least as far as the extended or propelled state of the energy application tool 110 as discussed above. Thus, the length of the sleeve portion 120 may be somewhat dependent on the length of protrusion of the extended energy application tool 110.

In some embodiments, as illustrated in FIG. 1f, the sleeve portion may be attached to or at the end of the housing 102 and being substantially perpendicular to it when the energy application tool 110, for example, a tapping rod, moves from being substantially parallel to making an acute angle with the longitudinal axis of the housing 102 at a pivot 110a when in operation. The sleeve portion may be substantially cylindrical in shape. In a further embodiment, the sleeve may be an extension of the housing and being of substantially a half cylindrical shape to allow the energy application tool, for example, the tapping rod to freely move when the tapping rod moves from being substantially parallel to making an acute angle with the longitudinal axis of the housing in operation. Using this system, measurements may be undertaken at locations which are relatively inaccessible such as, for example, in the molar area of a patient's teeth.

The sleeve 120 may generally include an object contact portion 123 which may be utilized to rest or press against the surface of an object, such as to stabilize and/or aid in repeatable positioning of the handpiece 100 against the object during a measurement. The sleeve portion may be substantially cylindrical and/or conical in shape with a hollow interior, as shown with the sleeve hollow portion 128 with a base portion 127 having an opening 126 where the energy application tool 110 may enter. The object contact portion 123 may generally form an aperture through which the energy application tool 110 may access the object. The size of the aperture may be varied, such as to provide a larger platform to rest against the object, as shown with the smaller aperture formed in the object contact portion 123 in FIG. 2f, or to provide a larger aperture, which may accommodate more varied object surfaces, as shown with the varied surfaces in FIGS. 3 and 3a.

In some embodiments, the aperture of the object contact portion 123 may further include a feature, for example, a contact feature, for contacting the object at an outer surface and the energy application tool 110 on an inner surface such that it may prevent direct contact between the energy application tool 110 and the object. This may be desirable to aid in preventing any contaminants or other sanitization concerns from moving between the object and the energy application tool 110 by providing a barrier. This may, for example, enable repeated use of the energy application tool 110 without cleaning/sterilizing/sanitizing it between, for example, different patients. The feature, such as the contact feature 121 as illustrated in FIGS. 1-1b and 2, 2b and 2c. In general, the contact feature 121 may be flexible, deformable and/or otherwise adapted to transmit the forces to and from the energy application tool 110 and the object during a measurement with minimal interference, attenuation or other undesired effects.

Figure 2B:
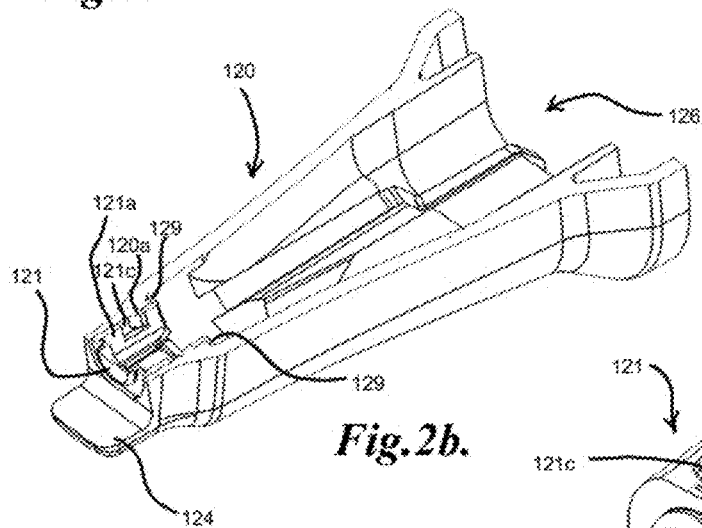
FIG. 2b illustrates a perspective cross-sectional view along a long axis of a sleeve portion with a contact feature.
Figure 2D:
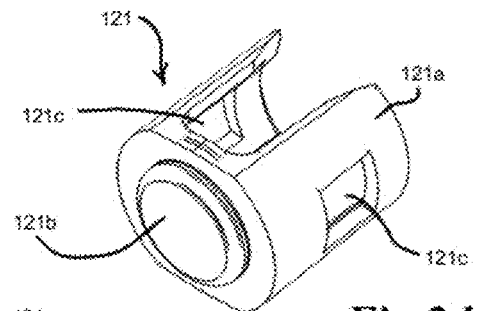
FIGS. 2d and 2e illustrate contact portions of a sleeve portion with movable or deformable portions.
Figure 2C:
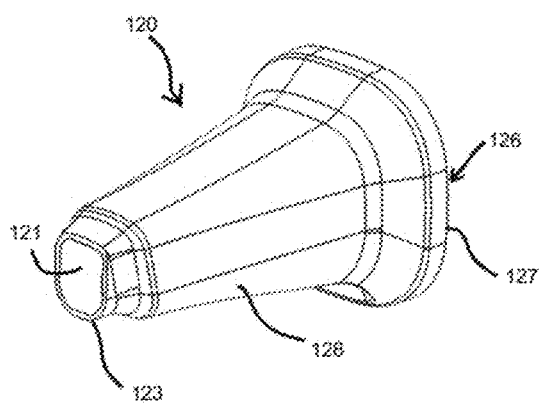
FIG. 2c illustrates a sleeve portion without a tab.
Figure 2E:
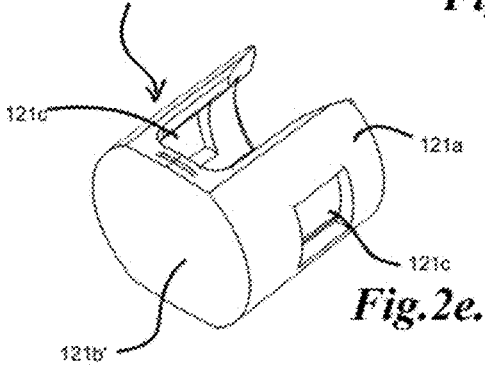
Figure 2F:
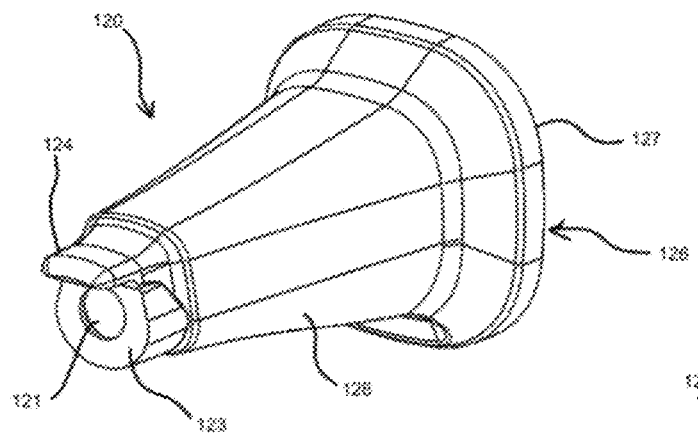
FIG. 2f illustrates a sleeve portion with a tab and enlarged contact surface.
Figure 2G:
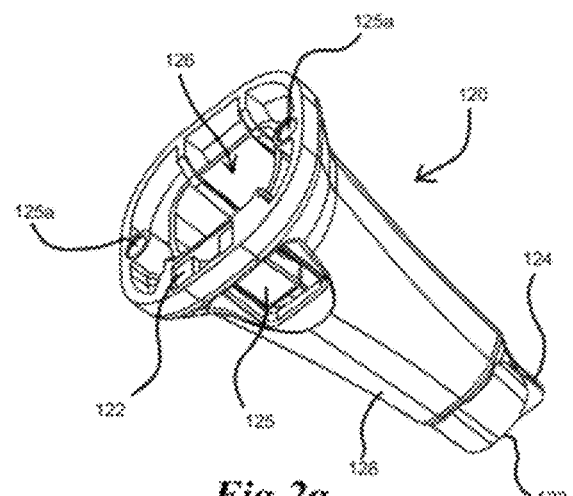
FIG. 2g illustrates a sleeve portion with a security feature, lighting interfaces and an attachment feature.
Figure 2H:
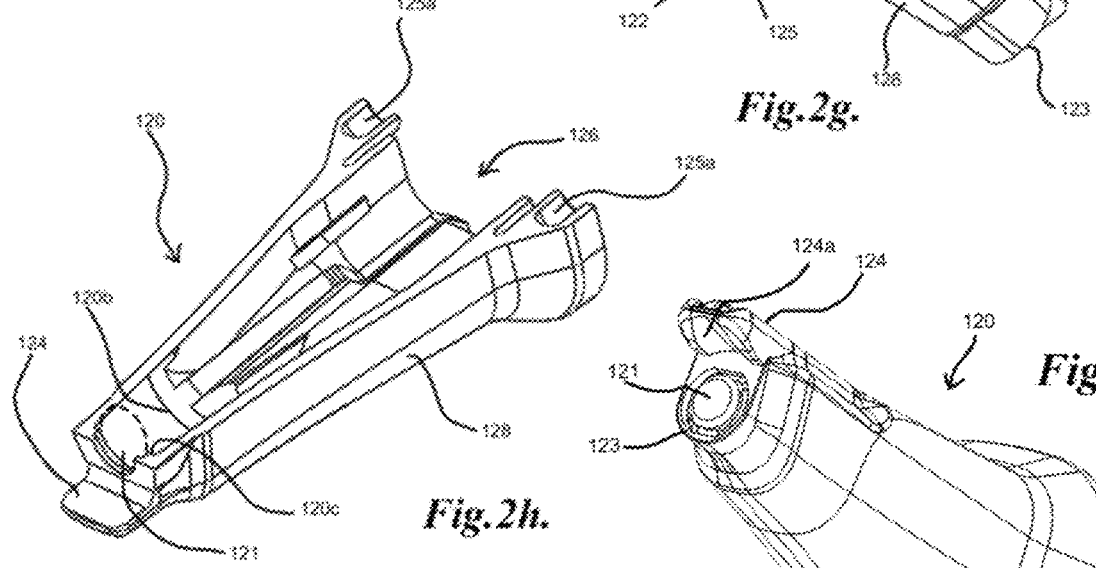
FIG. 2h illustrates a perspective cross-sectional view along a long axis of a sleeve portion with a contact feature and lighting interfaces.

In some exemplary embodiments, the contact feature 121 may be a separate component from the rest of the sleeve 120, as illustrated with the contact feature 121 in FIGS. 2b, 2d and 2e. A separate contact feature 121 may be desirable, for example, such that it may move at least semi-independently from the rest of the sleeve 120, as discussed further below. The separate contact feature 121 may be slidably and/or otherwise translatably disposed in the sleeve 120, as illustrated in the cross-sectional view of FIG. 2b, with the contact tubular portion 121a may rest in the sleeve 120, such as with a semi-frictional fit such that it is partially retained but may still move. The contact tubular portion 121a may also include features which may interact with corresponding features of the sleeve 120, such as to provide a limited range of motion, as illustrated with slots 121c and stop tabs 120a. In other embodiments, the contact feature 121 may be constrained by stops, ridges, bumps or other obstacles to prevent movement beyond a desired range along the longitudinal axis of the sleeve 120, such as illustrated with movement stops 120b, 120c in FIG. 2h.

In some embodiments, the contact feature 121 may include a thin membrane portion which may be of a thickness, deformability and/or shape such that it produces minimal effects on the transmission of forces through it. FIG. 2d illustrates an embodiment of a contact feature with a movable contact portion 121a which may include a thin membrane or other layer, as shown with separate contact portion 121b, which may move and/or deform freely, such as a thin plastic film or metal foil. In some other embodiments, such as in FIG. 2e, the contact feature 121 may be formed with an integral portion which may deform, flex and/or otherwise transmit the forces of the energy application tool 110, such as with a flexible plastic forming the contact feature 121 with a deforming contact portion 121b'. The movable contact portion 121a may also be formed to conform to the shape of the energy application tool 110, or vice versa, for optimal transfer of force/energy. In some exemplary embodiments, the movable contact portion 121a may be constructed from metallic foil, for example, stainless steel foil or sheet, and may, for example, be stamped and/or molded, for example, to conform to the end of energy application tool 110, such as with a domed shape. Some metallic foil or sheet, such as stainless steel and similar materials may be desirable, for example, due to its high strength characteristics such as rigidity or stiffness, ease of molding/forming, low dampening of transmitted energy or force through it, desirable properties for use in medical or dental applications and/or its commonality or low cost. For example, thin stainless steel foil or sheet, such as about 0.1 mm in thickness, may be utilized.

In other embodiments, the closed end of the contact feature 121 may be integral to the contact feature 121. For example, the contact feature 121 may be formed from a material which may be shaped into a tubular or ring structure with a closed end of a desired thickness, such as by stamping a metal (e.g. stainless steel, aluminum, copper, or other appropriate metal). For example, the contact feature 121 may take the form resembling a thimble or cup, with the closed end being of a thickness to provide deformable or movable characteristics.

For example, polymeric materials suitable for the, for example, membrane of contact feature may include any polymers having one or more of the following properties, including low coefficients of friction, high damping capacity, resorbable, biodegradable, water degradable, transparent, translucent and non-conductive.

For metallic material suitable for the, for example, foil or sheet, such as stainless steel and similar metallic material may be austenitic, work hardened, electro-polished, annealed prior to being formed into the desired shape, or superplastically formed into the desired shape.

Figure 3:
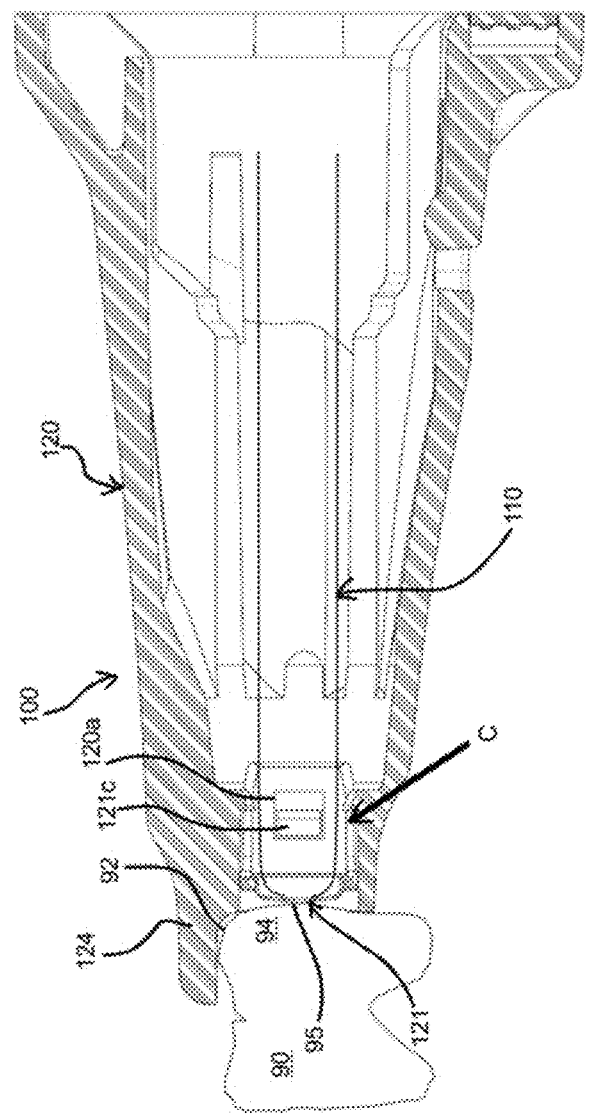
FIG. 3 illustrates contact of a sleeve portion with objects with an irregular surface with a convex portion.
Figure 3A:
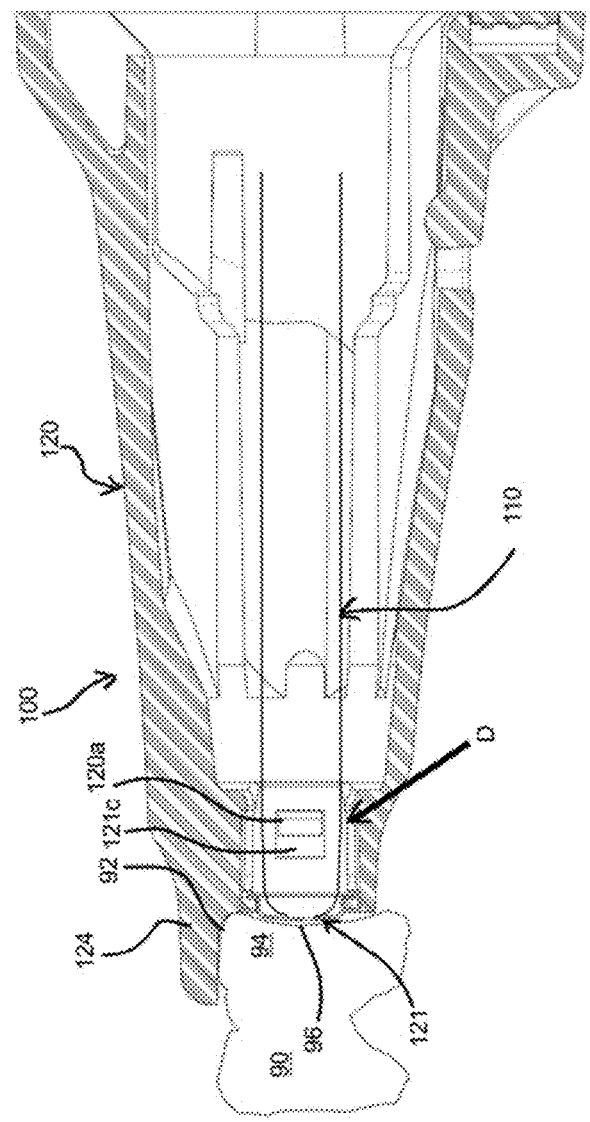
FIG. 3a illustrates contact of a sleeve portion with objects with an irregular surface with a concave portion.

In some embodiments, the contact feature 121 may be utilized to aid in producing consistent contact of the energy application tool 110 with the surface of an object, such as with surfaces with irregular or inconsistent surface features. For example, FIGS. 3 and 3a illustrate the use of the handpiece 100 with an object 90, where the object 90 has non-flat surface features, such as the object 90 with a convex contact surface 95 in FIG. 3 and another object 90 with a concave contact surface 96 in FIG. 3a. The object contact surface 123, which rests on the contact surface 94 of the object 90, may sit about an irregular or inconsistent surface feature which may provide a contact point for the energy application tool 110 either ahead or behind the plane of the object contact portion 123, as illustrated with the convex contact surface 95 protruding behind the plane in FIG. 3 and the concave contact surface 96 remaining ahead of the plane in FIG. 3a. With the contact feature 121 being movable with respect to the object contact surface 123, it may move and/or remain in an unextended or retracted position C, as shown in FIG. 3, to provide contact with the convex contact surface 95. Further, as shown in FIG. 3a, the movable contact feature 121 may move to an extended position D to provide contact with the concave contact surface 96. During a measurement, the energy application tool 110 may make an initial impact which may push the contact feature 121 to the proper position depending on the shape of the contact surface 94, and may remain substantially in that position or adjust to a different position in subsequent impacts or positionings of the handpiece 100. In general, the contact or impact of the energy application tool 110 may be controlled such that it does not cause deformation or damage to the object 90, but rather applies energy through properly accommodated contact as described.

In some exemplary embodiments, the sleeve 120 may include a feature for additional stability, such as providing stability substantially perpendicular or orthogonal to the direction A of the energy application tool 110. FIGS. 1a, 1b and 2-2b illustrate sleeve portions with a tab 124 protruding from the sleeve 120 near the object contact portion 123, such that when the object contact portion 123 is in contact with a surface of the object undergoing the measurement, the tab 124 may be resting on a portion of the top of the object, as shown with tab 124 resting on perpendicular surface 92 and object contact portion 123 resting on contact surface 94 of an object 90 in FIGS. 3 and 3*a*. The tab 124 and the object contact portion 123 may thus both assist in the repeatable positioning of the handpiece 100 with respect to the object 90 and the object contact portion 123 may be placed substantially at the same distance from the top of the object at perpendicular surface 92 during subsequent measurements for better reproducibility. As noted above, the object 90 may include an anatomical structure or a physical or industrial structure, though an anatomical structure is shown with a human tooth in FIGS. 3 and 3*a*.

Figure 2I:
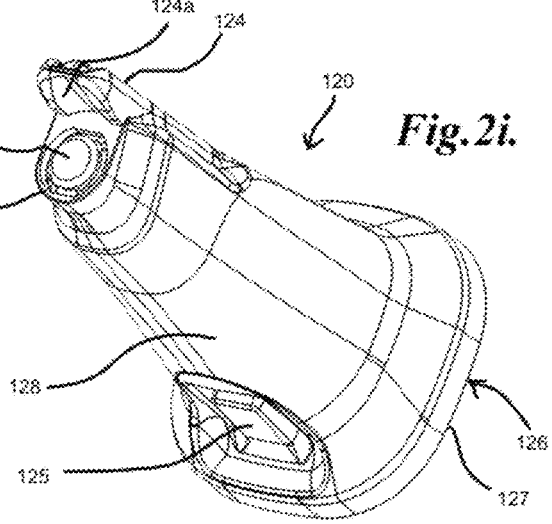
FIG. 2i illustrates a perspective view of a sleeve portion with a tab having a conforming formation.

In any of the embodiments, the corners of the tab 124 may be smooth or rounded or substantially smooth or rounded to avoid any catching on the object 90 they may be resting on. In other embodiments, the tab 124 may be smooth, though the corners may not necessarily be rounded. In any of the embodiments, the tab 124 may include at least one formation (e.g. a groove, channel, notch, indentation, etc.) so that when the object contact portion 123 is in contact with at least a portion of a surface of the object 90 undergoing the measurement, the tab 124 may be resting on a portion or surface of the object 90 and at least partially conform to a protrusion, bump or other raised portion of the surface of the object using the at least one formation, such as with the formation 124*a* illustrated as a groove in FIG. 2*i*.

In general, it may be desirable for the sleeve 120 or portions thereof to have sufficient rigidity such that it may consistently attach to the handpiece 100 and may not collapse during use. If multiple uses are contemplated, the sleeve 120 may generally be constructed to withstand multiple sterilization procedures, such as by autoclave, if desired, unless a disposable covering is used, as discussed below. In other embodiments, the sleeve 120 may be disposable, and if no sleeve is present, along with disposable coverings, if used, and thus may be constructed of any material that may be formed into a sleeve 120. Examples of appropriate materials may include, but are not limited to, for example, a polymer that may be molded, thermoformed or cast. Suitable polymers include polyethylene; polypropylene; polybutylene; polystyrene; polyester; polytetrafluoroethylene (PTFE); acrylic polymers; polyvinylchloride; Acetal polymers such as polyoxymethylene or Delrin (available from DuPont Company); natural or synthetic rubber; polyamide, or other high temperature polymers such as polyetherimide like ULTEM®, a polymeric alloy such as Xenoy® resin, which is a composite of polycarbonate and polybutyleneterephthalate, Lexan® plastic, which is a copolymer of polycarbonate and isophthalate terephthalate resorcinol resin (all available from GE Plastics); liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof. Some of these materials are recyclable or be made to be recyclable. Compostable or biodegradable materials may also be used and may include any biodegradable or biocompostable polyesters such as a polylactic acid resin (comprising L-lactic acid and D-lactic acid) and polyglycolic acid (PGA), polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers, and polyester/urethane resin. Some non-compostable or non-biodegradable materials may also be made compostable or biodegradable by the addition of certain additives, for example, any oxo-biodegradable additive such as D2W™ supplied by (Symphony Environmental, Borehamwood, United Kingdom) and TDPA® manufactured by EPI Environmental Products Inc. Vancouver, British Columbia, Canada.

In addition, any polymeric composite such as engineering prepregs or composites, which are polymers filled with pigments, carbon particles, silica, glass fibers, or mixtures thereof may also be used. For example, a blend of polycarbonate and ABS (Acrylonitrile Butadiene Styrene) may be used for the sleeve 120. For further example, carbon-fiber and/or glass-fiber reinforced plastic may also be used.

Synthetic rubbers may be, for example, elastomeric materials and may include, but not limited to, various copolymers or block copolymers (Kratons®) available from Kraton; Polymers such as styrene-butadiene rubber or styrene isoprene rubber, EPDM (ethylene propylene diene monomer) rubber, nitrile (acrylonitrile butadiene) rubber, and the like.

In some embodiments, the sleeve 120 may also be made of metallic and/or ceramic material(s) which may further be coated and/or treated with a suitable material, such as a polymer or composite as above. For example, a metallic and/or ceramic material may be utilized that may be substantially vibration dampening/absorbing/reflecting. A visco-elastic and/or other coating may also be employed such that vibrations and/or other mechanical energy may not translate into metallic and/or ceramic components of the sleeve 120.

In one embodiment, titanium and titanium alloys such as nickel-titanium, may be used for the sleeve 120, or components/portions thereof.

In a further aspect of the invention, the system may include features that aid in reliable and repeatable measurements from an object, such as by detecting the contact pressure of the for example, handpiece 100 against the object. As the contact by the sleeve portion aids to stabilize the handpiece on the object, during measurement, the force exerted by the energy application tool on an object and any measured characteristics may be affected by the force the operator exerts on the handpiece to hold it in place against the object. The proper amount of contact force on the object may be important and may need to be monitored, since, for example, either insufficient or excessive force exerted by an operator may complicate the measurements, and may even produce less accurate results. A sensor may be disposed inside the handpiece to measure such contact force, which may generally be not physically or mechanically coupled to the energy application tool 110, such that it may be aid in monitoring proper contact force applied by the operator for better reproducibility, even by different operators. In general, it may be desirable to isolate the energy application tool 110 from other parts of the system, such as the portions of the handpiece 100 which contact the object (besides the energy application tool 110 itself), such that they do not interfere with the application of energy or measurements taken or the interference is minimized.

In exemplary embodiments, a sensor may be disposed in a manner to measure the force exerted by the operator on the object via contact with the handpiece 100. For example, the sensor may thus be positioned, for example, between the object and the handpiece. The sensor may also be placed to receive transduced or transmitted force from the portion of the handpiece in contact with the object. The sensor may further be positioned between the handpiece and the operator in a manner that allows it capture the force applied. In some embodiments, an internal force sensor may be utilized which may rely on transduction or transmission of the normal force from contact with the object through portions of the handpiece 100.

FIGS. 1, 1*d*, 1*e*, 11 and 11*a* illustrate an arrangement where the contact of a portion of the handpiece 100, such as the sleeve portion 120, may push (e.g. through contact at contact points 129 shown in FIGS. 2*b* and 4) on a force transfer member 130, such as a force transfer sleeve or sleeve-like component, which may then exert a force by pushing in direction B on a force sensor 143. A force sensor 143 may include any appropriate sensor for measuring the force being exerted from the contact of the handpiece 100 against an object by the user, such as, for example, a piezoelectric sensor, a force sensing resistor (e.g. a Shunt-mode FSR), a strain gauge or multiple strain gauges (e.g. mounted onto a cantilever(s) that flex in response to the applied force), linear position sensors (e.g. optical position sensors, magnetic field or other than can detect a position change of a component pressing against a spring or other element where the linear position change corresponds to the applied force), and/or any other appropriate type of force sensors. The force sensor 143 may further take on any appropriate shape or form, such as, for example, a flattened sensing pad, which may be in a ring shape that surrounds the energy application tool 110 as illustrated (such as to maintain separation of the energy application tool 110 from the contact forces being measured by the force sensor 143), or shapes such as ellipsoids, polygons or other shapes that may be positioned in the handpiece 100 to detect the contact force. In the exploded views of FIGS. 1*d*, 1*e* and 11, the force sensor 143, for example, is sandwiched between a relative fixed component. As illustrated in FIGS. 1*d* and 1*e*, the force sensor 143 may be sandwiched between the drive mechanism interface member 141, which itself is rigidly mounted to the drive mechanism 140 as discussed further below, and components that transfer force to the force sensor 143, as shown with the stacking of sleeve 120 (if present), transfer sleeve 112 and the sleeve mount 112*a*/force transfer member 130, which may pass through the apertures of the portions of the housing, as shown with forward end cap 105 and/or the sleeve mount PCB 108 and its retainer 107. The force sensor 143 may be, for example, held in a relative fixed position by mounting onto a rigid portion of the handpiece 100, such as the drive mechanism interface member 141, which may, for example, be coupled to drive mechanism 140 and/or to the housing 102 of the handpiece 100 such that it is in a relative fixed position with regard to the operator. The force sensor 143 may then detect the load originating from the contact with object 90 as biased against the relative fixed portion, such as the drive mechanism interface member 141. It may generally be understood that intervening components or portions between the object contact and the force sensor 143 may be present or not present so long as a full transduction/transmission path for the force remains for operation.

As illustrated in the exploded view of FIG. 11 and the block diagram of FIG. 11*a*, the force sensor 143 may alternatively be sandwiched between the drive mechanism 140 and a mounting bracket 148, which itself is rigidly mounted to the body of the handpiece 100, and components that transfer force to the force sensor 143, as shown with the stacking of sleeve 120 (if present), transfer sleeve 112, the sleeve mount 112*a*/force transfer member 130 (which itself is rigidly mounted to the drive mechanism 140) which may pass through the apertures of the portions of the housing, as shown with forward end cap 105 and/or the sleeve mount PCB 108 and its retainer 107. A force sensor 143 may include any appropriate sensor for measuring the force being exerted from the contact of the handpiece 100 against an object by the user, such as, for example, a piezoelectric sensor, a force sensing resistor (e.g. a Shunt-mode FSR), a strain gauge or multiple strain gauges (e.g. mounted onto a cantilever(s) that flex in response to the applied force), linear position sensors (e.g. optical position sensors, magnetic field or other than can detect a position change of a component pressing against a spring or other element where the linear position change corresponds to the applied force), and/or any other appropriate type of force sensors. The force sensor 143 may further take on any appropriate shape or form, such as, for example, a flattened sensing pad, which may be in a ring shape that surrounds the energy application tool 110 as illustrated (such as to maintain separation of the energy application tool 110 from the contact forces being measured by the force sensor 143), or shapes such as ellipsoids, polygons or other shapes that may be positioned in the handpiece 100 to detect the contact force. The force is then transferred through the drive mechanism 140 to the force sensor 143 as biased against the mounting bracket 148. This arrangement may be desirable, for example, to decrease flexing or misalignment of components, such as the drive mechanism 140 and the energy application tool 110 as they are rigidly connected to each other with a flexing fulcrum being generally present outside of these components (i.e. between the components 150 and the components 152 in FIG. 11*d*, as opposed to between the drive mechanism 140 and the force transfer member 130 as in FIG. 1*d*). Such potential flexing or misalignment may be undesirable, for example and without being bound to any particular theory, in uses of the handpiece 100 other than at a normal angle to the surface of an object, such as illustrated in FIGS. 8*a*, 8*b*, 8*g* and 8*h* against object 90. The increased rigidity in connections between the drive mechanism 140 and the energy application tool 110 may aid in reducing any variation in transfer of energy from the drive mechanism 140 and the energy application tool 110 when the handpiece is subjected to flexing or uneven loading when pressed against an object 90, such as when pressing the handpiece 100 against an object 90 at an angle, for example.

In some embodiments, as illustrated in FIGS. 1*c* and 1*e*, a force transducing or transmitting member may be utilized without the sleeve 120, as shown with force transfer member 130 and the transfer sleeve 112 in FIG. 1*e*, which may be used to contact the object.

Figure 4A:
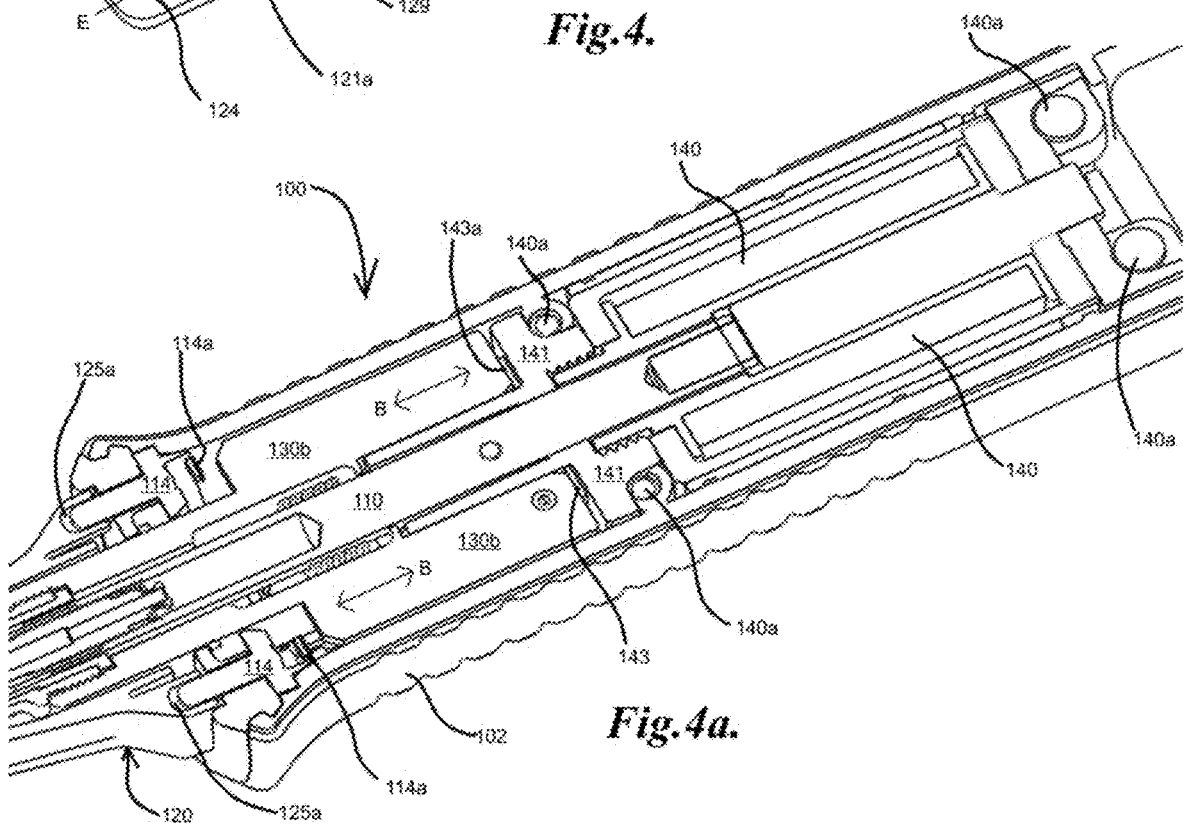
Figure 11B:
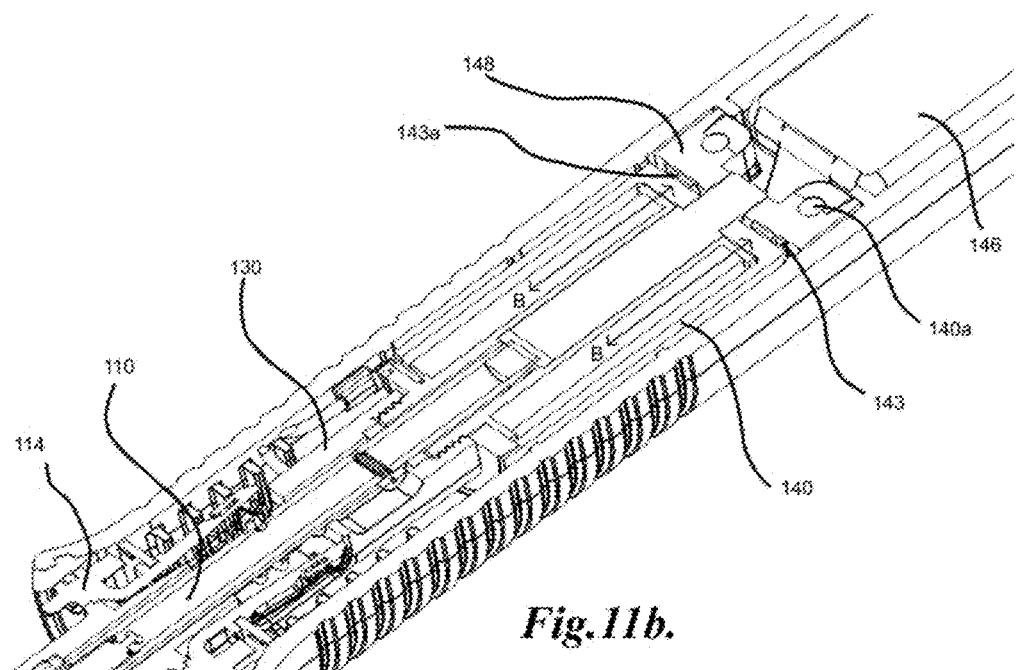
FIG. 11b illustrates a partial perspective cross-sectional view of a handpiece with rigidly connected force transfer components.

In embodiments of the system using a sleeve portion, a sleeve portion 120 may be mounted onto the force transfer member 130, such as onto sleeve mount 112*a* which may be coupled to or form a portion of force transfer member 130 and may extend out of the housing 102 via aperture 102*a*. The force from contact with the object may then be transferred, such as illustrated in FIGS. 4, 4*a*, 4*b* and 11*b* and 11*c*. As illustrated the normal force E from holding the sleeve portion 120 against the object may cause the sleeve 120 to push against the transfer sleeve 112, which may be a portion of or couple to the force transfer member 130, which may then exert the force in direction B on the force sensor 143, which may be biased against a rigid and/or relative fixed portion of the handpiece 100, such as the drive mechanism interface member 141, which may be mounted to the drive mechanism 140, which itself may be mounted to the housing 102, such as via drive mountings 140*a*, as illustrated in FIG. 4*a*, or as sandwiched between the drive mechanism 140 and the mounting bracket 148 which may be mounted to the housing 102, such as via drive mountings 140*a*, as illustrated in FIG. 11*b*.

In some embodiments, portions of the handpiece 100 may be movable relative to the rigid and/or relative fixed portion(s). This may be desirable to aid in transferring of force from the contact with the object to the force sensor and for providing a physically perceivable feedback to the operator of the exertion of contact force.

In some embodiments, multiple components may be utilized to form the force transfer member 130, such as for ease of manufacturing, assembly, replicability of parts, etc. For example, as illustrated, the force transfer member 130 may include separate parts transfer sleeve 112, sleeve mount 112*a* and force transfer base portion 130*b*, which may attach or at least contact to provide force transfer, such as at transfer member contacts 130*a*.

Figure 4B:
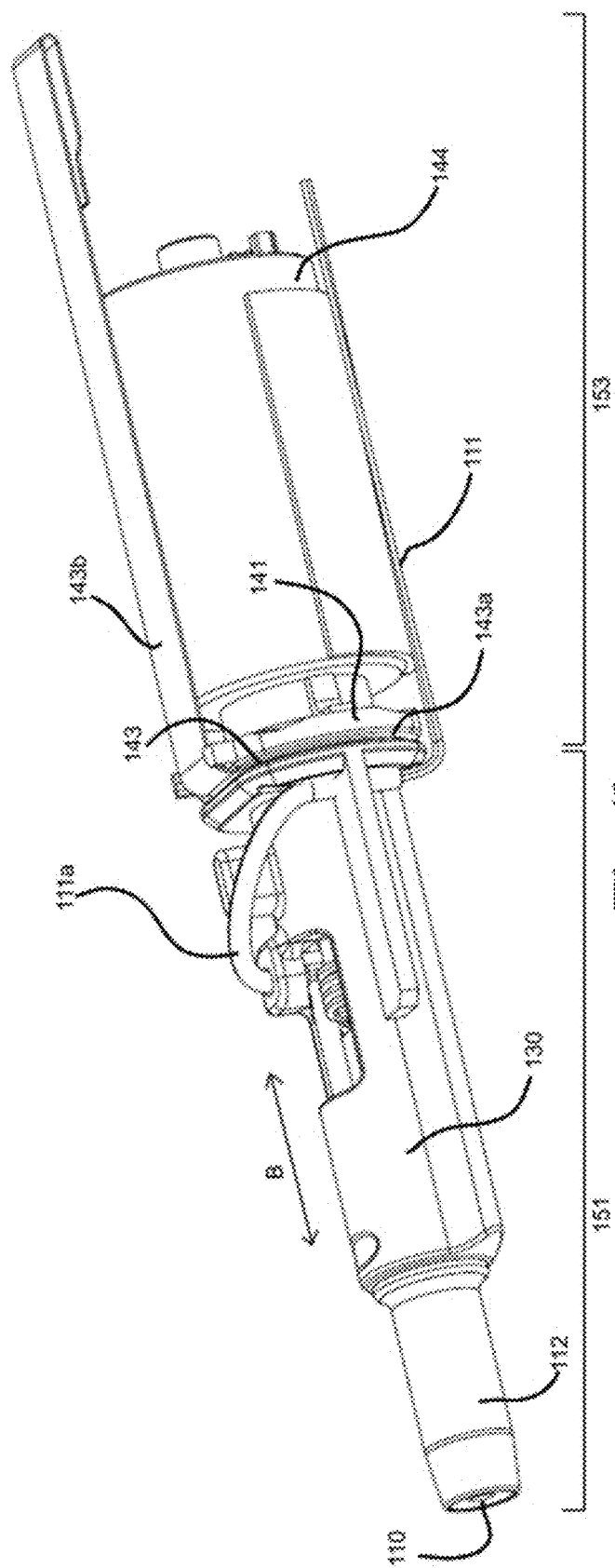

As illustrated in FIGS. 4 and 4*a*, the force transfer member 130 and its mechanically coupled portions, such as the sleeve portion 120, transfer sleeve 112, sleeve mount 112*a* and force transfer base portion 130*b*, may be movable, such as in direction B, relative to the relative fixed portions, such as the force sensor 143, drive mechanism interface member 141, drive mechanism 140 and housing 102. A biasing member, such as the force sensor bias 143*a*, may further be provided between the force transfer member 130 and the force sensor 143, such as to, for example, distribute the force on the force sensor 143 evenly and/or to serve as a return bias to return the force transfer member 130 to its original position along direction B when the contact with the object ceases, such as via a bias or leaf spring, or elastic cushion. In general, the movement of the components that transfer force to the force sensor 143 (e.g. the components 151 in front of the components 153 behind the force sensor 143 and the drive mechanism 140 as illustrated in FIG. 4*b* but not including the energy application tool 110 which is not directly coupled and does not translate in direction B with them in response to the contact force), such as the sliding distance caused by the contact force, may be very small, for example, in the order of about 0.3 mm to about 1 mm, more for example about 0.5 mm.

Figure 11C:
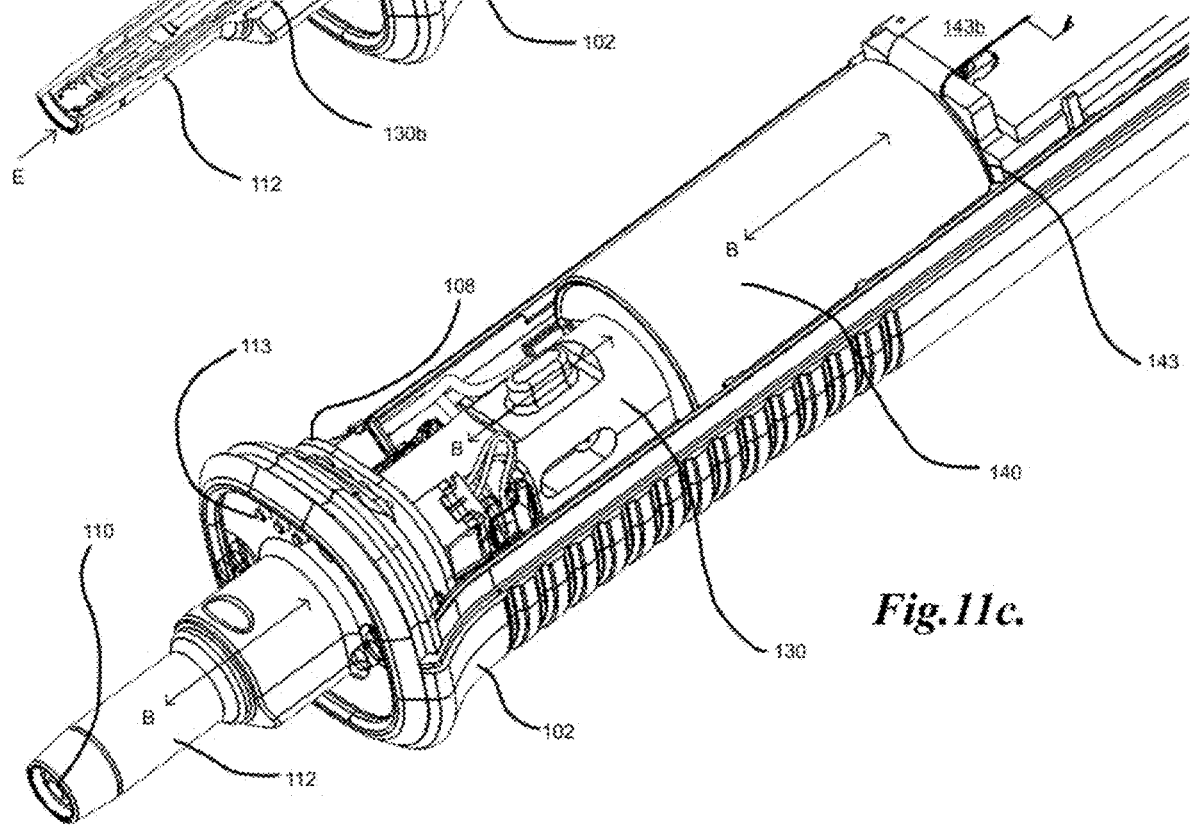
FIG. 11c illustrates a partial perspective view of the internals of the handpiece with rigidly connected force transfer components with a portion of the housing removed.

As illustrated in FIGS. 11*b* and 11*c*, the force transfer member 130 and its mechanically coupled portions, transfer sleeve 112, sleeve mount 112*a* and drive mechanism 140, may be movable, such as in direction B, relative to the relative fixed portions, such as the force sensor 143, mounting bracket 148 and housing 102. A biasing member, such as the force sensor bias 143*a*, may further be provided between the drive mechanism 140 and the force sensor 143, such as to, for example, distribute the force on the force sensor 143 evenly and/or to serve as a return bias to return the drive mechanism 140 to its original position along direction B when the contact with the object ceases, such as via a bias or leaf spring, or elastic cushion. In general, the movement of the components that transfer force to the force sensor 143 (e.g. the components 150 as illustrated in FIG. 11*d* but not including the energy application tool 110 which is not directly coupled and does not translate in direction B with them in response to the contact force), such as the sliding distance caused by the contact force, may be very small, for example, in the order of about 0.3 mm to about 1 mm, more for example about 0.5 mm.

In embodiments with an electrical contact between the sleeve portion 120 and the handpiece 100, such as the security feature 122 interacting with electronic contacts 113, movement between the sleeve 120 and the handpiece 100 may be compensated for, such as with spring pins and or placing electrical contacts such that contact is maintained through any motion of the sleeve 120 while mounted on the handpiece 100, such as by placement on parallel surfaces or on the movable portions, such as the sleeve mount 112*a*.

The sleeve portion 120 may also be mounted onto a force transfer member 130 that forms a permanent part on the front of the housing 102, and shields the energy application tool 110, for example, a tapping rod, from damage when no sleeve portion is present, for example, the sleeve portion forms part of a disposable assembly, as discussed above and/or below.

In some embodiments, as discussed above, the sleeve 120 and/or the energy application tool 110 may be disposed substantially perpendicular to the housing 102, as illustrated in FIG. 1*f*. The holding force against the object may then act in direction B, as illustrated, and as such the sleeve 120 may press in direction B against a force transfer member 130 onto a force sensor 143, which may be mounted and/or positioned against a relative fixed point, such as against the housing 102 as illustrated.

The energy application tool 110, for example, a tapping rod, may be enabled or triggered when the object contacting portion of the sleeve portion, such as the contact portion 121 of the sleeve 120, is pushed against an object undergoing measurement, for example, a tooth and a force within a certain range may be detected. When the correct force is detected, the handpiece 100 is turned on or enabled to start the measurement.

For example, with dental procedures on human teeth, an appropriate contact force may be about 3 N to about 10 N for example, more for example about 5 N to about 8 N of force. In general, the force sensor 143 may read the actual contact force or may read a transferred, transduced or transmitted force which differs from the actual contact force, which may be interpreted or correlated to the actual contact force by the handpiece 100, such as with electronics assembly 144. The measurement of the contact force may further be corrected, such as due to orientation of the handpiece 100 in the gravitational field, with input from an accelerometer or other appropriate device to detect orientation, as illustrated in FIGS. 1 and 11*a* with orientation sensor 145.

The sensor, for example the force sensor 143, may be in physical proximity and/or contact and/or coupled with at least a portion of the handpiece 100 other than the energy application tool 110, for example, it may be in physical proximity and/or contact and/or coupled with the sleeve portion 120, if the open end of the sleeve portion 120 may include an object contacting portion 123, as noted above. In one embodiment of the invention, the sensor may include at least one strain gauge for sensing. The strain gauges may be attached or mounted to a cantilever between the device housing and the sleeve portion so that when the object contacting portion of the sleeve portion is pressed on the object it also deforms the cantilever which is measured by the strain gauge, thus providing a force measurement. In some embodiments, multiple strain gauges mounted to a single or to separate cantilevers may be utilized. The cantilever(s) may also, for example, be present on a separate component from the rest of the housing or sleeve portion, such as, for example, on a mounting device. According to one aspect, the force sensing may be done by a linear position sensor, which would know, for example, that if the force transfer sleeve like portion is at position X, a force of Y has to be applied to it (against the reaction force of the spring) to move it to that position. According to another aspect, the force sensing may be performed by an optical sensor, for optically sensing the position of the moving part, when it is pushed against a spring, In yet another embodiment of the invention, the relative position of the object contacting portion of the sleeve portion on the object may be determined by having one or more strain gauges which may be attached at one end to a moving part, for example, a force sensor sleeve like component, and the other end to a static element, for example, the housing. In a further embodiment of the invention, the device may include piezoelectric elements for directly measuring the force. In yet a further embodiment of the invention, a hall effect sensor may be used to detect a change in the magnetic field when a magnet (attached to the moving element) is moving relative to the position of the sensor. In yet another embodiment of the invention, a capacitive linear encoder system, like that found in digital calipers may be used to measure the force.

The sensing pad may include a layer structure, which may be generally referred to as a "Shunt Mode" FSR (force sensing resistor) that may change resistance depending on the force applied to the pad, to provide a force measurement. FSRs typically consist of a conductive polymer, which changes resistance in a predictable manner following application of force to its surface. The sensing film of the FSR typically includes both electrically conducting and non-conducting particles suspended in a matrix. Applying a force to the surface of the FSR causes particles to touch the conducting electrodes, changing the resistance of the FSR. FSRs may be desirable for their low size, such as with a thickness typically less than 0.5 mm, low cost and good shock resistance.

Figure 6:
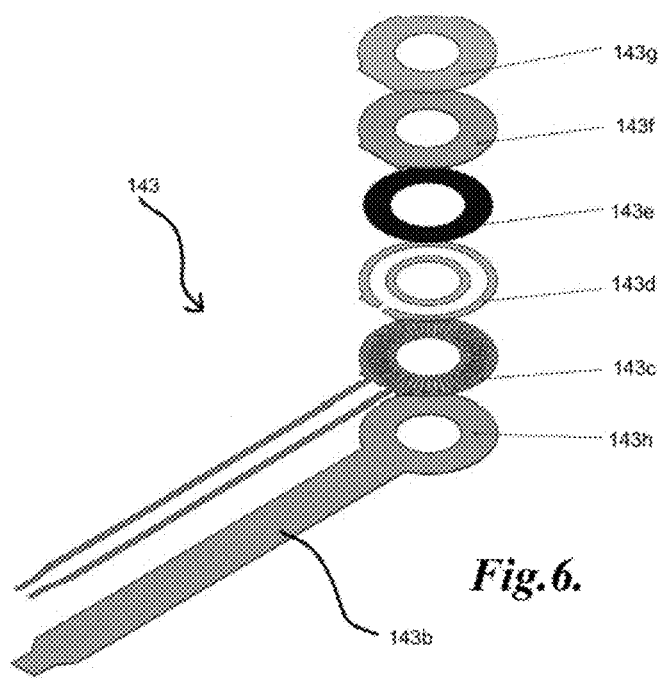
FIG. 6 illustrates a layered force sensor.

FIG. 6 illustrates an example of a layered force sensor 143 which may include a base layer 143h on which is printed or otherwise deposited a conductive trace 143c with two conductive pathways which are joined by an FSR layer 143e on an FSR substrate 143f to produce a conductive pathway modulated by the resistance of the FSR layer 143e. Pressure applied to the FSR layer 143e, such as in the direction B from the force transfer member 130, may alter its resistance, such as by decreasing it with applied pressure. Adhesive layers, such as adhesive layer 143d and mounting adhesive 143g, may also be included to join layers together and/or to provide adhesion to a substrate, such as to the drive mechanism interface member 141. The force sensor 143 may generally include a connector, such as flexible connector 143b shown in FIGS. 1d and 1e, to connect to an interface on electronics assembly 144, such as by carrying connections to the conductive pathways in the conductive trace 143c.

Piezoelectric sensors may also be utilized that convert pressure exerted on the force sensor 143 into a change in electrical characteristics, such as a voltage across the piezoelectric element.

A strain gauge or other similar element may also be included on a leaf spring or other biasing member, such as the force sensor bias 143a.

In some exemplary embodiments, the force sensor may be in electronic communication with the energy application tool 110 and may act as an on/off switch or activation switch for the handpiece 100. For example, when a proper force is exerted on the object by the object contacting portion of the sleeve, it may trigger the activation mechanism of the instrument to activate the movement of the energy application tool 110 to start a measurement. Thus, no external switches or push buttons are needed to activate the on and off of the system, as noted above. The indication of the proper force may be indicated by visible or audible signals.

Figure 7:
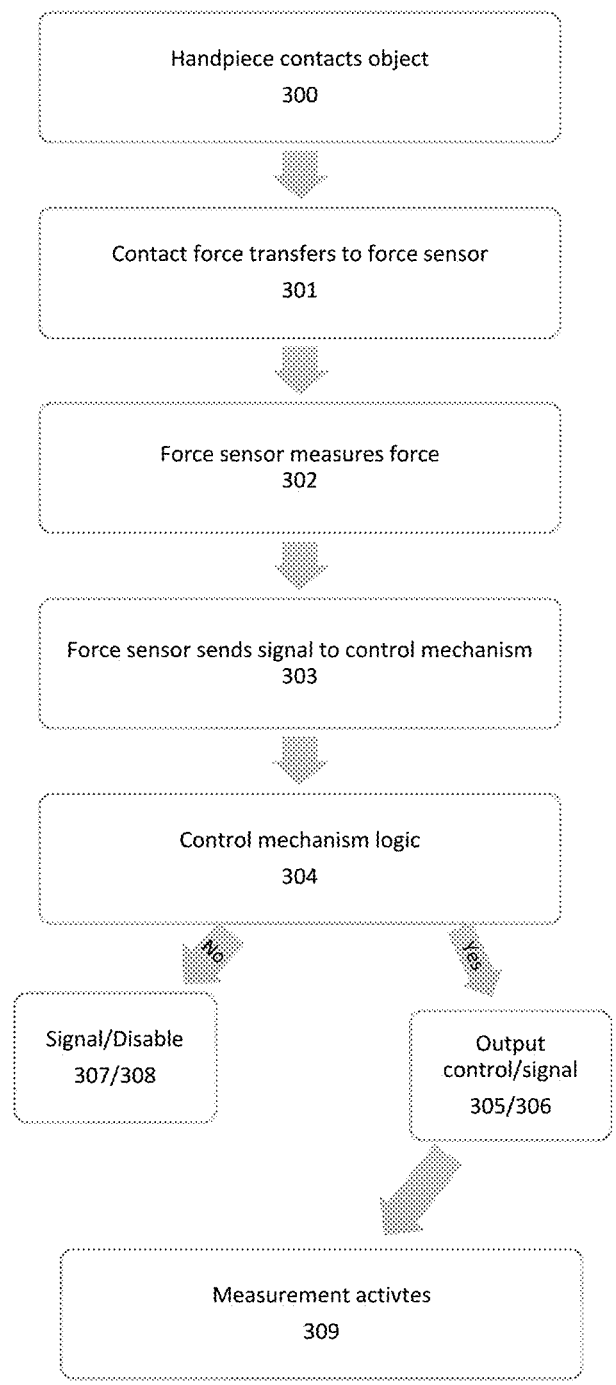
FIG. 7 shows a flowchart of operating a handpiece to place and take a measurement from an object.

In some embodiments, as illustrated with the flow chart in FIG. 7, the contact of the handpiece 100 with the object 90 (300), such as with the sleeve portion 120 may transfer contact force, such as the normal force E from the contact, to the force sensor 143 (301). The force sensor 143 may measure the contact force or a transferred force and produce a signal or change in characteristic, such as resistance, voltage, etc. (302). The signal or change in characteristic may then be relayed to the control mechanism, such as in the electronics assembly 144 (303). The control mechanism may then determine if the contact force is in an acceptable range, for example 5-8 N (304). If the force is in the range, the control mechanism may enable the energy application tool 110 to operate (305) and/or output a signal to the user that the contact force is acceptable (306). If the contact force is out of the acceptable range, the control mechanism may output a signal to the user to change the pressure (307) and/or disable or keep disabled the energy application tool 110 (308). If acceptable, the control mechanism may also initiate the energy application tool 110 automatically and perform a measurement (309). Afterwards, the control mechanism may be reset for a new measurement.

In some embodiments, the energy application tool 110 may be instantaneously turned on once a proper contact force is exerted by the contact portion 121 (or other portion of the sleeve 120 or handpiece 100, as appropriate) on the object, as indicated by visible or audible signals. FIG. 1c illustrates operator signals, as shown with light sources 114, which may provide signals to the operator about the contact force. In some embodiments, there may be a delay prior to activating the energy application tool 110 once a proper contact force is exerted on the object, as indicated by visible or audible signals, as above. In a further embodiment, once a certain push force on the object is detected and maintained for a period of time, for example, about 0.5 seconds, the instrument may be turned on to start measurement.

In some embodiments, the force measurement may be connected to a visual output, such as lights. Lights may be mounted at any convenient location on the instrument, for example, one or multiple LEDs may be mounted at the front of the instrument, as shown with light sources 114. For example, a multiple light system may be included. For example, two LEDs may be used, such as green for acceptable and red for unacceptable contact force.

In some embodiments, a light from the light sources 114 lights up the sleeve 120, which may be transparent or translucent, to indicate acceptable or unacceptable contact force.

The proper force exerted by the operator on the object acts as a switch of the system. When the system is not switched on, it may be desirable to know whether it has malfunction, not sufficient force or too much force is exerted. In some embodiments, if the user is pushing too hard on the object, the light may change first to amber, then to red, such as indicated via output from the light sources 114. If the push force is sufficient to change the light to red, percussion may either not be started, or be interrupted if it has already started. In addition, there may be an amber LED state which warns when the user is approaching too much push force. At that stage, the instrument may still operate when the LEDs are lit amber. In another example, no light may indicate too little force, a green light may indicate the right amount of force, while a red light may indicate too much force. In yet another example, a one light system may be included. For example, no light may give a signal of too little force and a red light may give a signal of too much force. In a further example, a flashing red light may indicate too much force and no light may indicate too little force. The LEDs may be mounted on the surface of the handpiece 100, or they may be internal to the housing 102 and light may be conveyed via light pipes or fiber optic channels, which may present at the surface of the housing 102, such as at the light sources 114 shown as light pipes in FIGS. 1d and 11. In some examples, the light pipes 114 may be integral or attached to a portion of the handpiece 100, such as being integral or attached to the retainer 107' in FIG. 1g, which may be substitute retainer 107 in FIG. 1d.

In some embodiments, the light pipes 114 may extend into the sleeve portion 120 such as to better carry light toward the object and/or to better illuminate the sleeve portion 120 for a user's perception. FIGS. 4, 4a and 11b illustrate light pipes 114 extending from the handpiece 100 to carry light from the light sources 114a into the sleeve portion 120, as shown by extending into slots 125a in the sleeve portion 120. Light emanating from the light pipes 114 may then illuminate the sleeve portion 120, which may, for example, be adapted to diffuse the light toward the object and/or in a manner to be easily observable by the user, such as by inclusion of light diffusing material(s), additive(s) and/or by physical treatment, such as frosting and/or any other appropriate treatment. The light pipes 114 may also be utilized to provide additional alignment, connection and/or securement between the sleeve portion 120 and the handpiece 100, such as by fitting into the slots 125a of the sleeve portion 120. For example, the utilization of one or more light pipes 114 fitting into slots 125a may aid in providing resistance to rotation about the longitudinal axis by the fitting between the light pipes 114 and the slots 125a (e.g. by close or friction fitting).

In another embodiment, the force measurement may be connected to an audible output. In one example, the audible output may include a beeping sound to indicate too little force and a multiple beep to indicate too much force. In another example, the audible output may include a beeping sound to indicate too little force and a beeping sound with a flashing red light to indicate too much force, such as via the light sources 114 or as discussed above with internal light sources. In a further example, the force measurement may be connected to a voice alert system for alerting too much force or too little force. In yet a further example, the force measurement may be connected to a voice alert system to alert too little force and a voice alert and a flashing red light for alerting too much force.

The handpiece 100 may also include a reset button, such as shown with reset control 144b in FIGS. 1d and 11, such as to reset the handpiece 100 to re-attempt placement with a proper force after an initial incorrect placement. The reset button 144b may press onto an appropriate control on the electronics assembly 144 to place the handpiece 100 in a renewed state.

When the force sensor acts as an on/off switch, it may also act to monitor that a proper force is exerted on the object during measurement and/or a proper alignment of the handpiece 100 against the object during measurement is obtained. An inclinometer as shown with orientation sensor 145 in FIGS. 1 and 11a, may be present, for example, as part of an electronic control system, which may trigger an audible warning when the device is outside of the angular range of operation, for example, for a tapping rod, it may trigger the warning when it is plus/minus 30 degrees from horizontal. If the device is oriented such that the axis of operation is greater than 30 degrees from horizontal when a push force is sensed on the object contacting portion of the sleeve portion, it may result in a warning sound being emitted by a speaker located on the device, such as the PCB within the device. In such circumstances, the percussion action will not begin until the device is returned to an acceptable angle. In some instances, if the percussion action has started when the above mentioned departure from the range is detected, the device may not actually stop operation, but may simply be sounding an alarm, so that corrections may be made.

Common implementations of tilt sensors and inclinometers may include, but are not limited to, accelerometer, liquid capacitive, electrolytic, gas bubble in liquid, and pendulum-type systems. Traditional spirit levels and pendulum-based electronic leveling instruments are usually constrained by only single-axis and narrow tilt measurement range. However, most precision leveling, angle measurement, alignment and surface flatness profiling tasks essentially involve a two-dimensional surface plane angle rather than two independent orthogonal single-axis objects. Two-axis and three-axis inclinometers are typically built with micro electro-mechanical systems (MEMs) tilt sensors provides simultaneous two-dimensional angle readings of a surface plane tangent to earth datum.

MEMS tilt sensors typically employ accelerometers for functionality. Conceptually, an accelerometer behaves as a damped mass on a spring, where the accelerometer experiences an acceleration and the mass is displaced to the point that the spring is able to accelerate the mass at the same rate as the casing. The displacement is then measured to give the acceleration. In commercial devices, piezoelectric, piezoresistive and/or capacitive components are commonly used to convert the mechanical motion into an electrical signal. Piezoelectric accelerometers rely on piezoceramics (e.g. lead zirconate titanate) or single crystals (e.g. quartz, tourmaline). They typically offer favorable characteristics in application, such as upper frequency range, low packaged weight and high temperature range. Piezoresistive accelerometers are typically preferred in high shock applications. Capacitive accelerometers typically use a silicon micromachined sensing element, where their performance is superior in the low frequency range and they can be operated in servo mode to achieve high stability and linearity. Modern accelerometers are often small MEMs comprising a cantilever beam with a proof mass. Damping results from the residual gas sealed in the device. Under the influence of external accelerations the proof mass deflects from its neutral position. This deflection is measured in an analog or digital manner.

In an example of the use of an orientation sensor 145 in the form of a three-axis accelerometer mounted to the electronics assembly 144, the handpiece 100 was held against an object at angles between 30 degrees of incline and decline and the values returned from the accelerometer were utilized to create variations in the activation of the drive mechanism 140.

The following table shows the values returned from the accelerometer in the three axes at the following inclines/declines:

TABLE 1

| Angle | X | Y | Z |
|---|---|---|---|
| 30 degrees decline | −11 | 36 | −46 |
| 25 degrees decline | −10 | 31 | −49 |
| 20 degrees decline | −9 | 27 | −51 |
| 15 degrees decline | −8 | 21 | −53 |
| 10 degrees decline | −7 | 15 | −54 |
| 5 degrees decline | −7 | 9 | −55 |
| Horizontal | −7 | 0 | −55 |

TABLE 1-continued

| Angle | X | Y | Z |
|---|---|---|---|
| 5 degrees incline | −4 | −4 | −55 |
| 10 degrees incline | −3 | −10 | −54 |
| 15 degrees incline | −2 | −15 | −53 |
| 20 degrees incline | −1 | −21 | −52 |
| 25 degrees incline | 1 | −26 | −50 |
| 30 degrees incline | 2 | −32 | −47 |

The values were utilized to create a preprogrammed set of instructions to vary the activation of the drive mechanism 140 when utilizing the energy application tool 110 at different inclinations to aid in evening out the force applied to approximately 25 N. In an example, the drive mechanism 140 was engaged for 22 milliseconds with a delay of 11 milliseconds before retracting (fixed timing) and yielded the measured applied force from the energy application tool 110 at different inclinations in the following table. Utilizing the preprogrammed set of instructions for different inclinations, the engaging time and delay time of the drive mechanism 140 was varied and yielded the following measured applied force from the energy application tool 110.

TABLE 2

| | Fixed Timing 22/11 ms | | Variable Timing | |
|---|---|---|---|---|
| | Average Force (N) | Target Force (N) | Average Force (N) | Drive/Delay (ms) |
| 30 degrees decline | 36.9 | 25 | 23.2 | 16/10 |
| 25 degrees decline | 35.6 | 25 | 25.5 | 17/11 |
| 20 degrees decline | 35.1 | 25 | 23.5 | 17/11 |
| 15 degrees decline | 33.7 | 25 | 25.6 | 18/11 |
| 10 degrees decline | 32.2 | 25 | 26.7 | 19/11 |
| 5 degrees decline | 30.0 | 25 | 24.4 | 19/11 |
| Horizontal | 27.5 | 25 | 26.3 | 21/11 |
| 5 degrees incline | 25.2 | 25 | 23.9 | 21/11 |
| 10 degrees incline | 23.1 | 25 | 24.2 | 22/11 |
| 15 degrees incline | 21.4 | 25 | 24.5 | 23/11 |
| 20 degrees incline | 18.7 | 25 | 24.7 | 24/12 |
| 25 degrees incline | 16.1 | 25 | 25.5 | 25/12 |
| 30 degrees incline | 12.3 | 25 | 26.1 | 27/13 |

The measured forces show that the preprogrammed set of instructions yielded much closer force values to the target force of 25 N than with the fixed timing in the first column. The varying of the activation of the drive mechanism 140 based on the inclination determined by the orientation sensor 145 may thus be utilized to produce a more consistent applied force from the energy application tool 110 based on the measured angle of inclination.

The device and/or a portion of the housing may also have an antimicrobial coating coated thereon capable of eliminating, preventing, retarding or minimizing the growth of microbes, thus minimizing the use of high temperature autoclaving process or harsh chemicals and may increase the kind and number of materials useful as substrates for making such tools or instruments.

Further, the instrument may be useful in aiding in the selection of material, such as mechanically biocompatible material, or biomemetically compatible material used in the construction of and/or selection of a material for an anatomical structure, for example, an implant. For normal healthy teeth, the percussive energy generated by mastication is attenuated by the periodontal ligament at the healthy bone-natural tooth interface. However when an implant replaces natural tooth due to damage or disease, the ligament is generally lost and the implant may transmit the percussive forces directly into the bone. Several materials such as composites, gold, zirconia and so on, used to fabricate the implant abutment have been shown to be effective in numerous studies. While studies have demonstrated the survivability of implant restorations utilizing composite resin, gold or zirconia abutments after construction of the abutments, there has been no such research done to measure the dynamic response to load of said abutment materials. The instrument of the present invention may be used for such purposes and may be useful to predict the suitability or compatibility prior to implantation, or to choose suitable materials to protect natural teeth adjacent the implants. Thus, the choice of materials may minimize the disparity between the way the implants and natural teeth respond to impact.

Furthermore, the instrument may be useful in aiding in the selection of material, such as mechanically or chemically durable or compatible material, used in the construction of and/or selection of a material for, for example, a plane, an automobile, a ship, a bridge, a building, any industrial structures including, but limited to power generation facilities, arch structures, or other similar physical structures or damping material suitable to aid in the construction of such structures. The instrument of the present invention may be used to such purposes and may be useful to predict the suitability of a material prior to construction in addition to detection of cracks, fractures, microcracks, cement failures, bond failures or defect location, etc., after the construction.

In addition, the present invention is also useful in distinguishing between defects inherent in the material making up the structure or object, and cracks or fractures, etc., as discussed above due to trauma or wear or repeated loading. Defects inherent in the bone or material construction of an implant, or a physical structure, for example, may include lesions in the bone, similar defects in the implant construction or manufacturing of polymer, polymer composites or alloys, or metallic composites or alloys.

The stabilization of the instrument by the sleeve portion or contact feature, and/or tab or the tab and/or component may also minimize any jerky action that may confound the testing results, for example, any defects inherent in the bone structure or physical or industrial structure may be masked by jerky action of the tester. This type of defect detection is important because the location and extent of the defect may impact dramatically upon the stability of the implant or physical or industrial structures. Generally when lesions are detected, for example, in an implant, such as a crestal or apical defect, the stability of the implant may be affected if both crestal and apical defect are present. In the past, there is no other way of gathering this type of information other than costly radiation intensive processes. With the present invention, this type of information may be gathered, and may be done in an unobtrusive manner.

The present invention further relates to a system and method for measuring structural characteristics that minimizes impact, even minute impact on the object undergoing measurement, without compromising the sensitivity of the measurement or operation of the system. In one embodiment, for lower impact force without compromising the sensitivity of the measurement the system includes an energy application tool 110 that is light weight and/or capable of moving at a slower velocity such that it minimizes the force of impact on the object during measurement while exhibits or maintains better sensitivity of measurement. In one aspect, the energy application tool 110, for example, the tapping rod, may be made of lighter material to minimize the weight of the handpiece, if the device is a handpiece. In another embodiment, the energy application tool 110, for example, the tapping rod, may be made shorter and/or of smaller diameter such that the size of the handpiece may also be minimized. For example, tool 110 may be made of materials that may include titanium or the tool may have a hollow shell and filled with for example, lead. In a further embodiment, the system may include a drive mechanism that may lessen the acceleration of the energy application tool 110. For example, the drive mechanism may include a smaller drive coil to lessen the acceleration of the energy application tool 110, whether or not it is light weight, and/or smaller in length or diameter, and the impact force on the object during operation while maintaining sensitivity of measurement. These embodiments may be combined with one or more of the embodiments described before, including the lighter weight handpiece housing. The speed of conducting measurement may also be desirable without increasing the initial velocity of impact so as to minimize impact on the object during measurement. The present invention relates to yet another system and method for measuring structural characteristics having a drive mechanism that may decrease the travel distance of the energy application tool, for example, from about 4 mm to about 2 mm, while maintaining the same initial velocity at contact and thus, faster measurement is possible without compromising the operation of the system. The system may or may not have disposable parts and/or features for aiding in repositionability and/or lessening impact with features mentioned below.

In general, the present invention further represents a new form of precision of risk assessment in dental health or structural integrity of physical structures and an opportunity to diagnose in a new manner. The present invention provides for the administering of kinetic energy to the specimen, loading and displacement rates that may be determined by the specimen, deceleration measured upon impact and analysis of dynamic mechanical response for more accurate prediction of cracks, fractures, microcracks, microfractures; loss of cement seal; cement failure; bond failure; microleakage; lesions; decay; structural integrity in general; structural stability in general or defect location.

Further, multiple indicators of structural integrity, such as LC (loss coefficient) and ERG (energy return graph) may be possible as well as percussion loads in a critical direction. The present system provides a convenient and easy way of providing buccal loading and other loading directions are possible such as the lingual direction for testing the structural properties mentioned above.

Buccal loading is important in that it is typically the more dangerous type of loading encountered by, for example, a tooth. In general, vertical loading induces relatively low stresses in teeth. However, working and/or nonworking motion produces side loading as a result of the lateral motion of the jaw and inclined geometries of the occlusal surfaces of teeth and restorations. This side loading may induce much higher stress concentrations at external and internal surfaces and below the margin. Thus, using the system of the present invention, such tests may be easily performed. In short, the system not only is adapted for detection of structural stability, integrity, cracks, etc., of a prosthetic dental implant structure, a dental structure, an orthopedic structure, or an orthopedic implant, but may also be adapted for use in the actual construction and replacement process through testing under stresses that may be encountered later after implantation, or restoration.

Natural loading is typically pulsatile (as opposed to for example sinusoidal). Muscular, cardiovascular, running, jumping, clenching/bruxing, so on, all may produce loading, for example, pulsatile loading. Percussion loading is pulsatile and therefore physiological. Percussion loading may be used to measure visco-elastic properties and detect damage in a structure.

As noted above, the present invention has applications also in the detection of internal damage such as microcracking, fracture, microfracture and delamination in composite structures and other engineering materials which may be used in both anatomical and non-anatomical structures. Composites are generally more susceptible to damage development than unreinforced metals, particularly when they are under stresses that approach the tensile strength of the material. The present invention is useful for detecting damage through nondestructive testing in composite materials and their resulting structures.

The system may be applicable for testing on various objects, both anatomical and mechanical, as noted before. For an anatomical object, such as a tooth, natural or restored, prosthetic dental implant structure, a dental structure, or an orthopedic implant, measurement or testing is generally performed while the object is stationary. For a mechanical object, which may include, but not limited to polymeric composite structures including honeycombs or layered honeycombs or metallic composite structure; an airplane structure, an automobile, a ship, a bridge, a tunnel, a train, a building, industrial structures including, but not limited to power generation facilities, arch structures, or other similar physical structures, testing may also be carried out on a mobile object while moving.

Figure 9:
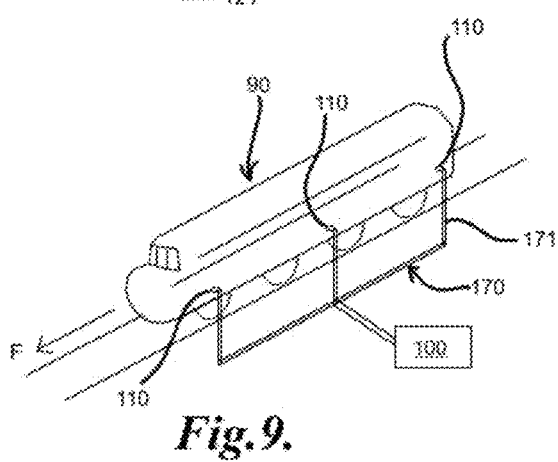
FIG. 9 illustrates use of an array of energy application tools to measure a moving object.

FIG. 9 illustrates the use of an array 170 of energy application tools 110 positioned along the path of a moving object, shown as a train 90 moving in direction F. In general, the energy application tools 110 may be positioned at known intervals along the path of the moving object and may be positioned, such as by struts 171 as illustrated, to enable energy delivery to the moving object, such as the train 90, at desired locations for measurements. In general, the multiple energy application tools 110 may be triggered in a temporally controlled manner, such as in sequence accounting for the speed of the moving object such that each triggers to deliver energy to the substantially same location to enable multiple measurements of the same location as the moving object moves past, or timed to deliver energy to the moving object at different locations, or some combination thereof. Thus, mechanical objects may also be undergoing testing when they are either stationary or moving, which may give particular insight into the object under actual working conditions. This may be performed using one energy application tool 110, over a plurality of spots on the object 90, to obtain an average condition of the object in general or be performed on the same spot using many separate energy application tools 110 or devices 100 to obtain an average result on the same spot. In this example, measurements may be performed under actual operating conditions.

Mechanical energy associated with an impact against, for example, a natural tooth, for example, is primarily dissipated by the periodontal ligament. More specifically, when a tooth is subjected to an impact force, a stress wave is transmitted through the tooth and into the periodontal ligament, which functions to connect the tooth to the underlying bone. Because of the way it deforms, the periodontal ligament acts as a shock absorber, dissipating much of the energy associated with the impact. This damping process advantageously reduces the resultant impact force transmitted to the surrounding bone. In contrast, dental implant prostheses, for example, often have no mechanism by which to dissipate significant amounts of mechanical energy because of the nature of the materials used. Thus, mechanical energy tends to pass from an implant structure to the underlying bone with relatively little damping. This difference in mechanical behavior may be particularly critical for people who habitually brux and/or clench their teeth, since such behavior imparts relatively large impact forces on teeth. For a physical structure, whether or not a damping material is incorporated into the structure, the mechanical energy associated with an impact against the structure may generate a different response when there is a crack, microcrack, fracture, microfracture, delamination, defect or any structural instability than for a structure without a crack, microcrack, fracture, defect or any structural instability.

The relative extent to which a material dissipates elastic mechanical energy can be characterized using the loss coefficient, as discussed previously. Loss coefficient values may be determined for any of the objects mentioned above, including natural teeth, as well as for a wide variety of implant-supported superstructures, such as superstructures made of resin matrix composites, gold alloys, porcelain fused to gold laminates, lithium disilicate, zirconia, all ceramic restorations or any other material suitable for use in the oral cavity. Implant-supported structures typically dissipate less mechanical energy than their natural tooth counterparts. However, the ability of an implant to dissipate mechanical energy depends on the level of osseointegration around the implant: poor osseointegration between an implant and the surrounding bone can cause abnormally high levels of energy dissipation. Thus, energy dissipation initially increases after placing an implant, for example, due to bone remodeling but then usually decreases as osseointegration progresses. Eventually, the energy dissipation (damping) capacity of the implant becomes constant as the osseointegration process progresses to completion. As noted above, for normal healthy teeth, the percussive energy generated by mastication is attenuated by the periodontal ligament at the healthy bone-natural tooth interface. When a natural tooth is damaged or diseased, an implant replaces it, but without the ligament as it is lost. In most cases, in a successfully integrated implant, there is no ligament. Under this, the implant may transmit the percussive forces directly into the bone. To compensate for this loss, the use of, for example, some composites, zirconia and so on, to fabricate the implant abutment has been shown to be effective in numerous studies. The instrument of the present invention may serve in aiding in the construction or fabrication of and/or selection of a material for an anatomical structure, for example, an implant. The measurement of the dynamic response to load of said abutment materials may be used to such purposes and may be useful to predict the suitability of the restorative material for the implant prior to implantation or prior to restoration.

For example, a computer handling input from the handpiece 100 may further include memory registers, such that time versus percussion response, for example, the amount of energy reflected from the object 90 at several points over a discrete time period can be recorded. In such embodiments, the energy returned from the object 90 can be plotted as a function of time on a display attached to the computer. This configuration allows the user to view and analyze the time-energy profile of the energy reflected from the object 90.

In addition to generation of a time-energy profile, other analyses can also be performed on the signals returned from the sensing mechanism 111, such as a piezoelectric force sensor. For example, the amount of work associated with the impact can be evaluated by integrating the force applied to the energy application tool 110, such as a tapping rod, with respect to the displacement of the object 90. The force applied to the energy application tool 110, such as a tapping rod during its impact with the object 90, can be measured using the sensing mechanism 111, such as a piezoelectric force sensor. After the impact, the amount of work depends partially on the quantity of defects present in the object 90. In particular, defects in the object 90 may dissipate the kinetic energy of the tapping rod of the energy application tool 110 as it impacts the object 90, thereby reducing the amount of elastic energy available to be returned to the tapping rod.

In one embodiment, a comparison of the amount of elastic energy returned to the tapping rod and the total work associated with the impact can be used to determine the quantity and nature of structural defects present in the object 90. In another embodiment, a Gaussian distribution peak or other mathematically derived peak, may be fitted to the measured percussion response such as energy, stress or force data. The residue or mean error may be used to determine how closely the measured data are representative of a defect-free object 90.

Figure 10:
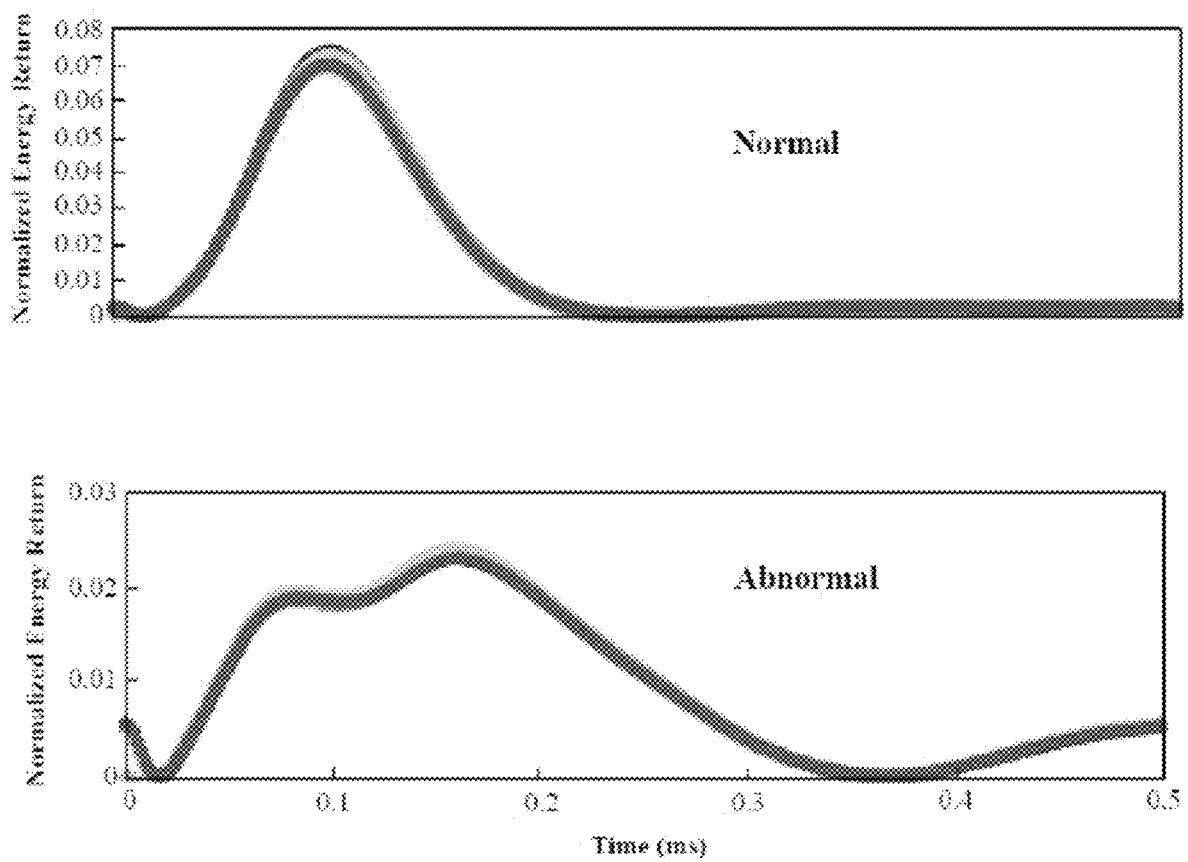
FIG. 10 shows the energy response from a normal and a damaged object.

FIG. 10 shows examples of the shape of time versus percussion response, for example, time-energy profiles generated on tooth. For a normal tooth, a smooth, bell-shaped curve is generated, as shown. For an abnormal tooth, a curve having various shapes, for example, asymmetric profile or multiple peak profile is generated, as shown. Even though the profiles shown are in reference to tooth, the profiles may be generalized to any other objects mentioned above, whether anatomical or industrial or physical.

Since buccal loading is the more dangerous type of stress encountered, the ability to correlate test results with actual response when implanted is another aspect of the present invention. In general, occlusal clenching induces relatively low stresses, working and/or nonworking motion may produce side loading and may induce much higher stresses which may generate highest stress concentration at internal surface and below the cementum-enamel margin. Thus, using the system of the present invention may aid in selecting the best material or construction design in or for an implant or a natural tooth. This may also be applied to non-anatomical systems. Additionally, this testing of the structure may continue throughout the lifetime of the structure without any disassembly or destructive processes to monitor the structural integrity of the site over time.

Figure 10A:
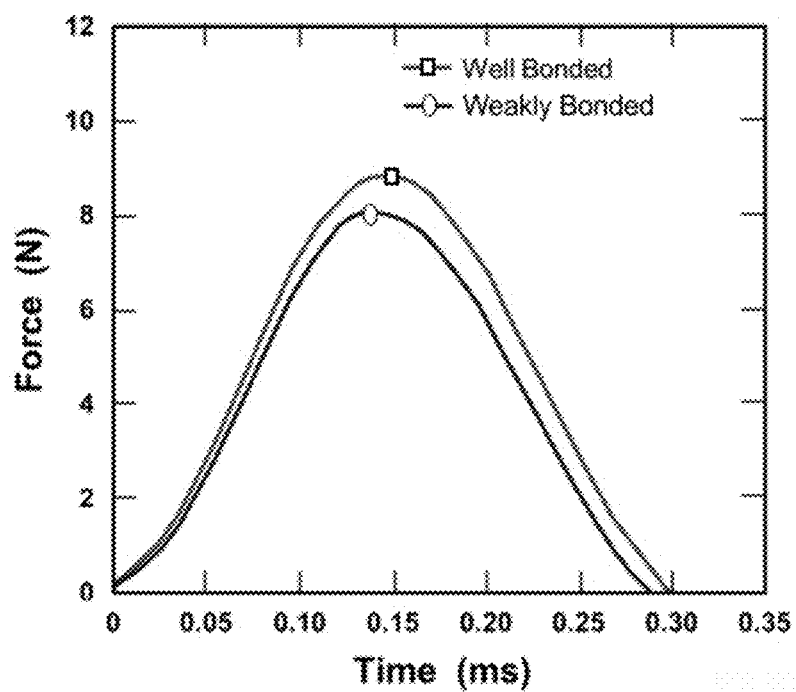
FIG. 10a shows the energy response from a well bonded and a weakly bonded composite material.

Testing of non-anatomical physical may be carried out in a similar manner as for dental structures, and for example, a non-destructive testing of bonds in composite laminates. Bonding composite structures together using adhesives provides many advantages over other joining methods. These advantages include distributing the load over a large bond area, reduced weight, and ability to join dissimilar materials together, higher stiffness and toughness over the bond area and in many cases lower manufacturing cost. However, one of the limitations when using adhesives is the inability to determine non-destructively if the bond joint assembled meets structural requirements using other methods and generally leads to a conservative design approach and applying fasteners through the bond to ensure joint integrity. The system and method of the present invention have the ability to non-destructively detect adhesive 'kiss' bonds, where the adhesive shear strength is low due to contamination on the bonding surfaces or improper handling, mixing, or curing of the adhesive, or even from poor surface preparation of molded surfaces where fluorocarbons, silicones, plasticizers, for example, may be introduced from the manufacturing process. These contaminants tend to decrease the contact angle between the adhesive and the bonding surface causing a decrease in shear strength. As a result, the bond that is formed may not be able to carry load as both substrates will in essence be 'kissing' one another. The present invention provides nondestructive testing to detect defects in composite structures. For an example, the present invention may be employed to compare two composite laminates where one was bonded following a poor surface preparation technique, while the other was bonded per common standard practices. In an actual experiment, two pre-cured carbon fiber/epoxy matrix laminates 305 mm×305 mm×1.59 mm (12 in.×12 in.×0.0625 in.) were bonded together with a 121° C. (250° F.) cure supported epoxy film adhesive. One specimen had release agent applied in a 152 mm×152 mm (6 in.×6 in.) area in the center of the laminate, which simulated a 'kiss' bond while the other bonded laminate had no release agent applied. To ensure the release agent created a poor bond, it was baked onto the laminate surface prior to bonding. Using an energy application tool 110, such as a tapping rod, the results shown in FIG. 10a show that a kiss bonded (weakly bonded) sample has a different response curve from a well-bonded curve. In bonding structures, the present invention may also be able to detect the difference in the thickness of the bonding agent. Since bonding agents are generally of a viscoelastic material, the thicker the agent layer, the more damping and thus a different response.

As mentioned above, the present invention provides the ease and speed of application and may be employed to detect and assess microleakage, gross recurrent decay, loose post/build-up, decay in post space, whether tooth is non-restorable, gross decay, near pulp exposure, enamel and dentinal cracks, internal alloy fracture, or even any bioengineering mismatch, any defect that create movement within the structure, and so on in a non-destructive manner. This is also true of industrial or physical structures noted above.

Although the invention has been described with respect to specific aspects, embodiments and examples thereof, these are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A device for determining structural characteristics, comprising:
   a housing having an open front end and a longitudinal axis;

an energy application tool mounted inside said housing, said energy application tool having a resting configuration and an active configuration;

a drive mechanism supported inside said housing, said drive mechanism being adapted for activating said energy application tool to move between said resting and active configurations to apply a set amount of energy to an object at a horizontal orientation, and connected to a control mechanism adapted to control said drive mechanism; and an inclinometer adapted to provide input to said control mechanism by measuring inclination of the device relative to the horizontal, wherein said control mechanism is adapted to prevent from beginning said activating of said energy application tool to move between said resting and active configurations when said input from said inclinometer indicates said inclination is beyond a predefined angular range of operation;

wherein said drive mechanism is adapted to vary a quantity of energy applied to move said energy application tool between said resting and active configurations based on said inclination to at least approximate said set amount of energy when said inclination is other than the horizontal and within said predefined angular range of operation, and said control mechanism comprising a preprogrammed set of instructions for said varying by said drive mechanism comprising stored preset values of engaging time and retracting delay time of said drive mechanism selected to even out an applied force by said energy application tool on said object by corresponding to a respective prior measured applied force by said energy application tool at each of particular angles within said angular predefined angular range of operation.

2. The device of claim 1, further comprising:

a contact portion disposed about said open end of said housing adapted to contact the object;

at least one force transferring component not directly coupled to said energy application tool, said at least one force transferring component being adapted to transfer an external contact force from said contact portion to another component along said longitudinal axis; and a force sensor adapted to measure said external contact force transferred through said at least one force transferring component.

3. The device of claim 2, wherein said at least one force transferring component is rigidly coupled to said contact portion.

4. The device of claim 2, wherein said at least one force transferring component comprises a force transfer sleeve rigidly coupled to said drive mechanism.

5. The device of claim 2, wherein said contact portion comprises a sleeve portion protruding from said open front end of said housing for a distance of at least as far as a position of said energy application tool in said active configuration, said sleeve portion having a hollow interior with a front end and a rear end and an object contacting portion at the front end of said sleeve portion.

6. The device of claim 1, wherein said drive mechanism comprises an electromagnetic coil.

7. The device of claim 1, wherein said inclinometer comprises an accelerometer.

8. The device of claim 7, wherein said accelerometer is selected from the group consisting of a three-axis accelerometer, a two-axis accelerometer and a one-axis accelerometer.

9. The device of claim 1, further comprising a disposable feature enveloping a portion of said device for minimizing contact between the device and the object during use.

10. The device of claim 1, wherein said predefined angular range of operation ranges from zero degrees angle to plus/minus forty-five degrees angle.

11. The device of claim 1, wherein said predefined angular range of operation ranges from zero degrees angle to plus/minus thirty degrees angle.

* * * * *